(12) United States Patent
Sligar et al.

(10) Patent No.: US 7,048,949 B2
(45) Date of Patent: May 23, 2006

(54) MEMBRANE SCAFFOLD PROTEINS

(75) Inventors: Stephen G. Sligar, Urbana, IL (US); Timothy H. Bayburt, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/990,087

(22) Filed: Nov. 20, 2001

(65) Prior Publication Data

US 2006/0057662 A1    Mar. 16, 2006

Related U.S. Application Data

(60) Provisional application No. 60/252,233, filed on Nov. 20, 2000.

(51) Int. Cl.
*A61K 9/14* (2006.01)
*C07K 14/00* (2006.01)
*C07K 14/435* (2006.01)

(52) U.S. Cl. .................. 424/499; 530/350; 530/402
(58) Field of Classification Search .................. 530/350
See application file for complete search history.

(56) References Cited

U.S. PATENT DOCUMENTS

| 6,172,262 B1 | 1/2001 | McQuade et al. | 564/182 |
| 6,248,353 B1 | 6/2001 | Singh | 424/450 |

FOREIGN PATENT DOCUMENTS

| WO | WO 93/17031 | 9/1993 |
| WO | WO 00/75187 | 12/2000 |
| WO | WO 01/02551 A2 | 1/2001 |

OTHER PUBLICATIONS

Bayburt et al, Reconstitution and imaging of a membrane protein in a nanometer-size phospholipid bilayer. Journal of Structural Biology, 123:37-44, 1998.*
Bayhurt et al, Single molecule height measurements on a membrane protein in nanometer-scale phospholipid bilary disks. Langmuir, 16:5993-5997, published on web Jun. 17, 2000.*
Carlson et al, Imaging and Manipulation of high -density lipoproteins. Biophysical Journal, 73:1184-1189, 1997.*
Jonas, A. Reconstruction of high-density lipoproteins. Methods in Enzymology , vol., 128, pp. 553-582, 1986.*
Bergeron et al., Apolipoprotein A-I conformation in reconstituted discoidal lipoproteins varying in phospholipid and cholesterol content. J. Biol. chem. 270: 27429-27438, 1995.*
Bergeron et al., Characterization of human apolipoprotein A-I expressed in *Escherichia coli*. Biochim Biophys Acta 1344:139-152, 1997.*
Barnes et al., A review of central 5-HT receptors and their function. 38:1083-1152, 1999.*
Ji et al., G protein-coupled receptors. 273:17299-17302; 1998.*
Atkinson, D. and Small, D.M., "Recombinant Lipoproteins:Implications for Structure and Assembly of Native Lipoproteins" (1986) Ann. Rev. Biophys. Chem. 15:403-456.
Bayburt, T.H. et al., "Reconstitution and Imaging of a Membrane Protein in a Nanometer-Size Phospholipid bilayer" (1998) J. Struct. Biol. 123:37-44.
Bayburt, T.H. et al., "Single Molecule Height Measurements on a Membrane Protein in Nanometer-Scale Phospholipid Bilayer Disks" (Jun. 17, 2000) Langmuir 16(14):5993-5997.
Boguski, M.S. et al., "On computer-assisted analysis of biological sequences: proline punctuation, consensus sequences, and apolipoprotein repeats" (1986) J. of Lipid Research 27:1011-1034.

(Continued)

*Primary Examiner*—Ruixiang Li
(74) *Attorney, Agent, or Firm*—Greenlee, Winner & Sullivan, P.C.

(57) ABSTRACT

Membrane proteins are difficult to express in recombinant form, purify, and characterize, at least in part due to their hydrophobic or partially hydrophobic properties. Membrane scaffold proteins (MSP) assemble with target membrane or other hydrophobic or partially hydrophobic proteins or membrane fragments to form soluble nanoscale particles which preserve their native structure and function; they are improved over liposomes and detergent micelles. In the presence of phospholipid, MSPs form nanoscopic phospholipid bilayer disks, with the MSP stabilizing the particle at the perimeter of the bilayer domain. The particle bilayer structure allows manipulation of incorporated proteins in solution or on solid supports, including for use with such surface-sensitive techniques as scanning probe microscopy or surface plasmon resonance. The nanoscale particles facilitate pharmaceutical and biological research, structure/function correlation, structure determination, bioseparation, and drug discovery.

5 Claims, 28 Drawing Sheets

OTHER PUBLICATIONS

Borhani, D.W. et al., "Crystal structure of truncated human apolipoprotein A-I suggests a lipid-bound conformation" (Nov. 1997) Proc. Natl. Acad. Sci. USA 94:12291-12296.

Brouillette, C.G. et al., "Structural Studies of Apolipoprotein A-I/Phosphatidylcholine Recombinants by High-Field Proton NMR, Nondenaturing Gradient Gel Electrophoresis, and Electron Microscopy" (1984) Biochemistry 23:359-367.

Carlson, J. W. et al., "Nanopatterning Phospholipid Bilayers" (Mar. 17, 2000) Langmuir 16(8):3927-3931.

Carlson, J.W. et al., "Imaging and Manipulation of High-Density Lipoproteins" (Sep. 1997) Biophys. J. 73:1184-1189.

Dalton, M.B. and Swaney, J.B., "Structural and Functional Domains of Apolipoprotein A-I within High Density Lipoproteins" (Sep. 15, 1993) J. Biol. Chem. 268(26):19274-19283.

Durbin, D.M. and Jonas, A., "Lipid-free apolipoproteins A-I and A-II promote remodeling of reconstituted high density lipoproteins and alter their reactivity with lecithin:cholesterol acyltransferase"(Dec. 1999) J. Lipid Research 40(12):2293-2302.

Fidge, N.H., "High density lipoprotein receptors, binding proteins, and ligands" (Feb. 1999) J. Lipid Research 40(2):187-201.

Fielding, P.E. and Fielding, C.J., "Dynamics of lipoprotein transport in the circulatory system" *Biochemistry of Lipids, Lipoproteins, and Membranes.* D.E. Vance and J. Vance. (1991) Amsterdam, Elsevier Press Chapter 15, pp. 427-459.

Forte, T.M. et al., "Electron microscopic study on reassembly of plasma high density apoprotein with various lipids" (1971) Biochim. Biophys. Acta 248:381-386.

Frank, P.G. et al., "Deletion of Central α-Helices in Human Apolipoprotein A-I: Effect on Phospholipid Association" (1997) Biochemistry 36:1798-1806.

Friis, E.P. et al., "An approach to long-range electron transfer mechanisms in mettalloproteins: in situ scanning tunneling ,microscopy with submolecular resolution" (Feb. 1999) Proc. Natl. Acad. Sci. USA 96:1379-1384.

Glomset, J.A., "The plasma lecithin:cholesterol acyltransferase reaction" (1968) J. Lipid Research 9:155-167.

Holvoet, P. et al., "Phospholipid Binding and Lecithin-Cholesterol Acyltransferase Activation Properties of Apolipoprotein A-I Mutants" (1995) Biochemistry 34:13334-13342.

Jin, L et al., "Surface Plasmon Resonance Biosensor Studies of Human Wild-Type and Mutant Lecithin Cholesterol Acyltransferase Interactions with Lipoproteins" (Nov. 5, 1999). Biochemistry 38(47):15659-15665.

Jonas, A., "Reconstitution of High Density Lipoproteins" (1986) Methods Enzymol. 128:553-582.

Jonas, A., "Lecithin-cholesterol acyltransferase in the metabolism of high-density lipoproteins"(1991) Biochim,. Biophys. Acta 1084:205-220.

Jonas, A. et al., "Defined Apolipoprotein A-I Conformation in Reconstituted High Density Lipoprotein Discs"(Mar. 25, 1989) J. Biol. Chem. 264(9):4818-4824.

Koppaka, V. et al., "The Structure of Human Lipoprotein A-I" (May 1999) J. Biol. Chem. 274(21):14541-14544.

Miller, J.P. et al., "X-ray Diffraction Analysis of Cytochrome P450 2B4 Reconstituted into Liposomes" (1996) Biochemistry 35:1466-1474.

Mukhopadhyay, R. et al., "A scanning tunneling microscopy study of *Clostridium pasteurianum* rubredoxin" (Mar. 31, 2000) J. Inorg. Biochem. 78:251-254.

Phillips, J.C. et al., "Predicting the Structure of Apolipoprotein A-I in Reconstituted High-Density Lipoprotein Disks" (Nov. 1997) Biophysics Journal 73:2337-2346.

Robinson, C.R. and Sligar, S.G., "Changes in solvation during DNA binding and cleavage are critical to altered specificity of the *Eco*RI endonuclease" (Mar. 1998) Proc. Natl. Acad. Sci. USA 95:2186-2191.

Robinson, C.R. and Sauer, R.T. "Optimizing the stability of single-chain proteins by linker length and composition mutagenesis" (May 1998) Proc. Natl. Acad. Sci. USA 95(II):5929-5934.

Rogers, D.P. et al., "Structural Analysis of Apolipoprotein A-I: Effects of Amino-and Carboxy-Terminal Deletions on the Lipid-Free Structure" (1998) Biochemistry 37:945-955.

Rogers, D.P. et al., "The Lipid-Free Structure of Apolipoprotein A-I: Effects of Amino-Terminal Deletions" (1998) Biochemistry 37(34):11714-11725.

Salamon, Z., "Coupled Plasmon—Waveguide Resonators: A New Spectroscopic Tool for Probing Proteolipid Film Structure and Properties" (Nov. 1997) Biophys. Journal 73:2791-2797.

Schafmeister, C. et al., "Structure at 2.5 Å of a Designed Peptide That Maintains Solubility of Membrane Proteins" (Oct. 1993) Science 262:734-738.

Segrest, J.P. et al., "A Detailed Molecular Belt Model for Apolipoprotein A-I in Discoidal High Density Lipoprotein" (Nov. 5, 1999) J. Biol. Chem. 274(45):31755-31758.

Sklar, L.A. et al., "Solubilization and Display of G Protein-Coupled Receptors on Beads for Real-Time Fluorescence and Flow Cytometric Analysis" (May 2000) BioTechniques 28(5):976-985.

Tocanne, J.F. et al., "Lipid domains and lipid/protein interactions in biological membranes" (1994) Chemistry and Physics of Lipids 73:139-158.

Wald, J.H. et al., "Investigation of the Lipid Domains and Apolipoprotein Orientation in Reconstituted High Density Lipoproteins by Fluorescence and IR Methods" (Nov. 1990) J. Biol. Chem. 265(32):20044-20050.

Wald, J. H. et al., "Structure of Apolipoprotein A-I in Three Homogeneous, Reconstituted High Density Lipoprotein Particles" (Nov. 1990) J. Biol. Chem. 265(32):20037-20043.

Wang, M. et al., "Three-dimensional structure of NADPH-cytochrome P450 reductase: Prototype of FMN and FAD-containing enzymes" (1997) Proc. Natl. Acad. Sci. USA 94:8411-8416.

Wlodawer, A. et al., "High-Density Lipoprotein Recombinants: Evidence For A Bicycle Tire Micelle Structure Obtained By Neutron Scattering and Electron Microscopy" (Aug. 1979) FEBS Lett. 104(2):231-235 Segr35.

Zuck, P. et al., "Ligand-receptor binding measured by laser-scanning imaging" (Sep. 1999) Proc. Natl. Acad. Sci. USA 96:11122-11127.

Bruhn et al. (1991) "An Approach to the Functional Analysis of Lecithin-Cholesterol Acryltransferase. Activation by Recombinant Normal and Mutagenized Apolipoprotein AI," *Biological Chemistry Hoppee-Seyler* 372(3):225-234.

Burgess et al. (Nov., 2 1999) "Deletion of the C-Terminal Domain of Apolipoprotein A-I Impairs Cell Surface Binding and Lipid Efflux in Macrophage," *Biochem.* 38(44):14524-14533.

Frank et al. (1998) "Importance of Central α-Helixes of Human Apolipoprotein A-I in the Maturation of High Density Lipoproteins," *Biochem.* 37(39):13902-13909.

Gillotte et al. (1996) "Apolipoprotein A-I Structural Modification and the Functionality of Reconstituted High Density Lipoprotein Particles in Cellular Cholesterol Efflux," *J. Biol. Chem.* 271(39):23792-23798.

Gillotte et al. (Jan., 1999)."Apolipoprotein-Mediated Plasma Membrane Microsolubilization. Role of Lipid Affinity and Membrane Penetration in the Efflux of Cellular Cholesterol and Phospholipid," *J. Biol. Chem.* 274(4):2021-2028.

Laccotripe et al. (1997) "The Carboxyl-Terminal Hydrophobic Residues of Apolipoprotein A-I Affect its Rate of Phospholipid Binding and its Association with High Density Lipoprotein," *J. Biol. Chem.* 272(28):17511-17522.

Liadaki et al. (Jul. 2000) "Binding of High Density Lipoprotein (HDL) and Discoidal Reconstituted HDL to the HDL Receptor Scavenger Receptor Class B Type I. Effect of Lipid Association and apoA-I Mutations on Receptor Binding," *J. Biol. Chem.* 275(28):21262-21271.

Marcel et al. (1998) "Definition of Apolipoprotein A-I Domains Involved in Reverse Cholesterol Transport," *International Congress Series* 1155:(Atherosclerosis XI)1149-1153.

McManus et al. (Feb. 2000) "Distinct Central Amphipathic α-Helices in Apolipoprotein A-I Contribute to the in Vivo Maturation of High Density Lipoprotein by Either Activating Lechithin-Cholesterol Acyltransferase of Binding Lipids," *J. Biol. Chem.* 275(7):5043-5051.

Minnich et al. (1992) "Site-Directed Mutagenesis and Structure-Function Analysis of the Human Apolipoprotein A-I. Relation Between Lecithin-Cholesterol Acyltransferase Activation and Lipid Binding," *J. Biol. Chem.* 267(23):16553-16560.

Reardon et al. (Oct. 2001) "In Vivo Studies of HDL Assembly and Metabolism Using Adenovirus-Mediated Transfer of ApoA-I Mutants in ApoA-I-Deficient Mice," *Biochem.* 40(45):13670-13680.

Rogers et al. (1997) "Truncation of the Amino Terminus of Human Apolipoprotein A-I Substantially Alters Only the Lipid-Free Conformation," *Biochem.* 36(2):288-300.

Rosseneu et al. (1992) "Contribution of Helix-Helix Interactions to the Stability of Apolipoprotein-Lipid Complexes," *International Congress Series* 1001:(High Density) Lipoproteins Atheroscler. III)105-114.

Sorci-Thomas et al. (1998) "The Hydrophobic Face Orientation of Apolipoprotein A-I Amphipathic Helix Domain 143-164 Regulates Lecthin: Cholesterol Acyltransferase Activation," *J. Biol. Chem.* 273(19):11776-11782.

Sorci-Thomas et al. (1997) "Alteration in Apolipoprotein A-I 22-Mer Repeat Order Results in a Decrease in Lecithin: Cholesterol Acyltransferase Reactivity," *J. Biol. Chem.* 272(11):7278-7284.

Scott et al. (Dec. 2001) "The N-Terminal Globular Domain and the First Class A Amphipathic Helix of Apolipoprotein A-I are Important for Lecithin: Cholesterol Acyltransferase Activation and the Maturation of High Density Lipoprotein in Vivo," *J. Biol. Chem.* 276(52):48716-48724.

Sviridov et al. (Jun. 2000) "Identification of a Sequence of Apolipoprotein A-I Associated With the Activation of Lecithin: Cholesterol Acyltransferase," *J. Biol. Chem.* 275(26):19707-19712.

Sviridov et al. (1996) "Efflux of Cellular Cholesterol and Phospholipid to Apolipoprotein A-I Mutants," *J. Biol. Chem.* 271(52):33277-33283.

Bakker, E.P. and Caplan, S.R. (1982), "Phospholipid Substitution of the Purple Membrane," Methods in Enzymol. 88:26-30.

Bayburt, T.H. et al., (Dec. 2002) "Self-Assembly of Discoidal Phospholipid Bilayer Nanoparticles with Membrane Scaffold Proteins"; *Nano Letters* 2:853-856.

Bayburt, T.H. et. al., (May 2002) "Single Molecule Height Measurements on Microsomal Cytochrome P450 in nanometer-Scale Phospholipid Bilayer Disks"; *Proceedings of the National Academy of Sciences* 99:6725-6730.

Bayburt, T.H. et al. (Nov. 2003) "Self-Assembly of Single Integral Membrane Proteins into Soluble Nanoscale Phospholipid Bilayers"; *Protein Science* 12:2476-2481.

Bayley, H. et al. (1982), "Delipidation, Renaturation, and Reconstitution of Bacteriorhodopsin," Methods Enzymol. 88:74-81.

Brouillette, C. et al., (2001), "Structural models of human apolipoprotein A-I: a critical analysis and review," Biochim. Biophys. Acta 1531:4-46.

Carlson, J.W. et al., (1997) "Imaging and Manipulation of High-Density Lipoproteins," *Biophysical J.* 73:1184-1189.

Carlson, J.W. et al. (Dec. 2000) "Nanopatterning Phospholipid Bilayers"; *Langmuir* 16:3927-3931.

Chen, J.S. et al., (2002) "Amino Acids in SRS1 and SRS6 are Critical for Furanocoumarin Metabolism by CYP6B1v1, a Cytochrome P450 Monooxygenase," *Insect Molecular Biology* 11:175-186.

Civjan, N.R. et al., (2003) "Direct Solubilization of Heterologously Expressed Membrane Proteins by Incorporation into Nanoscale Lipid Bilayers"; *BioTechniques* 35:556-563.

Dencher, N.A. and Heyn, M.P. (1982) "Preparation and Properties of Monomeric Bacteriorhodosin," *Methods Enyzmol.* 88:5-10.

Denisov, I.G., et al. (Mar. 2004) "Directed Self Assembly of Monodisperse Phospholipid Bilayer Nanodiscs with Controlled Size"; *J. Am. Chem. Soc.,* In Press.

Duan, et al. (2004) Co-incorporation of Heterologously-Expressed *Arabidopsis* Cytochrome P450 and P450 Reductase into Soluble Nanoscale Lipid Bilayers; *Archives Biochemistry and Biophysics,* In Press.

Dubois et al. (Jun. 2001) "Self-Assembly or Regular Hollow Icosahedra in Salt-Free Catanionic Solutions," *Nature* 411:672-675.

Heyn, M.P. et al. (1982) "Reconstitution of Monomeric Bacteriorhodopsin into Phospholipid Vesicles;" Methods Enzymol. 88:31-35.

Imaoka, S. et al., (1992), "Role of Phospholipids in Reconstituted Cytochrome P450 3A Form and Mechanism of Their Activation of Catalytic Activity," *Biochemistry* 31:6063-6069.

Korenbrot, J.I. (1982), "The Assembly of Bacteriorhodopsin-Containing Planar Membranes by the Sequential Transfer of Air-Water Interface Films," Methods Enzymol. 88:45-55.

Marheineke, K. et al., (1998), "Lipid composition of *Spodoptera frugiperda* (Sf9) and *Trichoplusia ni* (Tn) insect cells used for baculovirus infection," *FEBS Letters* 441:49-52.

McGregor, C-L. (Feb. 2003), "Lipopeptide detergents designed for the structural study of membrane proteins,"*Nature Biotechnol.* 21:171-176.

Rezaie et al. (1992), "Expression and Purification of a Soluble Tissue Factor Fusion Protein with an Epitope for an Unusual Calcium-Dependent Antibody," *Protein Expression and Purification* 3:453-460.

Savelli, G. et al. (2000), "Enzyme activity and stability control by amphiphilic self-organizing systems in aqueous solutions," *Curr. Opin. Colloid & Interface Science* 5:111-117.

Shaw, A.W. et al., (Jan. 2004) "Phospholipid Phase Transitions in Homogeneous Nanometer Scale Bilayer Discs"; *FEBS Letters* 556:260-264.

Skutachev, V.P. (1982), "A Single Turnover Study of Photoelectric Current-Generating Proteins," Methods Enzymol. 88:35-45.

Sligar, S. (2003) "Finding a Single-Molecule Solution for Membrane Proteins"; *Biochem. Biophys. Res. Comm.* 312:115-119.

* cited by examiner

Liposomes　　　Detergent Micelles　　　Disks

DEPPQSPWDRVKDLATVYVDVLKDSGRDYVSQFEGSALGKQLN * LKLLDNWDSVTSTFSKLREQLG *
1                                        43 44                    65
PVTQEFWDNLEKETEGLRQEMS * KDLEEVKAKVQ * PYLDDFQKKWQEEMELYRQKVE *
66                  87 88          98 99                    120
PLRAELQEGARQKLHELQEKLS * PLGEEMRDRARAHVDALRTHLA * PYSDELRQRLAARLEALKENGG *
121                 142 143                 164 165                    186
ARLAEYHAKATEHLSTLSEKAK * PALEDLRQGLL * PVLESEKVSFLSALEEYTKKLN TQ
187                 208 209        219 220                 241

FIG. 4

SEQUENCE LISTING

```
<160> NUMBER OF SEQ ID NOS: 46

<210> SEQ ID NO 1
<211> LENGTH: 762
<212> TYPE: DNA
<213> ORGANISM: Homo sapiens
<220> FEATURE:
<221> NAME/KEY: misc_feature
<222> LOCATION: (1)..(762)
<223> OTHER INFORMATION: Restriction sites, Nco I and Hind III, are at
      5' and 3' termini.

<400> SEQUENCE: 1
ccatggccca tttctggcag caagatgaac ccccccagag ccctgggat cgagtgaagg      60 acctggccac tgtgtacgtg gatgtgctca aagacagcgg cagagactat gtgtcccagt    120
ttgaaggctc cgccttggga aaacagctaa acctaaagct ccttgacaac tgggacagcg    180
tgacctccac cttcagcaag ctgcgcgaac agctcggccc tgtgacccag gagttctggg    240
ataacctgga aaaggagaca gagggcctga ggcaagagat gagcaaggat ctggaggagg    300
tgaaggccaa ggtgcagccc tacctggacg acttccagaa gaagtggcag gaggagatgg    360
agctctaccg ccagaaggtg gagccgctgc gcgcagagct ccaagagggc gcgcgccaga    420
agctgcacga gctgcaagag aagctgagcc cactgggcga ggagatgcgc gaccgcgcgc    480
gcgcccatgt ggacgcgctg cgcacgcatc tggccccta cagcgacgag ctgcgccagc    540
gcttggccgc gcgccttgag gctctcaagg agaacggcgg cgccagactg gccgagtacc    600
acgccaaggc caccgagcat ctgagcacgc tcagcgagaa ggccaagccc gcgctcgagg    660
acctccgcca aggcctgctg cccgtgctgg agagcttcaa ggtcagcttc ctgagcgctc    720
tcgaggagta cactaagaag ctcaacaccc agtaataagc tt                       762

<210> SEQ ID NO 2
<211> LENGTH: 250
<212> TYPE: PRT
<213> ORGANISM: Homo sapiens
```

```
<400> SEQUENCE: 2

Met Ala His Phe Trp Gln Gln Asp Glu Pro Pro Gln Ser Pro Trp Asp
 1               5                  10                  15

Arg Val Lys Asp Leu Ala Thr Val Tyr Val Asp Val Leu Lys Asp Ser
            20                  25                  30

Gly Arg Asp Tyr Val Ser Gln Phe Glu Gly Ser Ala Leu Gly Lys Gln
        35                  40                  45

Leu Asn Leu Lys Leu Leu Asp Asn Trp Asp Ser Val Thr Ser Thr Phe
    50                  55                  60

Ser Lys Leu Arg Glu Gln Leu Gly Pro Val Thr Gln Glu Phe Trp Asp
65                  70                  75                  80

Asn Leu Glu Lys Glu Thr Glu Gly Leu Arg Gln Glu Met Ser Lys Asp
                85                  90                  95

Leu Glu Glu Val Lys Ala Lys Val Gln Pro Tyr Leu Asp Asp Phe Gln
            100                 105                 110

Lys Lys Trp Gln Glu Glu Met Glu Leu Tyr Arg Gln Lys Val Glu Pro
        115                 120                 125

Leu Arg Ala Glu Leu Gln Glu Gly Ala Arg Gln Lys Leu His Glu Leu
    130                 135                 140

Gln Glu Lys Leu Ser Pro Leu Gly Glu Glu Met Arg Asp Arg Ala Arg
145                 150                 155                 160

Ala His Val Asp Ala Leu Arg Thr His Leu Ala Pro Tyr Ser Asp Glu
                165                 170                 175

Leu Arg Gln Arg Leu Ala Ala Arg Leu Glu Ala Leu Lys Glu Asn Gly
            180                 185                 190

Gly Ala Arg Leu Ala Glu Tyr His Ala Lys Ala Thr Glu His Leu Ser
        195                 200                 205

Thr Leu Ser Glu Lys Ala Lys Pro Ala Leu Glu Asp Leu Arg Gln Gly
    210                 215                 220

Leu Leu Pro Val Leu Glu Ser Phe Lys Val Ser Phe Leu Ser Ala Leu
225                 230                 235                 240

Glu Glu Tyr Thr Lys Lys Leu Asn Thr Gln
                245                 250

<210> SEQ ID NO 3
<211> LENGTH: 61
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 3
tataccatgg gccatcatca tcatcatcat atagaaggaa gactaaagct ccttgacaac    60
t                                                                    61

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 4
gcaagcttat tactgggtgt tgagcttctt                                     30
```

<210> SEQ ID NO 5
<211> LENGTH: 654
<212> TYPE: DNA
<213> ORGANISM: Artificial Sequence
<220> FEATURE:
<223> OTHER INFORMATION: Description of Artificial Sequence: Nucleotide sequence encoding Synthetic peptide.

<400> SEQUENCE: 5

```
tataccatgg gccatcatca tcatcatcat atagaaggaa gactaaagct ccttgacaac      60
tgggacagcg tgacctccac cttcagcaag ctgcgcgaac agctcggccc tgtgacccag     120
gagttctggg ataacctgga aaaggagaca gagggcctga ggcaggagat gagcaaggat     180
ctggaggagg tgaaggccaa ggtgcagccc tacctggacg acttccagaa gaagtggcag     240
gaggagatgg agctctaccg ccagaaggtg agccgctgc gcgcagagct ccaagagggc     300
gcgcgccaga agctgcacga gctgcaagag aagttgagcc cactgggcga ggagatgcgc     360
gaccgcgcgc gcgcccatgt ggacgcgctg cgcacgcatc tggcccccta cagcgacgag     420
ctgcgccagc gcttggccgc gcgccttgag gctctcaagg agaacggcgg cgccagactg     480
gccgagtacc acgccaaggc caccgagcat ctgagcacgc tcagcgagaa ggccaaaccc     540
gcgctcgagg acctccgcca aggcctgctg cccgtgctgg agagcttcaa ggtcagcttc     600
ctgagcgctc tcgaggagta cactaagaag ctcaacaccc agtaataagc ttgc           654
```

<210> SEQ ID NO 6
<211> LENGTH: 212
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

```
Met Gly His His His His His Ile Glu Gly Arg Leu Lys Leu Leu
  1               5                  10                  15

Asp Asn Trp Asp Ser Val Thr Ser Thr Phe Ser Lys Leu Arg Glu Gln
             20                  25                  30

Leu Gly Pro Val Thr Gln Glu Phe Trp Asp Asn Leu Glu Lys Glu Thr
         35                  40                  45

Glu Gly Leu Arg Gln Glu Met Ser Lys Asp Leu Glu Glu Val Lys Ala
     50                  55                  60

Lys Val Gln Pro Tyr Leu Asp Asp Phe Gln Lys Lys Trp Gln Glu Glu
 65                  70                  75                  80

Met Glu Leu Tyr Arg Gln Lys Val Glu Pro Leu Arg Ala Glu Leu Gln
                 85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190
```

```
Ser Phe Lys Val Ser Phe Leu Ser Ala Leu Glu Glu Tyr Thr Lys Lys
        195                 200                 205

Leu Asn Thr Gln
    210

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 7
taccatggca aagctccttg acaactg                                     27

<210> SEQ ID NO 8
<211> LENGTH: 619
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 8
taccatggca aagctccttg acaactggga cagcgtgacc tccaccttca gcaagctgcg    60
cgaacagctc ggccctgtga cccaggagtt ctgggataac ctggaaaagg agacagaggg   120
cctgaggcag gagatgagca aggatctgga ggaggtgaag gccaaggtgc agccctacct   180
ggacgacttc agaagaagt ggcaggagga gatggagctc taccgccaga aggtggagcc   240
gctgcgcgca gagctccaag agggcgcgcg ccagaagctg cacgagctgc aagagaagtt   300
gagcccactg ggcgaggaga tgcgcgaccg cgcgcgcgcc catgtggacg cgctgcgcac   360
gcatctggcc ccctacagcg acgagctgcg ccagcgcttg gccgcgcgcc ttgaggctct   420
caaggagaac ggcggcgcca gactggccga gtaccacgcc aaggccaccg agcatctgag   480
cacgctcagc gagaaggcca aacccgcgct cgaggacctc cgccaaggcc tgctgcccgt   540
gctggagagc ttcaaggtca gcttcctgag cgctctcgag gagtacacta agaagctcaa   600
cacccagtaa taagcttgc                                              619

<210> SEQ ID NO 9
<211> LENGTH: 201
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Ala Lys Leu Leu Asp Asn Trp Asp Ser Val Thr Ser Thr Phe Ser
1               5                   10                  15

Lys Leu Arg Glu Gln Leu Gly Pro Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
```

```
                    85                  90                  95
Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln
            195                 200

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 10
taccatggca aagctccttg acaactg                                       27

<210> SEQ ID NO 11
<211> LENGTH: 61
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 11
tataccatgg gccatcatca tcatcatcat atagaaggaa gactaaagct ccttgacaac    60
t                                                                   61

<210> SEQ ID NO 12
<211> LENGTH: 52
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 12
taagaagctc aacacccagg gtaccggtgg aggtagtgga ggtggtaccc ta            52

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 13
cagggtaccg gtggaggtag tggaggtggt accctaaagc tccttgacaa               50

<210> SEQ ID NO 14
```

```
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 14
gcaagcttat tactgggtgt tgagcttctt                                    30

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Thr Gly Gly Gly Ser Gly Gly Gly Thr
  1               5                  10

<210> SEQ ID NO 16
<211> LENGTH: 1260
<212> TYPE: DNA
<213> ORGANISM: Artificial Sequence
<220> FEATURE:
<223> OTHER INFORMATION: Description of Artificial Sequence: Nucleotide
      sequence encoding a synthetic peptide.

<400> SEQUENCE: 16
tataccatgg gccatcatca tcatcatcat atagaaggaa gactaaagct ccttgacaac     60
tgggacagcg tgacctccac cttcagcaag ctgcgcgaac agctcggccc tgtgacccag    120
gagttctggg ataacctgga aaaggagaca gagggcctga ggcaggagat gagcaaggat    180
ctggaggagt gaaggccaa ggtgcagccc tacctggacg acttccagaa gaagtggcag     240
gaggagatgg agctctaccg ccagaaggtg agccgctgc gcgcagagct ccaagagggc    300
gcgcgccaga agctgcacga gctgcaagag aagctgagcc cactgggcga ggagatgcgc   360
gaccgcgcgc gcgcccatgt ggacgcgctg cgcacgcatc tggcccccta cagcgacgag   420
ctgcgccagc gcttggccgc gcgccttgag gctctcaagg agaacggcgg cgccagactg   480
gccgagtacc acgccaaggc caccgagcat ctgagcacgc tcagcgagaa ggccaagccc   540
gcgctcgagg acctccgcca aggcctgctg cccgtgctgg agagcttcaa ggtcagcttc   600
ctgagcgctc tcgaggagta cactaagaag ctcaacaccc agggtaccct aaagctcctt   660
gacaactggg acagcgtgac ctccaccttc agcaagctgc gcgaacagct cggccctgtg   720
acccaggagt tctgggataa cctggaaaag gagacagagg gcctgaggca ggagatgagc   780
aaggatctgg aggaggtgaa ggccaaggtg cagccctacc tggacgactt ccagaagaag   840
tggcaggagg agatggagct ctaccgccag aaggtgagc cgctgcgcgc agagctccaa    900
gagggcgcgc gccagaagct gcacgagctg caagagaagc tgagcccact gggcgaggag   960
atgcgcgacc gcgcgcgcgc ccatgtggac gcgctgcgca cgcatctggc ccctacagc  1020 gacgagctgc gccagcgctt ggccgcgcgc cttgaggctc tcaaggagaa cggcggcgcc  1080
agactggccg agtaccacgc caaggccacc gagcatctga gcacgctcag cgagaaggcc  1140
aagcccgcgc tcgaggacct ccgccaaggc ctgctgcccg tgctggagag cttcaaggtc  1200
agcttcctga gcgctctcga ggagtacact aagaagctca cacccagta ataagcttgc  1260
```

<210> SEQ ID NO 17
<211> LENGTH: 414
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

```
Met Gly His His His His His His Ile Glu Gly Arg Leu Lys Leu Leu
 1               5                  10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln Gly Thr Leu Lys Leu Leu Asp Asn Trp Asp Ser Val
    210                 215                 220

Thr Ser Thr Phe Ser Lys Leu Arg Glu Gln Leu Gly Pro Val Thr Gln
225                 230                 235                 240

Glu Phe Trp Asp Asn Leu Glu Lys Glu Thr Glu Gly Leu Arg Gln Glu
                245                 250                 255

Met Ser Lys Asp Leu Glu Glu Val Lys Ala Lys Val Gln Pro Tyr Leu
            260                 265                 270

Asp Asp Phe Gln Lys Lys Trp Gln Glu Glu Met Glu Leu Tyr Arg Gln
        275                 280                 285

Lys Val Glu Pro Leu Arg Ala Glu Leu Gln Glu Gly Ala Arg Gln Lys
    290                 295                 300

Leu His Glu Leu Gln Glu Lys Leu Ser Pro Leu Gly Glu Glu Met Arg
305                 310                 315                 320

Asp Arg Ala Arg Ala His Val Asp Ala Leu Arg Thr His Leu Ala Pro
                325                 330                 335

Tyr Ser Asp Glu Leu Arg Gln Arg Leu Ala Ala Arg Leu Glu Ala Leu
            340                 345                 350

Lys Glu Asn Gly Gly Ala Arg Leu Ala Glu Tyr His Ala Lys Ala Thr
        355                 360                 365
```

```
Glu His Leu Ser Thr Leu Ser Glu Lys Ala Lys Pro Ala Leu Glu Asp
    370                 375                 380

Leu Arg Gln Gly Leu Leu Pro Val Leu Glu Ser Phe Lys Val Ser Phe
385                 390                 395                 400

Leu Ser Ala Leu Glu Glu Tyr Thr Lys Lys Leu Asn Thr Gln
                405                 410
```

<210> SEQ ID NO 18
<211> LENGTH: 1282
<212> TYPE: DNA
<213> ORGANISM: Artificial Sequence
<220> FEATURE:
<223> OTHER INFORMATION: Description of Artificial Sequence: Synthetic
      nucleotide sequence encoding an artificial
      protein.

<400> SEQUENCE: 18

```
taccatgggc catcatcatc atcatcatat agaaggaaga ctaaagctcc ttgacaactg      60
ggacagcgtg acctccacct tcagcaagct gcgcgaacag ctcggccctg tgacccagga    120
gttctgggat aacctggaaa aggagacaga gggcctgagg caggagatga gcaaggatct    180
ggaggaggtg aaggccaagg tgcagcccta cctggacgac ttccagaaga gtggcagga    240 ggagatggag ctctaccgcc agaaggtgga gccgctgcgc gcagagctcc aagagggcgc    300
gcgccagaag ctgcacgagc tgcaagagaa gctgagccca ctgggcgagg agatgcgcga    360
ccgcgcgcgc gcccatgtgg acgcgctgcg cacgcatctg gccccctaca gcgacgagct    420
gcgccagcgc ttggccgcgc gccttgaggc tctcaaggaa acggcggcg ccagactggc    480 cgagtaccac gccaaggcca ccgagcatct gagcacgctc agcgagaagg ccaagcccgc    540
gctcgaggac ctccgccaag gcctgctgcc cgtgctggag agcttcaagg tcagcttcct    600
gagcgctctc gaggagtaca ctaagaagct caacacccag ggtaccggtg aggtagtgg    660 aggtggtacc ctaaagctcc ttgacaactg ggacagcgtg acctccacct tcagcaagct    720
gcgcgaacag ctcggccctg tgacccagga gttctgggat aacctggaaa aggagacaga    780
gggcctgagg caggagatga gcaaggatct ggaggaggtg aaggccaagg tgcagcccta    840
cctggacgac ttccagaaga gtggcagga ggagatggag ctctaccgcc agaaggtgga    900
gccgctgcgc gcagagctcc aagagggcgc gcgccagaag ctgcacgagc tgcaagagaa    960
gctgagccca ctgggcgagg agatgcgcga ccgcgcgcgc gcccatgtgg acgcgctgcg   1020
cacgcatctg gccccctaca gcgacgagct gcgccagcgc ttggccgcgc gccttgaggc   1080
tctcaaggag aacggcggcg ccagactggc cgagtaccac gccaaggcca ccgagcatct   1140
gagcacgctc agcgagaagg ccaagcccgc gctcgaggac ctccgccaag gcctgctgcc   1200
cgtgctggag agcttcaagg tcagcttcct gagcgctctc gaggagtaca ctaagaagct   1260
caacacccag taataagctt gc                                            1282
```

<210> SEQ ID NO 19
<211> LENGTH: 422
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Met Gly His His His His His His Ile Glu Gly Arg Leu Lys Leu Leu
 1               5                  10                  15
```

```
Asp Asn Trp Asp Ser Val Thr Ser Thr Phe Ser Lys Leu Arg Glu Gln
             20                  25                  30
Leu Gly Pro Val Thr Gln Glu Phe Trp Asp Asn Leu Glu Lys Glu Thr
         35                  40                  45
Glu Gly Leu Arg Gln Glu Met Ser Lys Asp Leu Glu Glu Val Lys Ala
     50                  55                  60
Lys Val Gln Pro Tyr Leu Asp Asp Phe Gln Lys Lys Trp Gln Glu Glu
 65                  70                  75                  80
Met Glu Leu Tyr Arg Gln Lys Val Glu Pro Leu Arg Ala Glu Leu Gln
                 85                  90                  95
Glu Gly Ala Arg Gln Lys Leu His Glu Leu Gln Glu Lys Leu Ser Pro
            100                 105                 110
Leu Gly Glu Glu Met Arg Asp Arg Ala Arg Ala His Val Asp Ala Leu
        115                 120                 125
Arg Thr His Leu Ala Pro Tyr Ser Asp Glu Leu Arg Gln Arg Leu Ala
    130                 135                 140
Ala Arg Leu Glu Ala Leu Lys Glu Asn Gly Gly Ala Arg Leu Ala Glu
145                 150                 155                 160
Tyr His Ala Lys Ala Thr Glu His Leu Ser Thr Leu Ser Glu Lys Ala
                165                 170                 175
Lys Pro Ala Leu Glu Asp Leu Arg Gln Gly Leu Leu Pro Val Leu Glu
            180                 185                 190
Ser Phe Lys Val Ser Phe Leu Ser Ala Leu Glu Glu Tyr Thr Lys Lys
        195                 200                 205
Leu Asn Thr Gln Gly Thr Gly Gly Ser Gly Gly Thr Leu Lys
    210                 215                 220
Leu Leu Asp Asn Trp Asp Ser Val Thr Ser Thr Phe Ser Lys Leu Arg
225                 230                 235                 240
Glu Gln Leu Gly Pro Val Thr Gln Glu Phe Trp Asp Asn Leu Glu Lys
                245                 250                 255
Glu Thr Glu Gly Leu Arg Gln Glu Met Ser Lys Asp Leu Glu Glu Val
            260                 265                 270
Lys Ala Lys Val Gln Pro Tyr Leu Asp Asp Phe Gln Lys Lys Trp Gln
        275                 280                 285
Glu Glu Met Glu Leu Tyr Arg Gln Lys Val Glu Pro Leu Arg Ala Glu
    290                 295                 300
Leu Gln Glu Gly Ala Arg Gln Lys Leu His Glu Leu Gln Glu Lys Leu
305                 310                 315                 320
Ser Pro Leu Gly Glu Glu Met Arg Asp Arg Ala Arg Ala His Val Asp
                325                 330                 335
Ala Leu Arg Thr His Leu Ala Pro Tyr Ser Asp Glu Leu Arg Gln Arg
            340                 345                 350
Leu Ala Ala Arg Leu Glu Ala Leu Lys Glu Asn Gly Gly Ala Arg Leu
        355                 360                 365
Ala Glu Tyr His Ala Lys Ala Thr Glu His Leu Ser Thr Leu Ser Glu
    370                 375                 380
Lys Ala Lys Pro Ala Leu Glu Asp Leu Arg Gln Gly Leu Leu Pro Val
385                 390                 395                 400
Leu Glu Ser Phe Lys Val Ser Phe Leu Ser Ala Leu Glu Glu Tyr Thr
                405                 410                 415
Lys Lys Leu Asn Thr Gln
            420
```

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 20
tggagctcta ccgccagaag gtggagccct acagcgacga gct                    43

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 21
gcaagcttat tactgggtgt tgagcttctt                                   30

<210> SEQ ID NO 22
<211> LENGTH: 522
<212> TYPE: DNA
<213> ORGANISM: Artificial Sequence
<220> FEATURE:
<223> OTHER INFORMATION: Description of Artificial Sequence: Synthetic
      nucleotide sequence encoding an artificial
      peptide.

<400> SEQUENCE: 22
tataccatgg gccatcatca tcatcatcat atagaaggaa gactaaagct ccttgacaac    60
tgggacagcg tgacctccac cttcagcaag ctgcgcgaac agctcggccc tgtgacccag   120
gagttctggg ataacctgga aaaggagaca gagggcctga ggcaggagat gagcaaggat   180
ctggaggagg tgaaggccaa ggtgcagccc tacctggacg acttccagaa gaagtggcag   240
gaggagatgg agctctaccg ccagaaggtg agccctaca gcgacgagct gcgccagcgc   300
ttggccgcgc gccttgaggc tctcaaggag aacggcggcg ccagactggc cgagtaccac   360
gccaaggcca ccgagcatct gagcacgctc agcgagaagg ccaaacccgc gctcgaggac   420
ctccgccaag gcctgctgcc cgtgctggag agcttcaagg tcagcttcct gagcgctctc   480
gaggagtaca ctaagaagct caacacccag taataagctt gc                     522

<210> SEQ ID NO 23
<211> LENGTH: 168
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu

```
            65                  70                  75                  80
Met Glu Leu Tyr Arg Gln Lys Val Glu Pro Tyr Ser Asp Glu Leu Arg
                85                  90                  95

Gln Arg Leu Ala Ala Arg Leu Glu Ala Leu Lys Glu Asn Gly Gly Ala
            100                 105                 110

Arg Leu Ala Glu Tyr His Ala Lys Ala Thr Glu His Leu Ser Thr Leu
        115                 120                 125

Ser Glu Lys Ala Lys Pro Ala Leu Glu Asp Leu Arg Gln Gly Leu Leu
    130                 135                 140

Pro Val Leu Glu Ser Phe Lys Val Ser Phe Leu Ser Ala Leu Glu Glu
145                 150                 155                 160

Tyr Thr Lys Lys Leu Asn Thr Gln
                165
```

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 24
cagaattcgc tagccgagta ccacgccaa                                    29

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 25
gcaagcttat tactgggtgt tgagcttctt                                   30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 26
ataccatggg ccatcatcat catcatcata                                   30

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 27
cagaattcgc tagcctggcg ctcaacttct ctt                               33

<210> SEQ ID NO 28
<211> LENGTH: 522
<212> TYPE: DNA
<213> ORGANISM: Artificial Sequence
<220> FEATURE:
<223> OTHER INFORMATION: Description of Artificial Sequence: Synthetic -continued nucleotide sequence encoding an artificial
peptide.

<400> SEQUENCE: 28

| tataccatgg gccatcatca tcatcatcat atagaaggaa gactaaagct ccttgacaac | 60 |
| tgggacagcg tgacctccac cttcagcaag ctgcgcgaac agctcggccc tgtgacccag | 120 |
| gagttctggg ataacctgga aaaggagaca gagggcctga ggcaggagat gagcaaggat | 180 |
| ctggaggagg tgaaggccaa ggtgcagccc tacctggacg acttccagaa gaagtggcag | 240 |
| gaggagatga gctctaccg ccagaaggtg gagccgctgc gcgcagagct ccaagagggc | 300 |
| gcgcgccaga agctgcacga gctgcaagag aagttgagcg ccaggctagc cgagtaccac | 360 |
| gccaaggcca ccgagcatct gagcacgctc agcgagaagg ccaaacccgc gctcgaggac | 420 |
| ctccgccaag gcctgctgcc cgtgctggag agcttcaagg tcagcttcct gagcgctctc | 480 |
| gaggagtaca ctaagaagct caacacccag taataagctt gc | 522 |

<210> SEQ ID NO 29
<211> LENGTH: 168
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Ala
            100                 105                 110

Arg Leu Ala Glu Tyr His Ala Lys Ala Thr Glu His Leu Ser Thr Leu
        115                 120                 125

Ser Glu Lys Ala Lys Pro Ala Leu Glu Asp Leu Arg Gln Gly Leu Leu
    130                 135                 140

Pro Val Leu Glu Ser Phe Lys Val Ser Phe Leu Ser Ala Leu Glu Glu
145                 150                 155                 160

Tyr Thr Lys Lys Leu Asn Thr Gln
                165

<210> SEQ ID NO 30
<211> LENGTH: 77
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 30

| taccatgggt catcatcatc atcatcacat tgagggacgt ctgaagctgt tggacaattg | 60 |

```
ggactctgtt acgtcta                                              77

<210> SEQ ID NO 31
<211> LENGTH: 62
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 31
aggaattctg ggacaacctg gaaaagaaa ccgagggact gcgtcaggaa atgtccaaag   60
at                                                               62

<210> SEQ ID NO 32
<211> LENGTH: 54
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 32
tatctagatg actttcagaa aaaatggcag gaagagatgg aattatatcg tcaa        54

<210> SEQ ID NO 33
<211> LENGTH: 73
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 33
atgagctcca agagaagctc agcccattag gcgaagaaat gcgcgatcgc gcccgtgcac   60
atgttgatgc act                                                     73

<210> SEQ ID NO 34
<211> LENGTH: 65
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 34
gtctcgaggc gctgaaagaa aacggggtg cccgcttggc tgagtaccac gcgaaagcga   60
cagaa                                                              65

<210> SEQ ID NO 35
<211> LENGTH: 56
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 35
gaagatctac gccagggctt attgcctgtt cttgagagct ttaaagtcag ttttct      56

<210> SEQ ID NO 36
<211> LENGTH: 61
<212> TYPE: DNA
<213> ORGANISM: Artificial Sequence
```

```
<220> FEATURE:
<223> OTHER INFORMATION: Description of Artificial Sequence: Synthetic
      nucleotide

<400> SEQUENCE: 36
cagaattcct gcgtcacggg gcccagttgt tcgcgaagtt tactgaaggt agacgtaaca    60
g                                                                    61

<210> SEQ ID NO 37
<211> LENGTH: 55
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 37
tcatctagat atggctgaac cttggccttc acctcttcta aatctttgga cattt         55

<210> SEQ ID NO 38
<211> LENGTH: 80
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 38
tggagctcat ggagtttttg gcgtgccccc tcttgcagtt ccgcacgcag cggttccacc    60
ttttgacgat ataattccat                                                80

<210> SEQ ID NO 39
<211> LENGTH: 76
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 39
gcctcgagac gtgcggccaa acgctggcga agttcatccg aatacggcgc caaatgagtc    60
cggagtgcat caacat                                                    76

<210> SEQ ID NO 40
<211> LENGTH: 61
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 40
gtagatcttc cagcgccggt ttcgcttttt cgctcaaggt gctcaggtgt tctgtcgctt    60
t                                                                    61

<210> SEQ ID NO 41
<211> LENGTH: 66
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 41
```

-continued

```
ccaagcttat tactgggtat tcagctttt  agtatattct tccagagctg acagaaaact      60
gactttt                                                                 66

<210> SEQ ID NO 42
<211> LENGTH: 651
<212> TYPE: DNA
<213> ORGANISM: Artificial Sequence
<220> FEATURE:
<223> OTHER INFORMATION: Description of Artificial Sequence: Synthetic
      nucleotide

<400> SEQUENCE: 42
accatgggtc atcatcatca tcatcacatt gagggacgtc tgaagctgtt ggacaattgg      60
gactctgtta cgtctacctt cagtaaaact cgcgaacaac tgggccccgt gacgcaggaa     120
ttctgggaca acctggaaaa agaaaccgag ggactgcgtc aggaaatgtc caaagattta     180
gaagaggtga aggccaaggt tcagccatat ctagatgact ttcagaaaaa atggcaggaa     240
gagatggaat tatatcgtca aaaggtggaa ccgctgcgtg cggaactgca agaggggca     300 cgccaaaaac tccatgagct ccaagagaag ctcagcccat taggcgaaga aatgcgcgat     360
cgcgcccgtg cacatgttga tgcactccgg actcatttgg cgccgtattc ggatgaactt     420
cgccagcgtt tggccgcacg tctcgaggcg ctgaaagaaa acggggtgc ccgcttggct      480 gagtaccacg cgaaagcgac agaacacctg agcaccttga gcgaaaaagc gaaaccggcg     540
ctggaagatc tacgccaggg cttattgcct gttcttgaga gctttaaagt cagttttctg     600
tcagctctgg aagaatatac taaaaagctg aatacccagt aataagcttg g              651

<210> SEQ ID NO 43
<211> LENGTH: 201
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Met Gly His His His His His His Ile Glu Gly Arg Leu Lys Leu Leu
 1               5                  10                  15

Asp Asn Trp Asp Ser Val Thr Ser Thr Phe Ser Lys Leu Arg Glu Gln
                20                  25                  30

Leu Gly Pro Val Thr Gln Glu Phe Trp Asp Asn Leu Glu Lys Glu Thr
            35                  40                  45

Glu Gly Leu Arg Gln Glu Met Ser Pro Tyr Leu Asp Asp Phe Gln Lys
        50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
```

-continued

```
                165                 170                 175
Leu Pro Val Leu Glu Ser Phe Lys Val Ser Phe Leu Ser Ala Leu Glu
            180                 185                 190

Glu Tyr Thr Lys Lys Leu Asn Thr Gln
        195                 200

<210> SEQ ID NO 44
<211> LENGTH: 201
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Met Gly His His His His His Ile Glu Gly Arg Leu Lys Leu Leu
  1               5                  10                  15

Asp Asn Trp Asp Ser Val Thr Ser Thr Phe Ser Lys Leu Arg Glu Gln
             20                  25                  30

Leu Gly Pro Val Thr Gln Glu Phe Trp Asp Asn Leu Glu Lys Glu Thr
         35                  40                  45

Glu Gly Leu Arg Gln Glu Met Ser Lys Asp Leu Glu Glu Val Lys Ala
     50                  55                  60

Lys Val Gln Pro Tyr Leu Asp Asp Phe Gln Lys Lys Trp Gln Glu Glu
 65                  70                  75                  80

Met Glu Leu Tyr Arg Gln Lys Val Glu Pro Leu Arg Ala Glu Leu Gln
                 85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Val Leu Glu Ser Phe Lys Val Ser Phe Leu Ser Ala Leu Glu
            180                 185                 190

Glu Tyr Thr Lys Lys Leu Asn Thr Gln
        195                 200

<210> SEQ ID NO 45
<211> LENGTH: 392
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Met Gly His His His His His Ile Glu Gly Arg Leu Lys Leu Leu
  1               5                  10                  15

Asp Asn Trp Asp Ser Val Thr Ser Thr Phe Ser Lys Leu Arg Glu Gln
             20                  25                  30

Leu Gly Pro Val Thr Gln Glu Phe Trp Asp Asn Leu Glu Lys Glu Thr
         35                  40                  45

Glu Gly Leu Arg Gln Glu Met Ser Pro Tyr Leu Asp Asp Phe Gln Lys
```

```
            50                  55                  60
Lys Trp Gln Glu Glu Met Glu Leu Tyr Arg Gln Lys Val Glu Pro Leu
 65                  70                  75                  80

Arg Ala Glu Leu Gln Glu Gly Ala Arg Gln Lys Leu His Glu Leu Gln
                 85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln Gly Thr Leu Lys Leu Leu Asp
        195                 200                 205

Asn Trp Asp Ser Val Thr Ser Thr Phe Ser Lys Leu Arg Glu Gln Leu
    210                 215                 220

Gly Pro Val Thr Gln Glu Phe Trp Asp Asn Leu Glu Lys Glu Thr Glu
225                 230                 235                 240

Gly Leu Arg Gln Glu Met Ser Pro Tyr Leu Asp Asp Phe Gln Lys Lys
                245                 250                 255

Trp Gln Glu Glu Met Glu Leu Tyr Arg Gln Lys Val Glu Pro Leu Arg
            260                 265                 270

Ala Glu Leu Gln Glu Gly Ala Arg Gln Lys Leu His Glu Leu Gln Glu
        275                 280                 285

Lys Leu Ser Pro Leu Gly Glu Glu Met Arg Asp Arg Ala Arg Ala His
    290                 295                 300

Val Asp Ala Leu Arg Thr His Leu Ala Pro Tyr Ser Asp Glu Leu Arg
305                 310                 315                 320

Gln Arg Leu Ala Ala Arg Leu Glu Ala Leu Lys Glu Asn Gly Gly Ala
                325                 330                 335

Arg Leu Ala Glu Tyr His Ala Lys Ala Thr Glu His Leu Ser Thr Leu
            340                 345                 350

Ser Glu Lys Ala Lys Pro Ala Leu Glu Asp Leu Arg Gln Gly Leu Leu
        355                 360                 365

Pro Val Leu Glu Ser Phe Lys Val Ser Phe Leu Ser Ala Leu Glu Glu
    370                 375                 380

Tyr Thr Lys Lys Leu Asn Thr Gln
385                 390

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: VARIANT
<222> LOCATION: (4)
<223> OTHER INFORMATION: X at position 4 is serine or threonine.

<400> SEQUENCE: 46
```

```
-continued

Gly Gly Gly Xaa
1
```

MEMBRANE SCAFFOLD PROTEINS

CROSS REFERENCE TO RELATED APPLICATIONS

This application claims benefit of U. S. Provisional Application No. 60/252,233, filed Nov. 20, 2000.

ACKNOWLEDGMENT OF FEDERAL RESEARCH SUPPORT

This invention was made, at least in part, with funding from the National Institutes of Health (Grant Nos. (R01GM31756, R01GM33775, GM63574 and 5F32GM19024). Accordingly, the United States Government has certain rights in this invention.

BACKGROUND OF THE INVENTION

The field of present invention encompasses molecular biology and membrane technology. Specifically, the present invention relates to artificial membrane scaffold proteins (MSPs), sequences encoding them, vectors and recombinant host cells, methods for recombinant production of them, and methods of using the membrane scaffold proteins to stabilize, disperse and solubilize fully or partially hydrophobic proteins such as tethered, embedded or integral membrane proteins while maintaining the biological activities of those membrane proteins or to stabilize, disperse and solubilize membrane fragments.

Several years ago we developed a new system for the study of membrane proteins by scanning probe microscopy, based on the adsorption of synthetic high density lipoprotein disks (rHDL, apo A-I) onto mica in an oriented manner (Carlson et al., 1997; Bayburt et al., 1998; Bayburt et al., 2000; Carlson et al., 2000). The diameters of the discoidal structures observed are approximately 10 nm with a height of 5.5 nanometers. The 5.5 nm high topology observed is most compatible with a single membrane bilayer epitaxially oriented on the atomically flat mica surface (Carlson et al., 1997).

Purified membrane proteins can be reconstituted into the phospholipid bilayer domain of certain such discoidal structures and studied in solution or subsequently adsorbed on a suitable surface for either atomic force microscopy or examination by spectroscopic techniques that take advantage of a surface of oriented protein-bilayer assemblies. Additionally, the underlying discoidal structures containing the membrane protein are easily recognizable and provide a point of reference for judging the quality of the sample and images. A tethered membrane protein, NADPH-cytochrome P450 reductase, was incorporated and physically studied in rHDL bilayer disks (Bayburt et al., 1998; Bayburt et al., 2000). The reductase can be incorporated into 10 nm diameter rHDL disks, those disks can be absorbed onto mica, and the catalytic domain of the reductase, which protrudes from the top of the bilayer structure, can be imaged. The incorporated enzyme is active on such a surface, with a turnover number consistent with that obtained with particulate membrane preparations. Force curve analysis has been used to estimate the height of the domain and its compressibility under the force of the AFM probe (Bayburt et al., 2000). The height of the molecule above the bilayer surface corresponds to the predicted height based on the recent X-ray crystal structure (Wang et al., 1997). Cytochrome P450 reductase can be incorporated in active form in MSP-supported nanoscale structures of the present invention.

High-density lipoproteins (HDL) are assemblies of a protein component, termed apo A-I, and various phospholipids. HDL particles play an important role in mammalian cholesterol homeostasis by acting as the primary conduit for reverse cholesterol transport (Fielding and Fielding, 1991). The function of HDL as a cholesterol transporter relies upon the activity of the HDL-associated enzyme lecithin-cholesterol acyl transferase, or LCAT (Glomset, 1968; Jonas, 1991), which mediates the insertion of cholesterol esters into HDL lipoprotein particles. Certain portions of the apo A-I protein are required for the activity of this enzyme (Holvoet et al., 1995). In addition, a part of the apo A-I protein is thought to be in a globular domain at the N-terminus, and to be responsible for interactions with cell surface receptors. One nascent form of HDL particles has been assumed to be that of a discoid based on electron microscopy of stained preparations (Forte et al., 1971). Our laboratory has confirmed this using AFM studies of synthetic forms of rHDL under aqueous conditions. This form, however, is not the predominant form in circulation in vivo. Rather, the apo A-I structure appears to have evolved to stabilize a spherical form.

Two general models for the structure of HDL disks have been proposed. One model has the apo A-I protein surrounding a circular bilayer section as a horizontal band or "belt" composed of a curving segmented alpha helical rod (Wlodawer et al., 1979). The other model has the protein traversing the edges of the bilayer vertically in a series of alpha helical segments (Boguski et al., 1986). Both models are based primarily on indirect experimental evidence, and no definitive means of distinguishing between them has emerged. Sequence analysis of the apo A-I genes suggests that the protein folds into a series of helices roughly 22 amino acids long, which is consistent with roughly a bilayer thickness. The placement of the helices in the disks has been predicted by computer modeling (Phillips et al., 1997) and attenuated total reflectance infrared spectroscopic measurements (Wald et al., 1990). These efforts suggested the helices lie roughly parallel to the acyl chains and are slightly shorter than the thickness of a bilayer. This arrangement of proteins and lipid is consistent with the picket fence model.

A belt model is consistent with some electron microscopy and neutron scattering data (Wlodawer et al., 1979), where the helices are arranged longitudinally around the edge of the bilayer disks like a "belt". More recent infrared spectroscopy studies using a new method of sample orientation for dichroism measurements are more consistent with the belt model, in contrast to earlier studies (Wald et al., 1990; Koppaka et al., 1999). So far, there is no compelling direct evidence as to which model is correct, even though a low resolution x-ray crystal structure for apo A-I crystallized without lipid (Borhani et al., 1997) has been obtained. The low resolution crystal structure of an N-terminally truncated apo A-I shows a unit cell containing a tetrameric species composed of 4 helical rods which bend into a horseshoe shape and which combine to give a circular aggregate about 125×80×40 Å. It was suggested that a dimeric species in this belt conformation is capable of forming discoidal particles.

The information collected to date concerning the reverse cholesterol transport cycle and the maturation of HDL particles suggests that the apo A-I protein has unique properties that allow it to interact spontaneously with membranes resulting in the formation of lipoprotein particles. Initial apo A-I lipid binding events have been proposed (Rogers et al., 1998), but conversion of bilayer-associated forms to discoidal particles remains unclear. The available evidence suggests that the energy of stabilization of lipid-free apo A-I is fairly low and that there is an equilibrium between two conformers (Atkinson and Small, 1986; Rogers et al., 1998). One conformer may be a long helical rod, and the other may be a helical "hairpin" structure about half as long. It has been suggested that the low stabilization energy and conformational plasticity allow apo A-I to structurally reorganize when it encounters a lipid membrane, thus facilitating the structural changes that would have to take place in both the membrane and the protein to produce discreet lipoprotein particles (Rogers et al., 1998). Once these particles are formed, apo A-I may still undergo specific conformational changes that contribute to the dynamic functionality of the lipoprotein particles. All of these interactions and changes take place at the protein-lipid interface. Thus, there is little reason to believe that apo A-I itself would be ideal for generating a stable, nanometer size phospholipid bilayer.

Synthetic rHDL form spontaneously upon interaction of apo A-I with phosphatidylcholine liposomes at certain protein-lipid ratios and temperatures at or above the phase-transition temperature of the lipid (Jonas, 1986). The method of detergent dialysis of mixtures of apo A-I and phospholipid is also used to form particulate structures and affords a method of incorporating purified membrane proteins. The sizes of discoidal particles formed depend on the protein to lipid ratio of the formation mixture and reflect the diameter of the bilayer domain (Brouillette et al., 1984; Wald et al., 1990). Size classes therefore arise from the number of associated apo A-I molecules at the perimeter of the phospholipid disk. These classes have been termed LP1, LP2, LP3, and LP4 for the stoichiometry of apo A-I protein molecules per disk. Variable sizes within the LP classes also arise due to heterogeneity in the conformation of apo A-I. One aspect of the present invention is based on the ability to identify the structure responsible for this heterogeneity and eliminate it to produce a monodisperse population of disk structures. Currently, the formation of homogeneous particles larger than 10 nm diameter requires separation of the particles from a mixture of species containing from 2 to 4 associated apo A-I molecules, while 10 nm diameter particles are the major form at low apo A-I to phospholipid ratios during formation. The purity of single size classes and the ability to obtain high efficiencies of membrane protein or membrane fragment incorporation requires alteration of the apo A-I structure.

Different types of lipid aggregates are used for reconstitution and study of purified membrane proteins; these include membrane dispersions, detergent micelles and liposomes. See FIG. 1. Purified systems for biochemical and physical study require stability, which is not always inherent in some systems. Liposomes are closed spherical bilayer shells containing an aqueous interior. Reconstitution into liposomes by detergent dialysis or other methods typically results in random orientation of the protein with respect to outer and lumenal spaces. Since ligands or protein targets are usually hydrophilic or charged, they cannot pass through the liposomal bilayer as depicted in FIG. 1, although this may be advantageous in some instances. Since both sides of the liposomal bilayer are not accessible to bulk solvent, coupling effects between domains on opposite sides of the bilayer cannot be studied. Liposomes are also prone to aggregation and fusion and are usually unstable for periods of more than about a week or under certain physical manipulations, such as stopped flow or vigorous mixing. The size of liposomes obtained by extruding through defined cylindrical pore sizes polydisperse in size distribution rather than exhibiting a uniform diameter.

Liposomes also may present difficulties due to light scattering, and aggregation of membrane proteins present in the bilayer. The surface area of a liposome is relatively large ($10^5$ to $10^8$ Å2). To obtain liposomes with single membrane proteins requires a large lipid to protein molar ratio. Detergent micelles allow solubilization of membrane proteins by interaction with the membrane-embedded portion of the protein and are easy to use. Detergent micelles are dynamic and undergo structural fluctuations that promoter subunit dissociation and often present difficulty in the ability to handle proteins in dilute solutions. An excess of detergent micelles, however, is necessary to maintain the protein in a non-aggregated and soluble state. Detergents can also be mildly denaturing and often do not maintain the properties found in a phospholipid bilayer system. Specific phospholipid species are often necessary to support and modulate protein structure and function (Tocanne et al., 1994). Thus, the structure, function, and stability of detergent solubilized membrane proteins may be called into question. Since an excess of detergent micelles is needed, protein complexes can dissociate depending on protein concentration and the detergent protein ratio. By contrast, the MSP nanostructures of the present invention are more robust structurally, having a phospholipid bilayer mimetic domain of discrete size and composition and greater stability and smaller surface area than unilamellar liposomes. The disk structures allow access to both sides of the bilayer like detergents, and also provide a bilayer structure like that of liposomes.

There is a long felt need in the art for stable, defined compositions for the dispersion of membrane proteins and other hydrophobic or partially hydrophobic proteins, such that the native activities and properties of those proteins are preserved.

SUMMARY OF THE INVENTION

Membrane Scaffold Proteins (MSPs) as used herein are artificial proteins which self assemble with phospholipids and phospholipid mixtures, or in the absence of phospholipids, into nanometer size membrane bilayers. A subset of these nanometer size assemblies are discoidal in shape, and are referred to as nanodisc or nanodisk structures. These "nanoscale" particles can be from about 5 to about 500 nm, about 5 to about 100 nm or about 5 to about 50 nm in diameter. These structures comprising phospholipid and MSP preserve the overall bilayer structure of normal membranes but provide a system which is both soluble in solution and which can be assembled or affixed to a variety of surfaces. The amino acid sequences of specifically exemplified MSPs are given in SEQ ID NO:6, SEQ ID NO:9, SEQ ID NO:17, SEQ ID NO:19, SEQ ID NO:23, SEQ ID NO:29, SEQ ID NO:43, SEQ ID NO:44 and SEQ ID NO:45.

The present invention further provides the use of the nanometer scale phospholipid bilayer structures or nanodiscs formed using the MSPs of the present invention are useful for the incorporation of additional hydrophobic or partially hydrophobic protein molecules. Those additional proteins can be solubilized, for example, with the use of detergent, and the solubilized proteins can be added to a solution of MSP, with or without phospholipid(s), and the nanoscale particles self assemble so that the MSPs and the additional proteins are incorporated into a stable and soluble particle. Subsequently, any detergent can be removed by dialysis. Those proteins, found in nature in the various membrane structures of a living organism, are solubilized in the MSP supported nanobilayer or nanodisc, and the native structure and activity of the target protein are preserved in these MSP-supported structures. Besides hydrophobic or partially hydrophobic proteins, membrane fragments or disrupted membranes can be assembled with the MSPs of the present invention.

The MSP supported bilayers or nanodiscs can be used in solutions or applied to a number of surfaces, such that the native structure and ligand binding of the natural protein incorporated in the MSP supported structure are maintained. As specifically exemplified, the MSP supported structures are affixed to a gold surface, e.g., for use in surface plasmon resonance technologies.

The present invention relates to methods for the incorporation of integral membrane proteins into nanoscale lipid bilayers or nanodiscs comprising at least one MSP of the present invention. Three classes of membrane proteins (tethered, embedded. and integral) can be used in the methods of the present invention. The first membrane protein class is the tethered; this class is exemplified by NADPH-cytochrome P450 reductase and human tissue factor. Examples of embedded membrane proteins include, without limitation, cytochrome P450 2B4 from rabbit liver microsomes, cytochrome P450 3A4 from human liver microsomes and cytochrome P450 6B1 from insect microsomes. The integral membrane proteins are exemplified by the 7-helix transmembrane proteins, including, but not limited to, bacteriorhodopsin from *Halobacterium halobium*, the 5-hydroxy tryptamine 1A G-protein coupled receptor from *Homo sapiens* and other G-protein coupled protein receptors. Members of each class of membrane protein have been successfully incorporated into the nanoscale structures using the MSPs and methods of the present invention. In particular, cell surface receptors, and especially G-protein coupled receptors, can be incorporated into nanobilayer bilayer structures formed from a class of membrane scaffold proteins (MSPs).

We developed nanodiscs for use in structural, biochemical and pharmaceutical techniques by engineering the scaffold protein (MSP) for greater stability, size homogeneity and useful functionalities in the resultant nanoscale lipoprotein particle. These particles can form tags for purification and physical manipulation of disks such as in hydrogels or on a gold biosensor surface, and they can serve as entities for rapid and reproducible assay and crystallization. The nanoparticles and membrane protein scaffolds are useful in biotechnology, the pharmaceutical industry as well as in basic research. In addition, the structural and functional principles uncovered through our discovery and the related techniques facilitate understanding the interactions of proteins with lipid bilayers at the molecular level.

Another aspect of this invention relates to a class of membrane scaffold protein (MSP) that can be used to solubilize membrane proteins and complexes in a functionally stable monodisperse phospholipid-bilayer associated form. Furthermore, this MSP provides means of physical manipulation of single membrane proteins. The MSP is modeled after human apolipoprotein A-I, which under certain conditions, can self-assemble with phospholipid to form discoidal structures having diameters of 100 to 200 Å (Brouillette et al., 1984). Other amphipathic proteins could also have served as a starting point. Although apoprotein A-I was known, it has not been used in any general method to solubilize and study tethered, embedded or integral membrane proteins of completely unrelated origin. A specific embodiment of this invention is the use of lipid-associated MSPs for the solubilization, manipulation and study of membrane proteins.

The present invention further provides materials and methods using genetically engineered MSPs to minimize the size of the MSP with respect to membrane particle formation and to increase the stability and monodispersity of the self-assembled nanoparticle by altering the sequence of the parent molecule. In particular, we have developed MSPs for the study of G-protein coupled receptors. G-protein coupled receptors (GPCRS) are an important and diverse class of pharmaceutical targets in mammalian cellular membranes where they function as signal transducing elements, bind several classes of bioactive ligands and transmit information to the intracellular machinery. The artificial MSP of the present invention stabilizes and solubilizes the membrane-associated form of GPCR to allow purification and manipulation in solution or on a solid support for use in high throughput screening applications and on surfaces for surface-plasmon bio sensor and scanning-probe techniques. The artificial MSP of the present invention can be used to facilitate expression and purification of recombinant membrane proteins in soluble form.

Also within the scope of the present invention are recombinant DNA molecules which encode MSPs and host cells containing those recombinant DNA molecules which are used to produce the MSPs. MSPs encoded by these recombinant DNA molecules include those comprising amino acid sequences including, but not limited to, SEQ ID NO:6, SEQ ID NO:9, SEQ ID NO:17, SEQ ID NO:19, SEQ ID NO:23, SEQ ID NO:29, SEQ ID NO:43, SEQ ID NO:44 and SEQ ID NO:45.

BRIEF DESCRIPTION OF THE DRAWINGS

FIG. 4 presents the sequence and secondary structure prediction for the parent apo A-I molecule amino acids 8 to 243 of SEQ ID NO: 2. Stars denote helical repeat boundaries. Underlined sequence in bold represents a-helical structure, italics represent b structure and plain text represents potential turns.

FIG. 5A: MSP1 showing positions of half-repeats. Half-repeat 1 is disordered based on molecular dynamics simulation (Phillips, 1997). FIG. 5B: Hinge domain movement. FIG. 5C: Removal of half-repeats. FIG. 5D: Hinge domain replacement with helices 3 and 4. FIG. 5E: MSP2, with a tandem duplication of the sequence of MSP1. FIG. 5F: Removal of half-repeat 1 to make MSP1Δ1. FIG. 5G: Tandem repeat of MSP1Δ1 to form MSP2Δ1.

FIG. 15A: Disk-associated receptor and ligand-induced assembly of receptor-target complex on gold. FIG. 15B: Disk-associated receptor in gel matrix.

FIG. 17A shows protein stained with Coomassie blue, and FIG. 17B shows heme-specific staining. Note that the 232 kDa marker protein (catalase) also stained for heme.

DETAILED DESCRIPTION OF THE INVENTION

Abbreviations used in this application include A, Ala, Alanine; M, Met, Methionine; C, Cys, Cysteine; N, Asn, Asparagine; D, Asp, Aspartic Acid; P, Pro, Proline; E, Glu, Glutamic Acid; Q, Gln, Glutamine; F, Phe, Phenylalanine; R, Arg, Arginine; G, Gly, Glycine; S, Ser, Serine; H, His, Histidine; T, Thr, Threonine; I, Ile, Isoleucine; V, Val, Valine; K, Lys, Lysine; W, Try, Tryptophan; L, Leu, Leucine; Y, Tyr, Tyro sine; MSP, membrane scaffold protein; DPPC, dipalmitoyl phosphatidylcholine; PC, phosphatidylcholine; PS, phosphatidyl serine; BR, bacteriorhodopsin.

The simplest single-celled organisms are composed of central regions filled with an aqueous material and a variety of soluble small molecules and macromolecules. Enclosing this region is a membrane which is composed of phospholipids arranged in a bilayer structure. In more complex living cells, there are internal compartments and structures that are also enclosed by membranes. There are many protein molecules embedded or associated within these membrane structures, and these so-called membrane proteins are often the most important to determining cell functions including communication and processing of information and energy. The largest problem in studying membrane proteins is that the inside of the phospholipid bilayer is hydrophobic and the embedded or anchored part of the membrane protein is itself also hydrophobic. In isolating these membrane proteins from their native membrane environments, it is very difficult to prevent them from forming inactive aggregates. The present invention provides ways to generate a soluble nanoparticle that is itself a native-like phospholipid bilayer into which hydrophobic proteins of interest (target proteins) can be incorporated to maintain the target protein as a soluble and monodisperse entity. This is accomplished by incorporating hydrophobic proteins such as membrane proteins into nanometer scale structures.

Membrane Scaffold Proteins (MSPs) as used herein are artificial proteins which self assemble phospholipids and phospholipid mixtures into nanometer size membrane bilayers. A subset of these nanometer size assemblies are discoidal in shape, and are referred to as nano disc or nanodisc structures. These structures preserve the overall bilayer structure of normal membranes but provide a system which is both soluble in solution and which can be assembled or affixed to a variety of surfaces.

Figure 1:
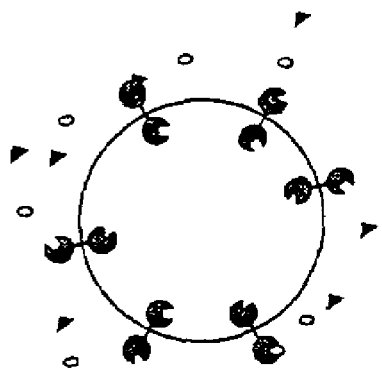
FIG. 1 schematically illustrates different types of lipid aggregates incorporating a membrane protein. Small circles and triangles represent ligand for intracellular and extracellular domains of the receptor proteins, respectively.
Figure 1:
Figure 1:
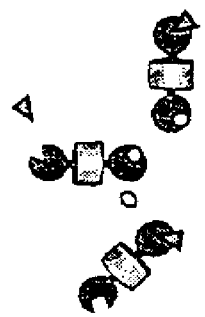
Figure 2:
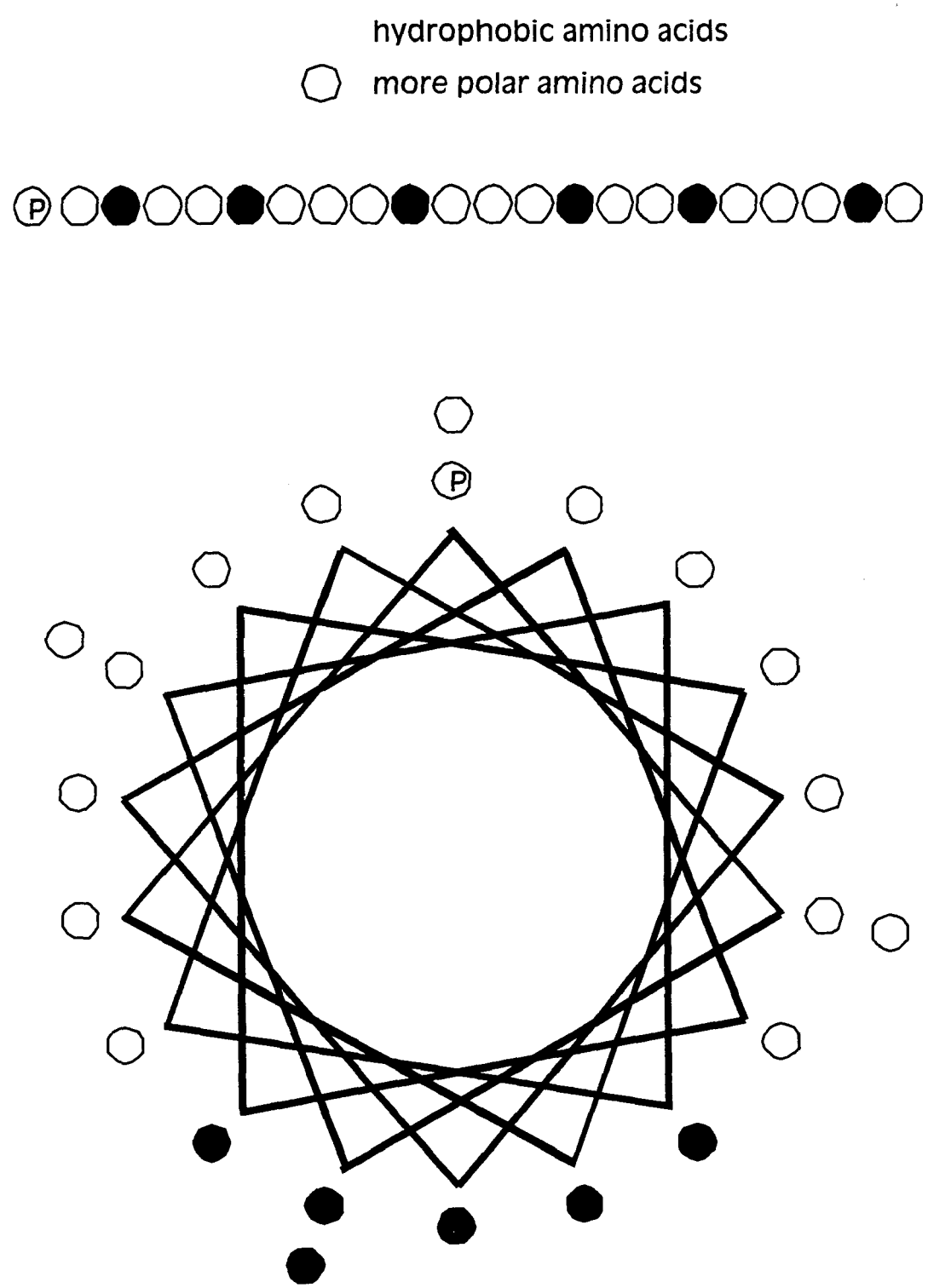
FIG. 2 shows the wheel structure of an alpha helix, with the placement of hydrophobic and hydrophilic amino acid side chains that give the helix its amphipathic character.
Figure 3A:
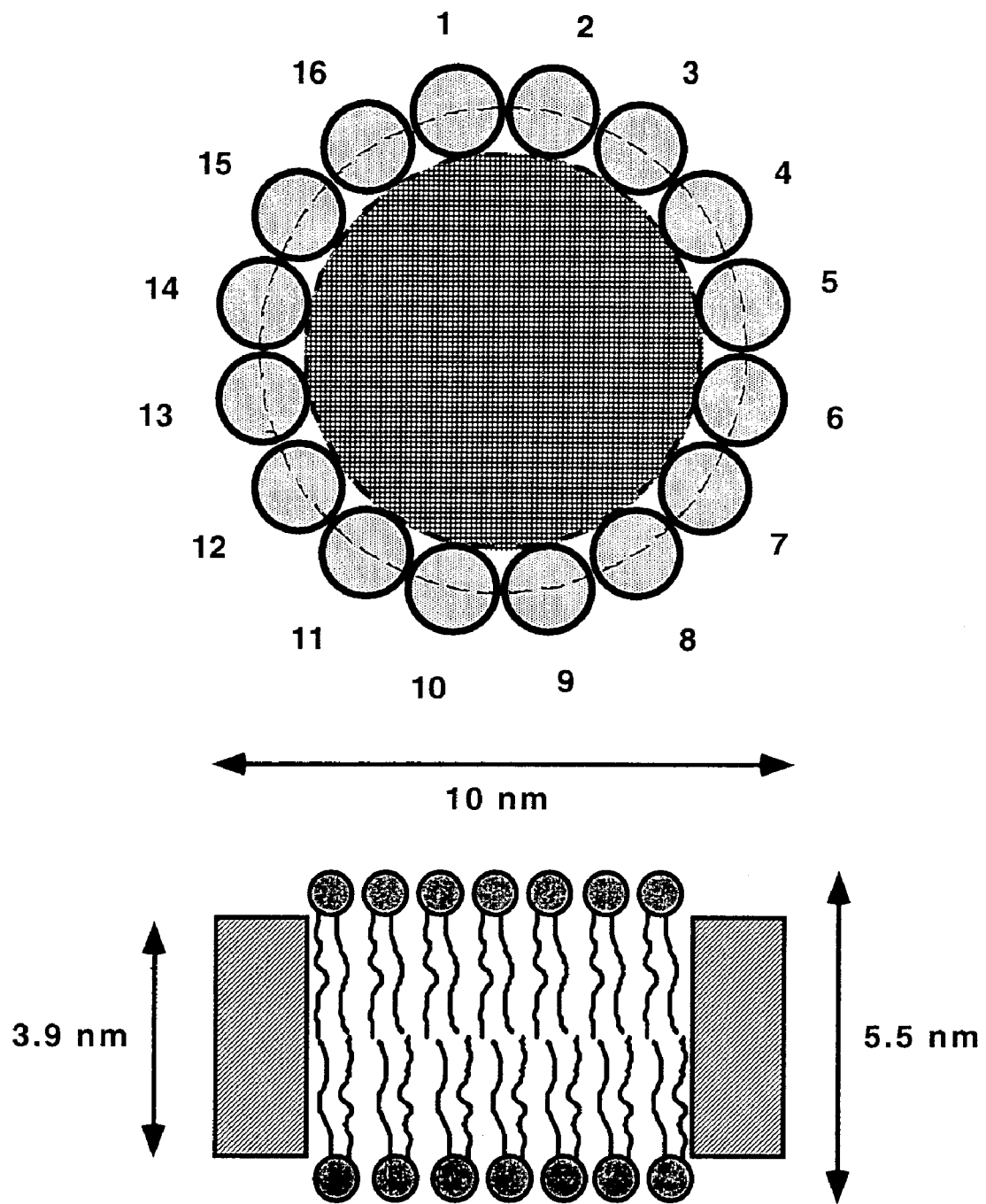
FIG. 3A is a schematic representation of a "picket fence" model for MSP stabilization of a bilayer. The circles represent single α helices with a diameter of about 1.5 nm and 0.54 nm per turn of the helix (3.6 amino acid residues per turn).
Figure 3B:
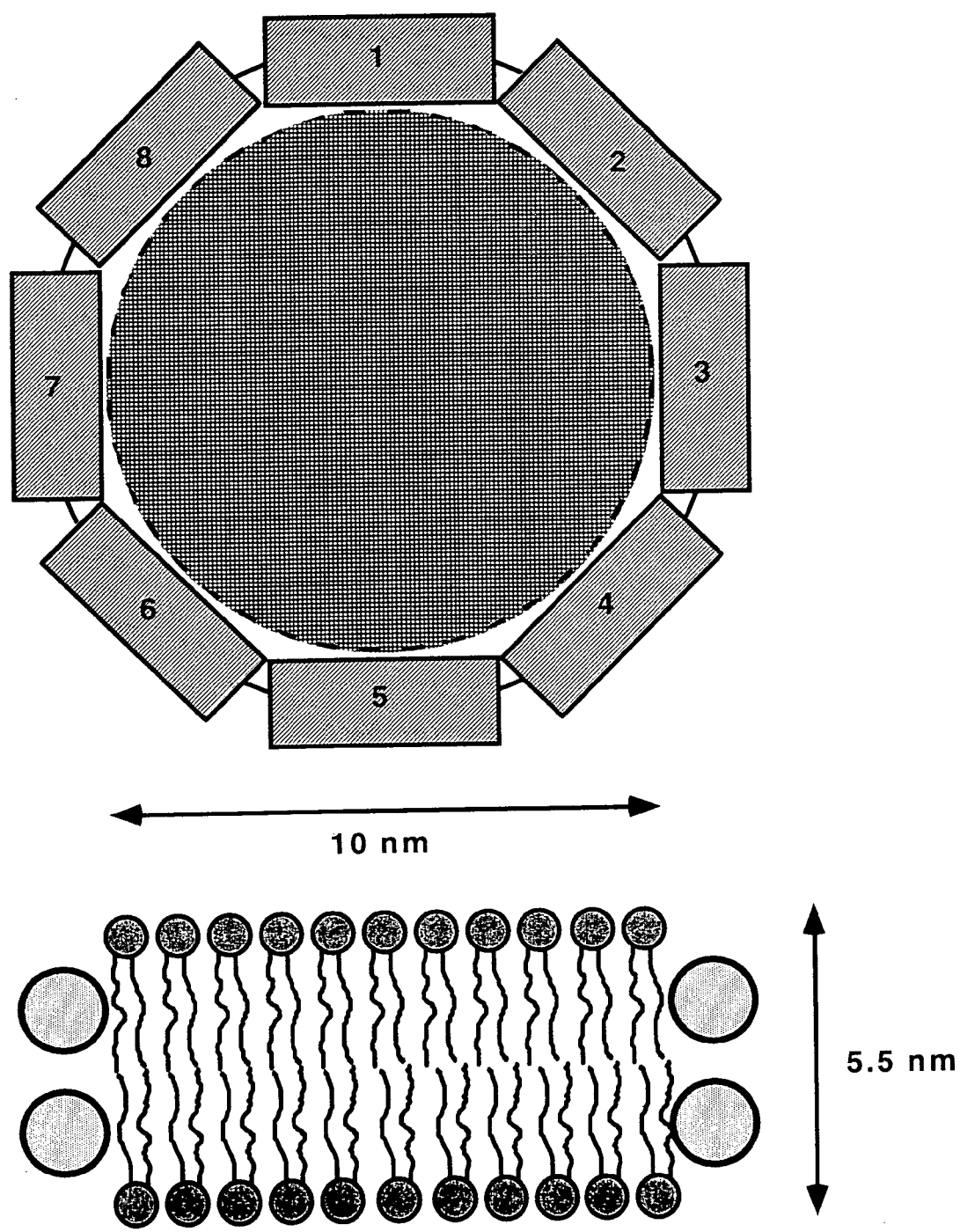
FIG. 3B is a schematic of a "belt" model of an MSP supported bilayer. The rectangles represent single α helices with a diameter of about 1.5 nm and a helix length of about 3.9 nm.

The MSPs of the present invention must be amphipathic, with one part of its structure more or less hydrophilic and facing the aqueous solvent and the other part more or less hydrophobic and facing the center of the hydrophobic bilayer that is to be stabilized. Examination of the basic biochemical literature reveals two candidates of protein structures that have this required amphipathic character: the alpha-helix and the beta-sheet. Although there are examples in the literature where beta-sheets can fold upon themselves to create a structure where the "inside" is hydrophobic and the "outside" is hydrophilic, the central cavity so formed in the simplest of these structures is small. Such a small internal region might stabilize a phospholipid bilayer, but the size would be too small to incorporate any desired membrane protein target. Hence, we designed the MSPs of the present invention to have an alpha helix as a fundamental amphipathic building block. Each MSP has an amino acid sequence which forms amphipathic α-helices with more hydrophobic residues (such as A, C, F, G, I, L, M, V, W or Y) predominantly on one face of the helix and more polar or charged residues (such as D, E, N, Q, S, T, H, K, or R) on the other face of the helix. See FIG. 2 for a schematic representation. In addition, the helical structure is punctuated with proline residues (P) about every 20–25 amino acids to form "kinks" or to initiate turns to facilitate the "wrapping" of the MSP around the edge of a discoidal phospholipid bilayer. See FIG. 2, which depicts a generalized linear amino acid sequence and a helical wheel diagram showing the placement of predominantly hydrophobic amino acids on one face of the helix. The exact amino acid sequence can vary in the positioning and number of the hydrophobic amino acids within the designed linear sequence. Simple models in which either the helical axis is parallel or perpendicular to the normal of the Nanodisc bilayer can be generated; See FIGS. 3A and 3B. To generate a disk with diameter of roughly 10 nm, an MSP comprises about 12 to about 20 or more repeating units having this generalized amphipathic sequence. Preferably, this protein would be composed of amphipathic alpha helices each with a length of between 14 and 25 amino acids, punctuated in the linear sequence by a residue unfavorable for helix formation, such as pro line, which form small helical building blocks that stabilize the hydrophobic core of the phospholipid bilayer. These small helical segments are linked together with about 1 to about 5 amino acid residues. To cover the edge of a 10 nm discoidal particle in either the "belt" or "picket fence" models presented, one would need between 10–20 such helices, with 16 being the optimal number based on the simple graphic analysis of FIGS. 3A and 3B. We thus built a synthetic gene to express a protein containing the desired amphipathic helices.

The MSPs of the present invention can be used to solubilize tethered, embedded or integral membrane proteins in nanoscale structures. Tethered membrane proteins are composed mostly of a relatively soluble globular domain external to the bilayer and relatively simple (e.g., a single pass helix) which anchors this domain to the membrane bilayer. The globular domain, in nature, can be extracellular or cytoplasmic in orientation. Embedded membrane proteins, as defined herein, are those which include a membrane anchoring segment of the polypeptide, but which also have groupings of hydrophobic amino acids on the surface of the protein, which hydrophobic domains are embedded within the membrane bilayer. Integral membrane proteins are predominantly located within the membrane bilayer; relatively small portions of the protein are exposed to an aqueous environment within the cell or to the extracellular aqueous environment.

Figures 17A, 17B:
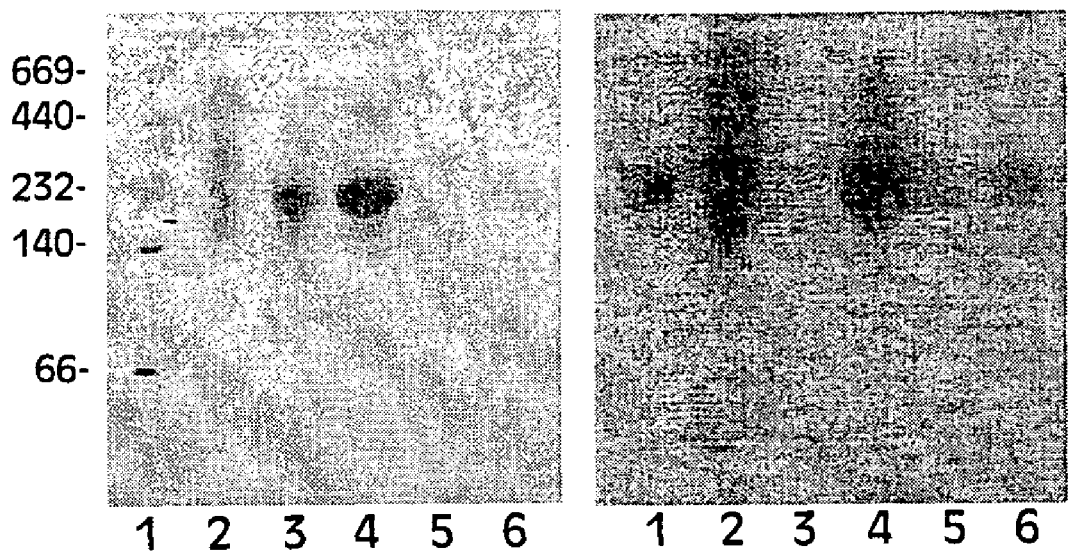
FIGS. 17A–17B illustrate thee separation of cytochrome b5 into discs as determined by native PAGE using 8–25% gradient gels. Lane 1, molecular weight markers; lane 2, cytochrome b5; lane 3, disks; lane 4, disk/cytochrome b5; lanes 5 and 6, anion exchange purified cytochrome b5 in disks representing two pools eluted from the anion exchange column.
Figure 18:
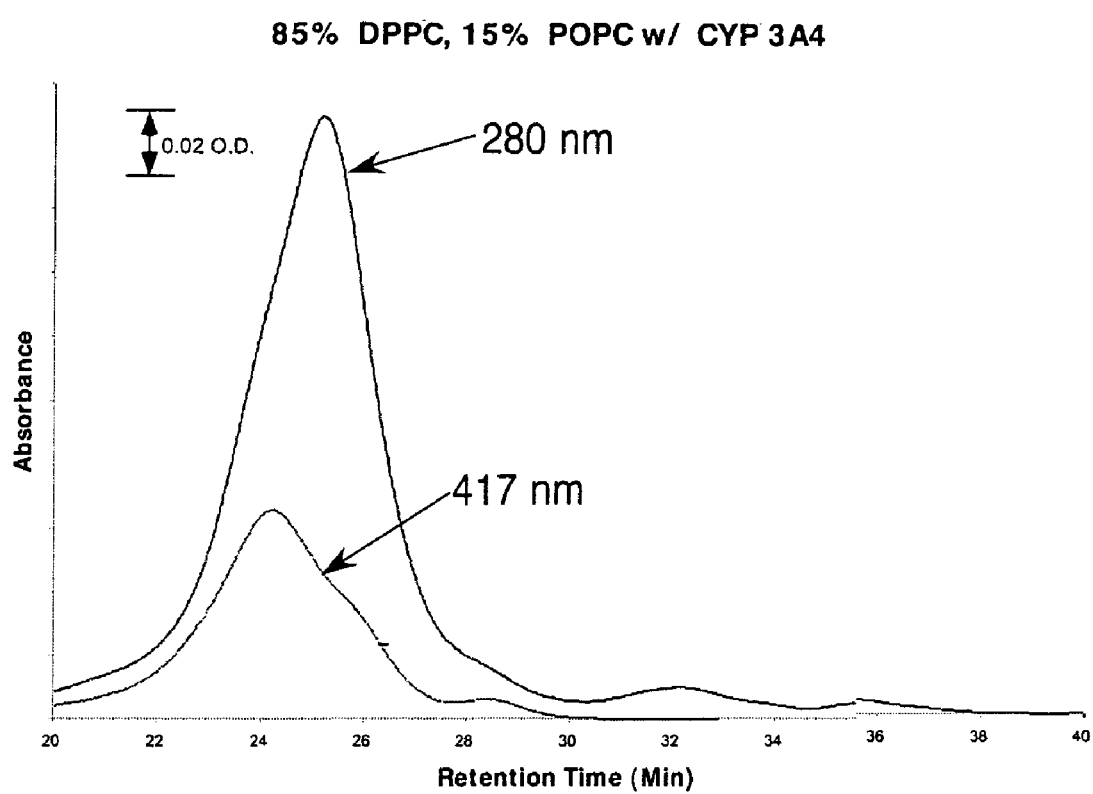
FIG. 18 is a chromatogram of cytochrome P450 3A4 incorporated into 10 nm bilayer discs consisting of 85% DPPC, 15% POPC.
Figure 19:
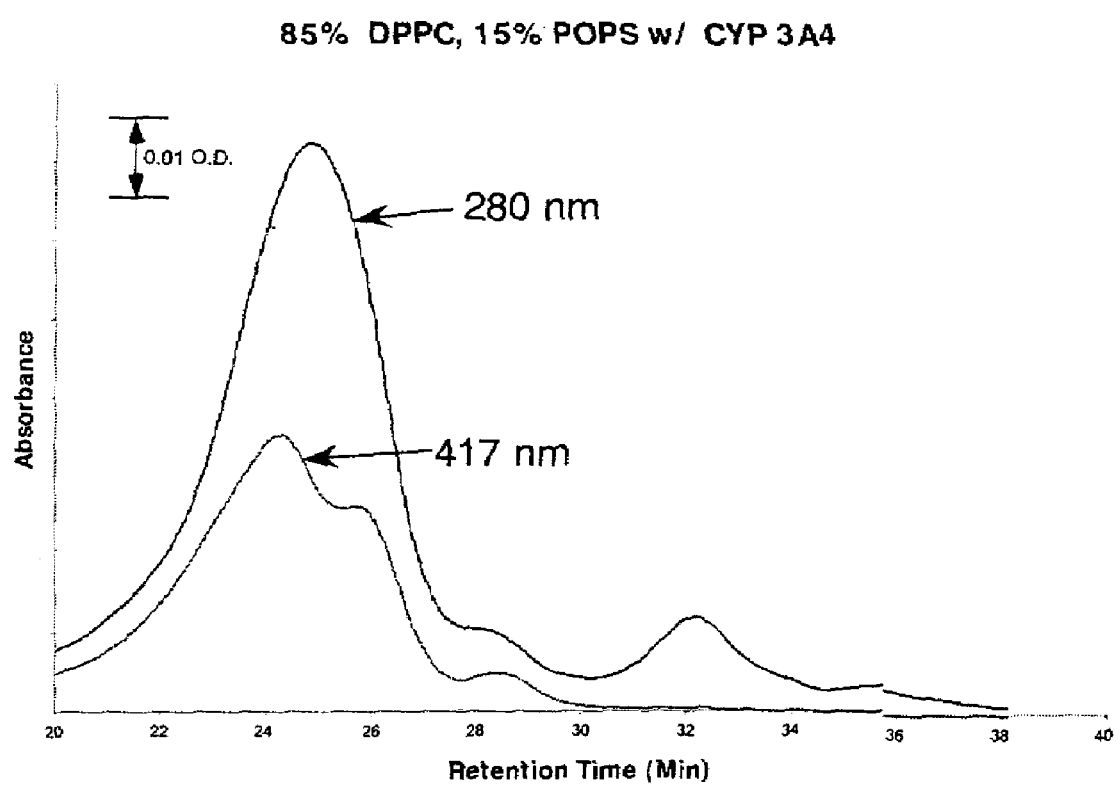
FIG. 19 is a chromatogram of cytochrome P450 3A4 incorporated into 10 nm bilayer discs consisting of 85% DPPC, 15% POPS.
Figure 20:
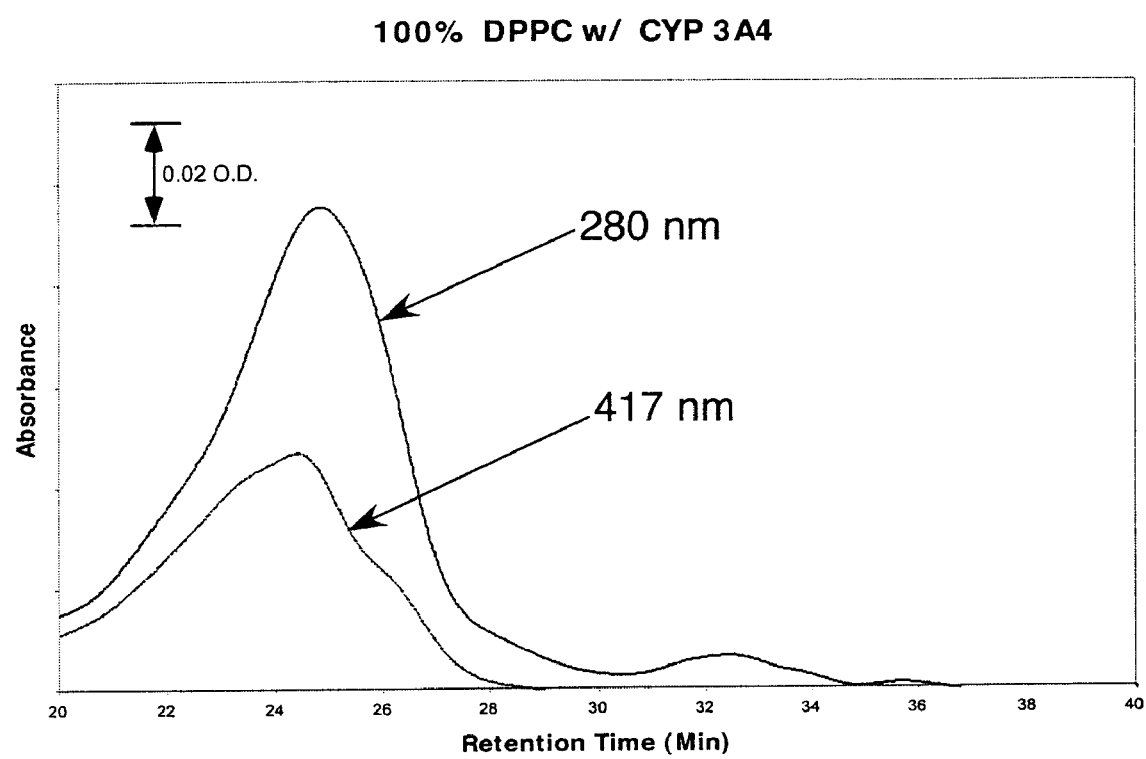
FIG. 20 is a chromatogram of cytochrome P450 3A4 incorporated into 10 nm bilayer discs consisting of 100% DPPC.

The tethered membrane protein class is exemplified by NADPH-cytochrome P450 reductase (e.g., from rat liver endoplasmic reticulum), cytochrome b5 and human tissue factor. NADPH-Cytochrome P450 reductase is a membrane protein found in the endoplasmic reticulum and catalyzes pyridine nucleotide dehydration and electron transfer to membrane bound cytochrome P450s. Isozymes of similar structure are found in humans, plants, other mammals, insects etc. Tissue factor (TF), or thromboplastin, is a 30,000 Da type-I tethered membrane protein critical to initiation of the blood coagulation cascade. This membrane-bound protein acts as an activation cofactor for factor VII, the soluble serine protease which carries out the first enzymatic step in blood coagulation. Expression of tissue factor is limited to cells that are not in direct contact with blood plasma, forming a "hemostatic envelope" around vasculature and the entire organism. High levels of TF are found in the skin, brain, and the adventital layer which surrounds blood vessels. The TF:VII complex must be assembled on a membrane surface to exhibit high activity, and optimal activity is seen only when the membrane contains phospholipids with negatively charged headgroups. Cytochrome b5 is a membrane-anchored (tethered) heme protein having a single membrane anchor domain that penetrates the membrane bilayer. Cytochrome b5 solubilized from its native membrane exists as large aggregates in the absence of detergent and appears as a smear rather than a discrete band on native polyacrylamide gel electrophoresis (PAGE) (FIG. 17, lane 2). Formation of Nanodiscs through the self-assembly process using MSPs taught in our invention, wherein cytochrome b5 is added to the preparation of MSP and phospholipid results in incorporation of cytochrome b5 into disk-sized structures (lane 4 of FIG. 17). This is verified by the intense heme-staining of the band corresponding to Nanodiscs in the right panel. Cytochrome b5-containing Nanodiscs separated by anion-exchange chromatography are shown in lanes 5 and 6 of FIG. 17. Two peaks elute from the anion exchange column near 310 mM NaCl and near 370 mM NaCl. Disks alone were observed to elute near 310 mM NaCl and cytochrome b5 alone to elute between 450 and 700 mM NaCl. This data demonstrates that cytochrome b5 is solubilized using the MSP technology and that disk complexes containing cytochrome b5 can be chromatographically separated and purified from undesired aggregated material. The optical absorption properties of the heme chromophore of the purified material show that the heme active site is in a native conformation.

Figure 21:
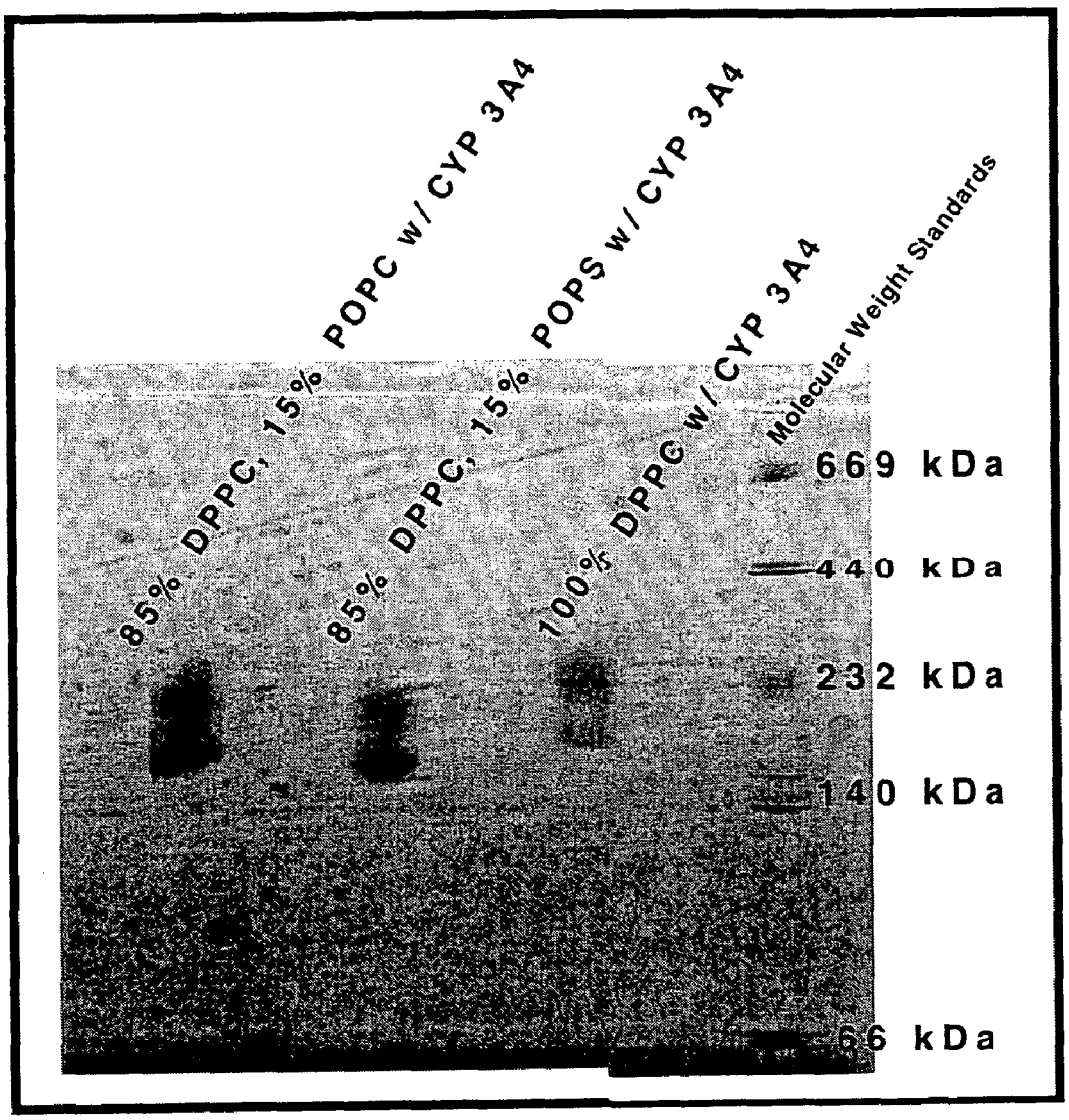
FIG. 21 shows the results of PAGE over an 8–25% gradient gel with three disc samples which correlate with the sizes of the nanodisc particles.

Examples of embedded membrane proteins include, without limitation, cytochrome P450 2B4 from rabbit liver microsomes, cytochrome P450 3A4 from human liver microsomes and cytochrome P450 6B1 from insect microsomes. The cytochromes P450 are a superfamily of enzymes that are found in all forms of life. One role of many mammalian P450s is to detoxify xenobiotics; for instance, human liver P450s detoxify most endogenous and exogenous compounds, and these enzymes determine the mean plasma lifetime of all drugs ingested. One of the most widely studied human liver cytochrome P45s is cytochrome P450 3A4 (CYP 3A4). This membrane bound P450 is the most highly expressed P450 in human liver and is responsible for metabolizing almost 50% of all pharmaceuticals (Guengerich, F. P., *Cytochrome P*450. Cytochrome P450, ed. P. R. Ortiz de Montellano. 1995, New York: Plenum Press. 473–535.) In order to demonstrate the utility of Nanodisc technology for the study of the cytochromes P450, we incorporated CYP 3A4 into MSP supported nanobilayer discs. FIGS. 18–21 show that the retention times of the CYP 3A4 (observed by optical absorbance at 417 nm) and the nanodiscs (monitored at 280 nm where both MSP and P450 absorb) elute from the column at the same time, approximately 24 minutes. This elution time also correlates closely to the calculated retention time of the disc protein complex. Further evidence that supports this is a native poly acrylamide gel electrophoresis (PAGE) that directly measures the size of eluted Nanodisc particles (FIG. 21).

Cytochrome P450 6B1 (CYP 6B1) is a member of the large cytochrome P450 monooxygenase protein superfamily, and it is another example of an embedded membrane protein. CYP 6B1 has been isolated from *Papilio polyxenes*, the black swallow tail, which feeds exclusively on plants producing furanocoumarins, plant metabolites that are phototoxic to most organisms. CYP 6B1 catalyzes the detoxification of furanocoumarins by what is believed to be an epoxidation reaction (Ma, R. et al. (1994) *Arch. Biochem. Biophys.* 310(2), 332–40). In order to show a new application of the MSP technology of the present invention, we demonstrates that isolated membranes containing their repertoire of membrane proteins can be incorporated into nanodisks comprising MSPs. A particularly important embodiment is the use of the common insect cell culture-baculovirus expression system which is used widely as a heterologous expression system. Thus, we used a commercially available Sf9 insect cell line co-infected such that a microsomal preparation containing overexpressed insect CYP 6B1 and an over-expressed insect NADPH cytochrome P450 reductase was produced. Hence, we not only demonstrated that MSP nanodiscs can be used to incorporate another cytochrome P450 system into soluble monodisperse particles but also that the source of this P450 could be simply the whole membranes from the Sf9 cell line that has been infected with a cloned CYP 6B1 gene. Thus, MSP supported nanodiscs can be produced for use in high-throughput screening ventures such as the identification of ligands for membrane-associated proteins and for the identification of new pharmaceuticals. This application can be extended to any other source of membrane fragments containing target proteins of interest, such as any mammalian cell culture system or mammalian expression system.

Figure 24:
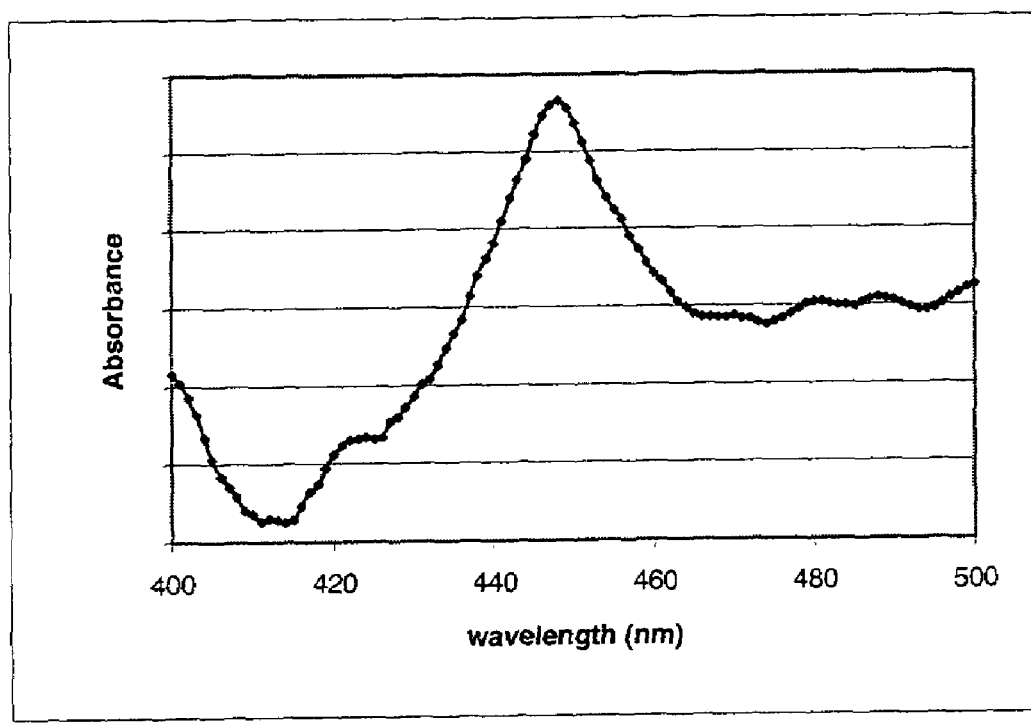
FIG. 24 provides a [$CO-Fe^{+2}-CO-Fe^{3+}$] optical difference spectrum. Active cytochrome P450 6B1 incorporated into nanodiscs absorbs at 450 nm.
Figure 25:
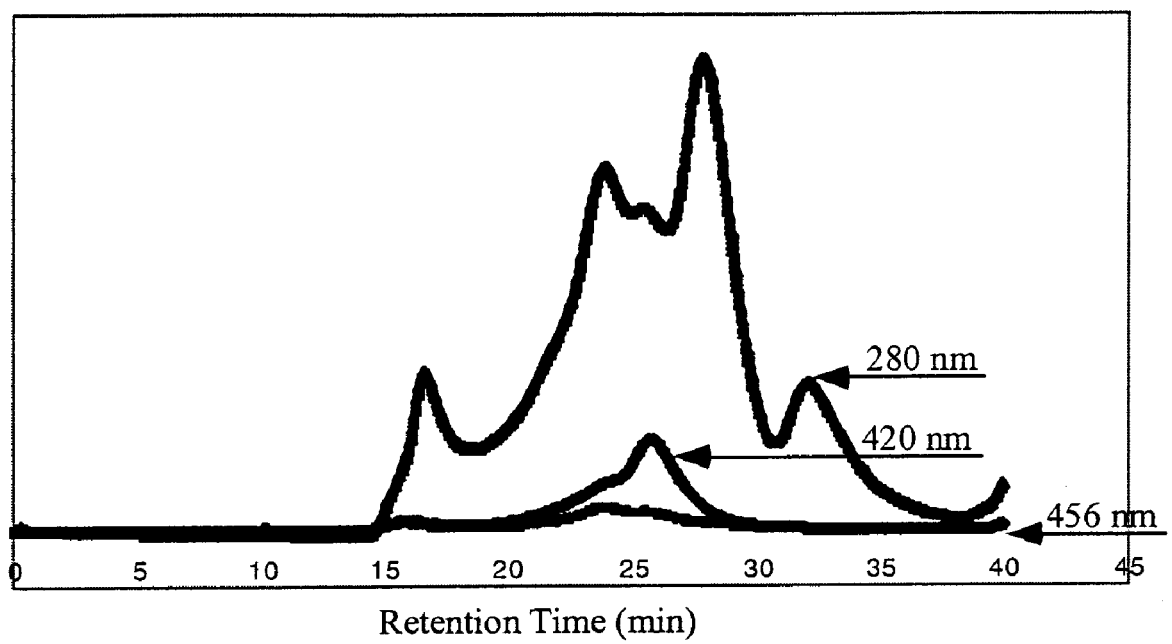
FIG. 25 depicts a chromatogram of sample separated by a Superdex sizing column. Retention times indicated rHDL particles 10 nm in size.
Figure 26:
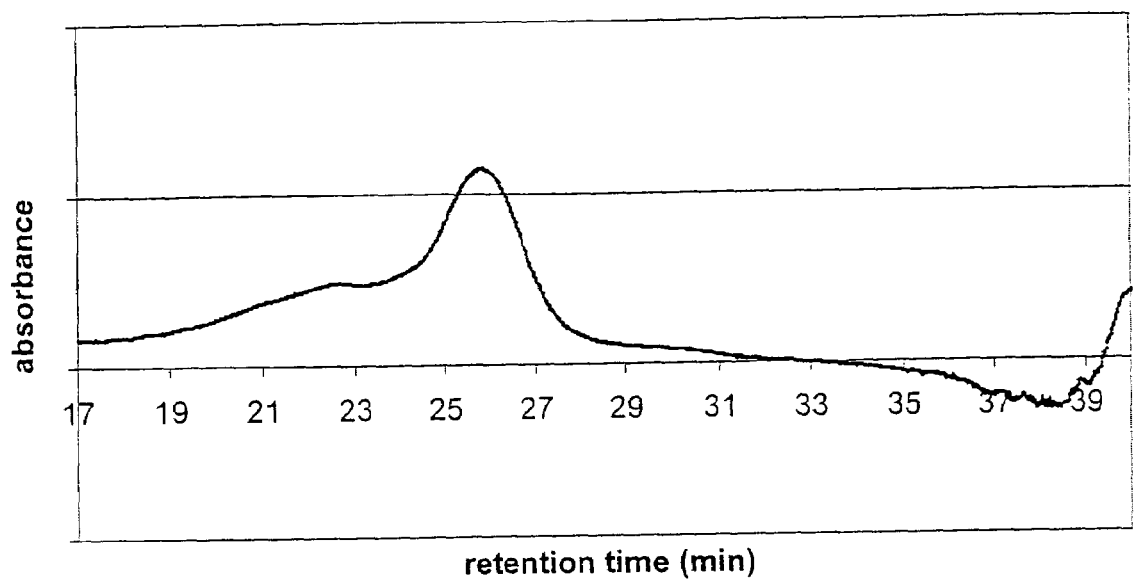
FIG. 26 illustrates co-incorporation of cytochrome P450 reductase and cytochrome P450 6B1 in MSP nanodiscs. The ratio of absorbances at 456 nm (predominantly reductase) to that at 420 nm (predominantly P450) is plotted as a function of retention time. The peak at about 26 min indicates a nanodisc population containing both reductase and cytochrome.

An important utility of the nanodisc technology of the present invention is in high throughput screening for enzymatic or receptor binding activity. In many such systems, it is advantageous to have more than one membrane protein target incorporated into the nanodiscs, for example, of the electron transfer partner needed for P450 monooxygenase catalysis or the corresponding G-protein incorporated with a G-protein coupled receptor. In order to demonstrate the utility of the MSP nanodisc technology in these situations, we successfully incorporated the NADPH cytochrome P450 reductase and a cytochrome P450 6B 1. As demonstrated herein, each target membrane protein can be individually incorporated into nanodiscs using MSPs or they can be incorporated in combinations. The endogenous relative amounts of cytochrome P450 to reductase is about 10–20 P450 molecules per reductase molecule Feyereisen, R. (1999). Annual Review of Entomology 44, 501–533). To obtain activity of CYP6B1 after reconstitution into disks, it is preferable that an excess amount of reductase be added to the reconstitution mixture, such that a P450 molecule and reductase molecule both partition into a single disk. Supplementation of the microsomal preparation with exogenously added reductase has been accomplished. The sample was separated by a Superdex sizing column, where absorbance at 280 nm indicates presence of MSP1, absorbance at 420 nm and 456 nm indicates presence of ferric species, and absorbance at 456 nm also indicates presence of reductase (FIG. 25). A ratio plot of 456 nm to 420 nm was made which showed positions on the chromatogram where the absorbance at 456 nm was above that associated with CYP6B1 and, therefore, could be attributed to absorbance by reductase (FIG. 26). Retention times correlated with the presence of 10 nanometer particles containing both CYP6B1 and reductase. See also FIGS. 22–24.

The integral membrane proteins are exemplified by the 7-helix transmembrane proteins, including, but not limited to, bacteriorhodopsin from *Halobacterium halobium*, the 5-hydroxy tryptamine 1A G-protein coupled receptor from *Homo sapiens* and other G-protein coupled protein receptors. Members of each class of membrane protein have been successfully incorporated into the nano scale structures using the MSPs and methods of the present invention. In particular, cell surface receptors, and especially G-protein coupled receptors, can be incorporated into nanobilayer bilayer structures formed from a class of membrane scaffold proteins (MSPs). BR has been incorporated into the MSP nanodiscs as described herein below, and we also used a commercially available insect cell expression system that provides a membrane fraction hosting the G-protein coupled receptor human for 5-HT-1A (serotonin). The ligand binding activity documented for 5-HT-1A incorporation into nanodiscs proves that the protein is in the active conformation in the nanodiscs of the present invention.

Figure 10:
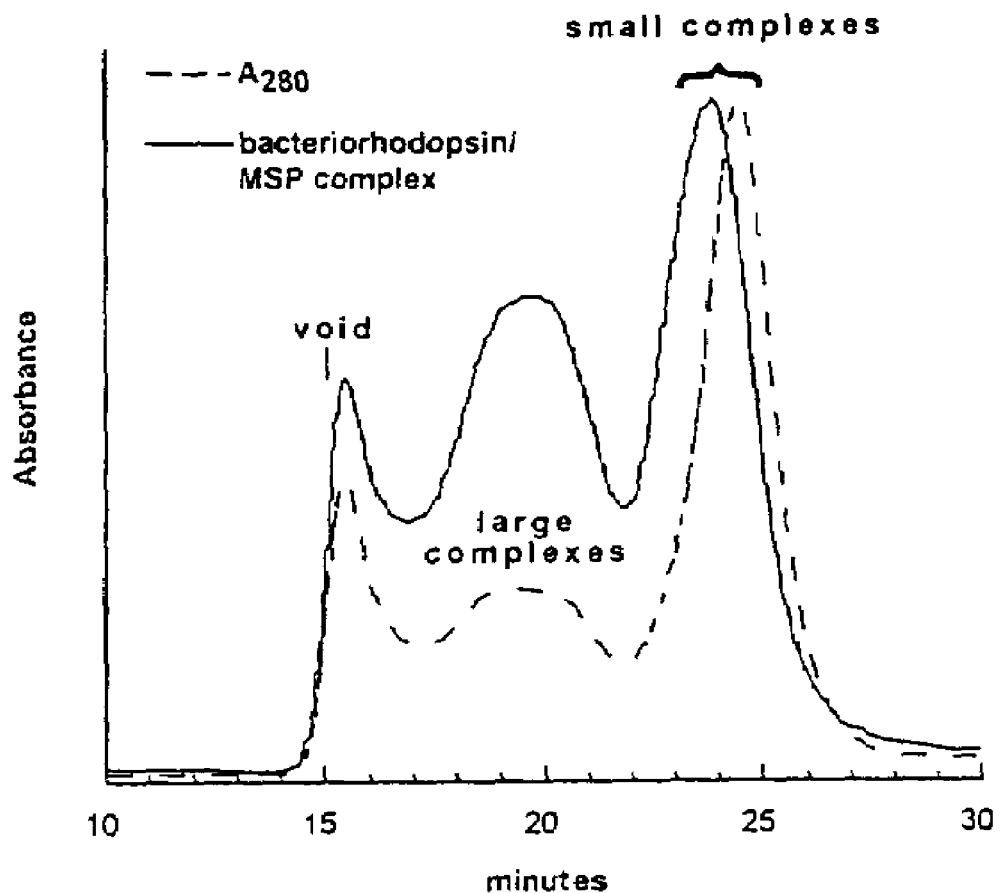
FIG. 10 provides a gel filtration elution profile of bacteriorhodopsin reconstituted into MSP1 structures.

FIG. 10, which shows a gel filtration elution profile of the MSP/BR/dimyristoyl phosphatidylcholine synthesis mixture, demonstrates that bacteriorhodopsin has been solubilized. In the absence of MSP, bacteriorhodopsin elutes quantitatively in the void fractions. A major peak of bacteriorhodopsin elutes at a position slightly earlier than the majority of MSP disks (small complexes ~100 Å in diameter, based on Stoke's radii of calibration standards). Larger complexes containing BR are also formed. The BR present in the complexes can be specifically bound to and eluted from a nickel affinity column through an engineered MSP that contains a 6His tag. In addition, the elution profile of BR in gel filtration is remarkably similar to elution profiles of MSP disks in the absence of BR. The spectrum of BR in the complexes resembles that of detergent-solubilized monomeric BR and appears unchanged for several weeks upon storage at 4° C. Surprisingly, MSP quantitatively solubilizes BR in the absence of exogenously added phospholipid. These lipid-poor complexes are also the size of small MSP/phospholipid disks.

We created an artificial MSP (MSP2) by designing a tandem repeat of MSP1 connected by a short linker to create a new molecule. See FIG. 5G and SEQ ID NO:17. Relatively large quantities (tens of milligrams/liter cell culture) of the artificial MSPs of the present invention are produced in a bacterial expression system. Our constructs reduce the number of size classes that can be formed (those corresponding to three MSP1 molecules). Preliminary evidence indicates that the sizes of major species formed with MSP2 correspond to two and four MSP1 molecules. In addition, the smallest disk sizes due to alternate conformations of membrane scaffold proteins that are found in preparations with MSP1 at low phospholipid:MSP ratios do not exist for MSP2. Without wishing to be bound by theory, we believe that the smaller particles contain a single molecule of MSP2 and the larger disks contain two molecules.

The scaffold protein (MSP) has been engineered to minimize the variability in the structure of the discoidal phospholipid bilayer entities, provide greater structural stability and increased size homogeneity of the disk structures, and to incorporate useful functionalities such as tags for purification, and physical manipulation of disks. Disk homogeneity is necessary for efficient incorporation of single membrane proteins or single membrane protein complexes into a single size class of disk. The parent molecule, apo A-I, has functions beyond disk structure stabilization; these include cellular receptor binding, LCAT activation and structural transformations between various lipoprotein species (Forte et al., 1971; Holvoet et al., 1995; Fidge, 1999). These functional regions are unnecessary and often deleterious in the artificial bilayer systems of the present invention. The artificial scaffold protein can be used in studies of amphipathic helix membrane-protein structures.

Figure 5A:
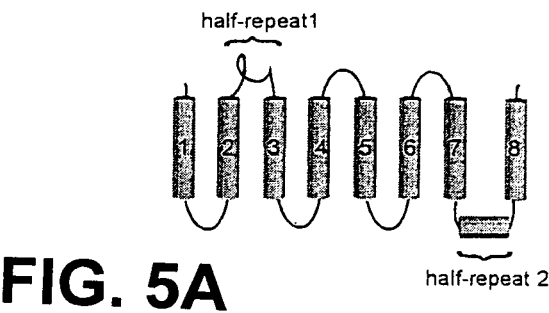
FIGS. 5A–5G illustrate various engineered MSP structures, shown with picket fence topology and helical assignments based on sequence analysis.
Figure 5B:
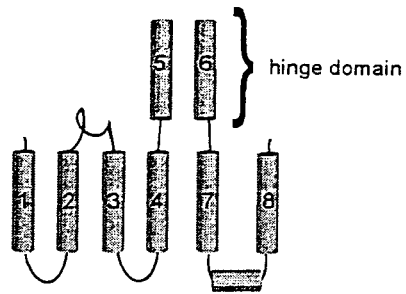
Figure 5C:
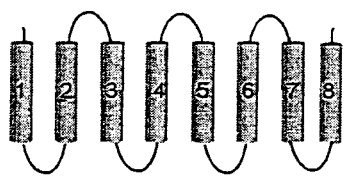
Figure 5D:
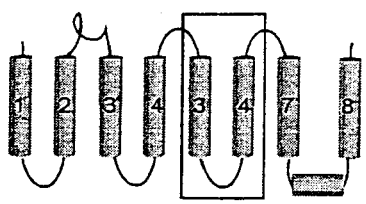
Figure 5E:
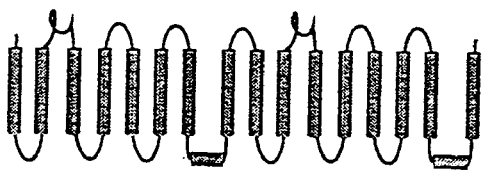
Figure 5F:
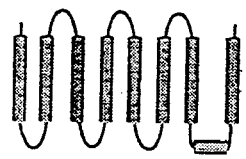

Secondary structure prediction provides a way of assessing structural features of the scaffold protein. The structure consists of mostly a-helix punctuated by prolines in the repeat sequences as shown in FIG. 4. Eight to nine alpha helices are believed to associate with lipid in the form of disks. The N-terminal region of apo A-I is predicted to be more globular in character. This portion of the molecule has been removed to produce a construct that is capable of forming disks. An MSP that produces disk assemblies with high monodispersity is desirable. The central helices (99–186) can be displaced by the lipid-free form of a related protein, apolipoprotein A-II, added to a solution of disk structures (Durbin and Jonas, 1999), and that these helices can be part of a "hinge" domain (FIGS. 5A–5B) that is dissociated from the edge of the disk, producing various particle diameters within the LP2, LP3 and LP4 classes (Jonas et al., 1989). Disk forms with dissociated hinged regions are also more susceptible to proteolysis (Dalton and Swaney, 1993), which is undesirable. The deletion of pairs of the central helices (100–143, 122–165, and 144–186) results in recombinants that form disks of smaller size than full-length apo A-I, and in addition two of the mutants (122–165 and 144–186) have increased stability to chemical denaturation (Frank et al., 1997). Further work replaced helices 5 and 6 (143–186) with another set of helices (FIG. 5D). Helices 3 and 4 contain regions that were thought to confer stability to disks (Frank et al., 1997). Helix 3 has a high lipid affinity and is believed to confer stability to the lipid-associated form through salt bridges. Helix 1 also has a high lipid affinity and is completely helical (Rogers et al., 1998). A construct which incorporates the helix 1–2 pair in place of helix pair 5–6 is desirable. The roles of the half-repeats are of great interest. These 11-mer repeats are predicted to be α-helical, but are not long enough to span the bilayer in the picket fence model. In a molecular dynamics model of the disk in the picket fence model, the region corresponding to half-repeat 1 was in fact "floppy" and did not interact with lipid, while half-repeat 2 was found parallel to the bilayer near the headgroup region (FIGS. 5A and 5C). Such structures may confer disorder to the resulting disks. To ascertain the roles of half repeats and to further optimize the MSP structure and function, mutagenesis and directed evolution were used to generate variants that are described herein below.

Receptors incorporated into MSP disks are useful in structural, biochemical and pharmaceutical research. Membrane protein study is currently limited to insoluble membrane dispersions, detergent micelles, and liposomes. Purified systems for biochemical and physical study require stability, which may or may not obtainable with detergents in many instances. Detergent micelles are dynamic and undergo structural fluctuations that promote subunit dissociation and present difficulty in the ability to handle proteins in dilute solution. The MSP nanobilayers (nanodiscs) are more robust structurally, having a phospholipid bilayer mimetic domain of discrete size and composition, and greater stability and smaller surface area than unilamellar liposomes. The particles of the present invention are stable in size and structure for at least a month at 4° C.

Signal transducing elements occur across membranes, while vesicles render one side of membrane in accessible to hydrophilic reagents and effector proteins. A specific embodiment of the present invention uses disks to stabilize pharmaceutical targets such as GPCRs, ion channels, receptor kinases, and phosphatases in a membrane-bound form on carrier particles. We have incorporated proteins with multiple spanning helices into the disks of the present invention, with a focus on GPCRs. We have successfully incorporated a model serpentine receptor, bacteriorhodopsin. Bacteriorhodopsin is a model for GPCRs, which are current targets for drug discovery. Currently, over 1000 probable G-protein receptors from various organisms have been cloned and many of the so-called "orphan" receptors await identification of natural ligands. Ligand classes include peptide hormones, eicosanoids, lipids, calcium, nucleotides, and biogenic amines. GPCRs are believed to account for more than half of currently marketed pharmaceuticals. One of ordinary skill in the art can, without undue experiment, optimize methods of incorporation of this structural class of membrane proteins. Structural characterization of the reconstituted receptors are performed using chemical analysis, spectroscopy and atomic force microscopy as described herein below.

Figure 15A:
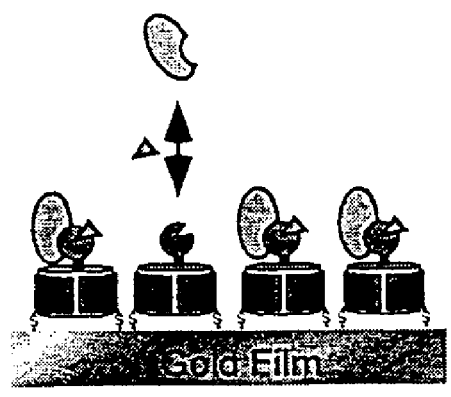
FIGS. 15A–15B show the membrane proteins incorporated into disks and attached to solid supports.

The MSPs of the present invention are used in disks to solubilize, stabilize, manipulate membrane proteins. The MSPs of the present invention, when formulated onto disks, are applicable in surface technology such as biosensor chip for high throughput screening or solid phase assay techniques. Our work on disk scaffolds has also involved surface-associated assemblies. For instance, the SPR biosensor utilizes an approximately 50 nm thick gold film on an optical component to couple surface plasmons to a dielectric component (sample) at the surface of the gold film. MSP stabilized bilayers can be attached to the surface for use as a biomimetic layer containing proteins or other targets of interest by engineering cysteines into the MSP (FIG. 15A). The use of thiols is well known for attaching molecules to gold surfaces. The placement of the cysteine depends on the model used for placement of the cysteine residue(s). Based on the belt model, cysteines can be placed along the polar side of the amphipathic helix axis, provided that a cysteine residue is not positioned at the helix—helix interface. The helix—helix interface of the belt is believed to be in register with the position of apo A-I Milano (R173C), which forms disulfide-linked dimers (Segrest et al., 1999). An alternative is to introduce cysteines within a flexible N- or C-terminal linker. Such a construct is, in theory, capable of associating either the belt or the picket fence form of disk to a gold surface. Alternatively, thiol lipids can be incorporated within the bilayer domain. In addition to SPR, surface-associated disks on gold can be used in STM and electrochemical studies, for example, such as with membrane associated redox proteins, e.g. cytochrome P450 and its flavoprotein, as well as ion channels.

SPR data can also be obtained from measurements made using a thin film of dielectric such as silicon dioxide applied over the metal film normally used as the substrate in SPR.

This variation of the technique has been termed coupled plasmon waveguide resonance (CPWR) (Salamon et al., 1997a). Because silica can be used as the active surface in these plasmon resonance experiments, the process of producing a self-assembled bilayer can be simplified to the same procedures used to produce surfaces on mica or other silicon oxide surfaces. This has the added advantage of making the conditions used for the SPR experiments directly comparable to those used for AFM experiments. The CPWR technique can easily be performed on our SPR instrument by simply adding the silica coating to the metal film slides that are presently used for SPR spectroscopy.

Figure 15B:
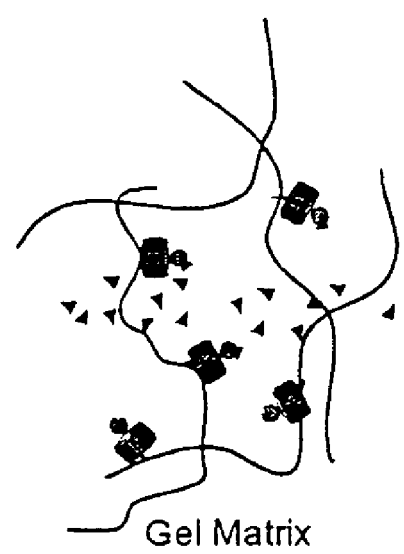

MSPs with available cysteine groups also enable specific labeling with chemically reactive groups or affinity tags for immobilization in gel matrices. Hydrogels with reactive coupling groups are useful for immobilizing proteins for SPR measurements. In the hydrogel configuration (FIG. 15B), the disk would serve as a carrier for bilayer-embedded membrane proteins in a monodisperse form with both intra- and extracellular domains available for ligand binding. We have already demonstrated that disks containing His tag bind to a metal chelate matrix which can be used to immobilize BR. This points to another use of the disk structure, i.e., in preparing affinity matrices for bioseparation processes, and measuring ligand affinities. The particles and techniques with the present invention are useful for drug discovery, structure/function correlation, and structure determination of membrane proteins.

Current limitations to structure determination of membrane proteins are the abilities to produce large amounts of membrane proteins, and to crystallize these proteins. MSPs are useful as carriers for membrane protein stabilization and expression. MSP can serve to solubilize membrane proteins for crystallization in lieu of detergents. Indeed, where the lipid bound form of MSP is structurally stable and rigid, crystallization is enhanced by introduction of crystal contacts through the MSP. We have already demonstrated that MSP1 or MSP2 can be used to solubilize BR in the presence and absence of exogenous lipid. Additional nonexemplified fusion constructs with membrane protein with an MSP region can be expressed in *Escherichia coli* using any of a number of art-known vectors. In this way, a stable and soluble form of the membrane protein that contains a membrane anchor is produced in large quantity. The exciting discovery that MSP solubilizes BR in the absence of added phospholipid allows the use of the artificial MSP to stabilize membrane proteins in the absence of detergents or lipid additives. The artificial MSPs of the present invention can be used in solubilization of BR and other membrane proteins including, but not limited to, cytochrome P450, cytochrome P450 reductase, and the 5-HT-1A receptor.

Figure 5G:
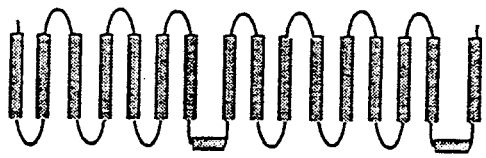

One important goal in utilizing a membrane scaffold protein (MSP) to provide membrane proteins in general, and G-protein Coupled Receptors (GPCRs) in particular, with a suitable environment for homogeneous biochemical assay or crystallization is to have a homogeneous preparation of particles. The membrane scaffold proteins we have described, ranging from full length human Apo-AI and its derivatives, to alternate membrane scaffold proteins including but not limited to, truncated human Apo-AI (t-MSP) where the amino terminal soluble domain has been removed, deletion mutants where one or more protein segments are removed and any of the above materials where a histidine tag is incorporated, primarily form 8–10 nm particles when self-assembled with phospholipids in solution. However, upon initial reconstitution, there are particles of other sizes present. While standard size separation chromatography can be used to purify a single size class of particle, it is preferable to minimize the size distribution of the initial reconstitution mixture of target protein, MSP and phospholipid. The 8–10 nm particle is nominally composed of two MSP, Apo-AI or Apo-AI derivative proteins. Hence, we constructed a membrane scaffold protein where two of the truncated Apo-AI proteins (termed MSP1) are genetically liked to form a scaffold protein composed of a single polypeptide chain. This is schematically illustrated in FIG. 5G.

GPCRs which can be solubilized in nano scale phospholipid bilayers can include the Class A (Rhodopsin-like) GPCRs, which bind amines, peptides, hormone proteins, rhodopsin, olfactory prostanoid, nucleotide-like compounds, cannabinoids, platelet activating factor, gonadotropin-releasing hormone, thyrotropin-releasing hormone and secretagogue, melatonin and lysosphingolipid and LPA. GPCRs with amine ligands include, without limitation, acetylcholine or muscarinic, adrenoceptors, dopamine, histamine, serotonin or octopamine receptors); peptide ligands include but are not limited to angiotensin, bombesin, bradykinin, anaphylatoxin, Fmet-leu-phe, interleukin-8, chemokine, cholecystokinin, endothelin, melanocortin, neuropeptide Y, neurotensin, opioid, somatostatin, tachykinin, thrombin vasopressin-like, gal anin, proteinase activated, orexin and neuropeptide FF, adrenomedullin (G10D), GPR37/endothelin B-like, chemokine receptor-like and neuromedin U.

Ligands of other specific GPCRs include hormone protein, rhodopsin, olfactory, prostanoid, nucleotide-like (adenosine, purinoceptors), cannabinoid, platelet activating factor, gonadotropin-releasing hormone, thyrotropin-releasing hormone & secretagogue, melatonin and lysosphingolipid & LPA, among others. Class B secretin-like GPCRs include, without limitation, those which bind calcitonin, corticotropin releasing factor, gastric inhibitory peptide, glucagon, growth hormone-releasing hormone, parathyroid hormone, PACAP, secretin, vasoactive intestinal polypeptide, diuretic hormone, EMR1 and latrophilin. Class C metabotropic glutamate receptors include those which bind metabotropic glutamate, extracellular calcium-sensing or GABA-B, among others. "Orphan" receptors whose ligands are not yet known are also potential targets of assays of the present invention.

In the assays of the present invention which demonstrate binding of a particular ligand or which are used to identify inhibitors or competitors of ligand binding to an MSP-supported GPCR, a variety of labels can be incorporated within the ligand molecule (such as radioactive isotope, e.g., $^3$H, $^{14}$C, $^{35}$S, $^{32}$P) or detectable compounds can be attached to the ligand molecule provided that binding to the cognate receptor is not significantly reduced due to the label. Labels can include, without limitation, $^{125}$I, $^{131}$I, fluorescent compounds, luminescent compounds, etc).

The necessary properties of the linker sequence between fused MSPs are flexibility and solubility so that the fused proteins assemble into particles in a manner similar to two separate MSP. Linker sequences consisting of repeats of Gly-Gly-Gly-Ser/Thr- (SEQ ID NO:46) have these properties. It is also desirable to minimize the length of the linker. We constructed a fusion with the minimal linker -GT-, which corresponds to the consensus DNA restriction site for Kpn I, as described herein below. The Kpn I site provides an easy way of inserting any desired linker sequence by restriction with Kpn I and insertion of double-stranded synthetic DNA encoding any desired linker (Robinson et al. 1998). We have also made a fusion construct with the linker sequence -GTGGGSGGGT- (SEQ ID NO:15). The MSP2 with the minimal linker, however, assembles into particles very similar to particles containing two MSP1 proteins.

Figure 13:
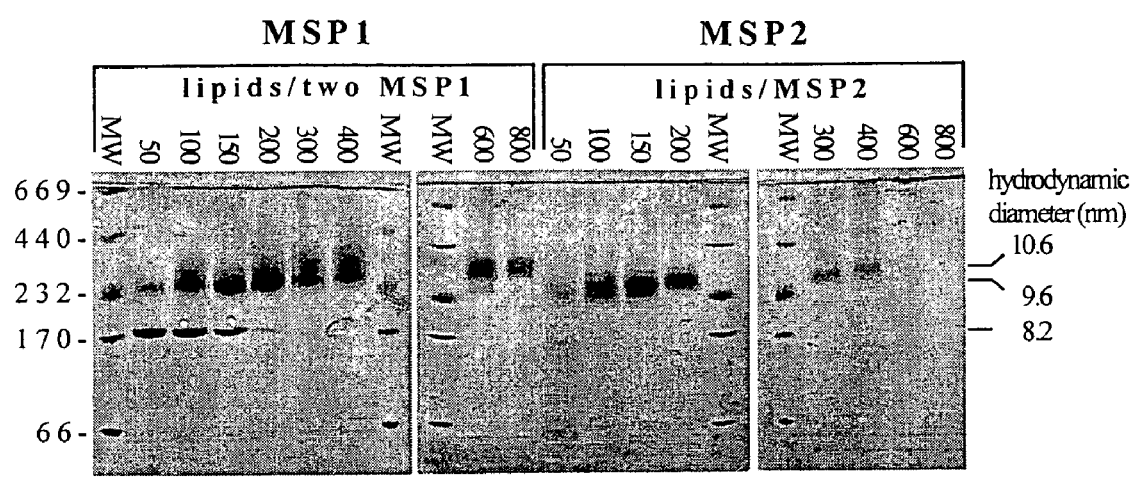
FIG. 13 illustrates nano scale particle formation with varying lipid to MSP ratios. Particles were formed at the indicated lipid to MSP mole ratio and separated by native gradient gel electrophoresis. As indicated at the right, MSP1 forms 8.2, 9.6 and 10.6 nm diameter particles. MSP2 forms predominantly 9.6 nm particles.

The complete amino acid and nucleic acid sequences for the MSP2 scaffold protein is shown in Tables 7 and 8; see also SEQ ID NO:16 and SEQ ID NO:17. The MSP2 fusion protein was expressed in *E. coli* and purified to homogeneity using basically the same procedure as described for the single MSPs. The MSP2 protein serves as an effective scaffold protein, self-assembling with phospholipid upon removal of solubilizing detergent. Addressing the point of sample heterogeneity, FIG. 13 shows densitometry traces of native gradient polyacrylamide gels with the individual peaks labeled as to mean particle diameter in Angstroms. Clearly evident, particularly at a lipid/dimer ratio of 200 corresponding to nominally 10 nm particles, is the much greater monodispersivity afforded by the MSP2 protein.

Figure 14:
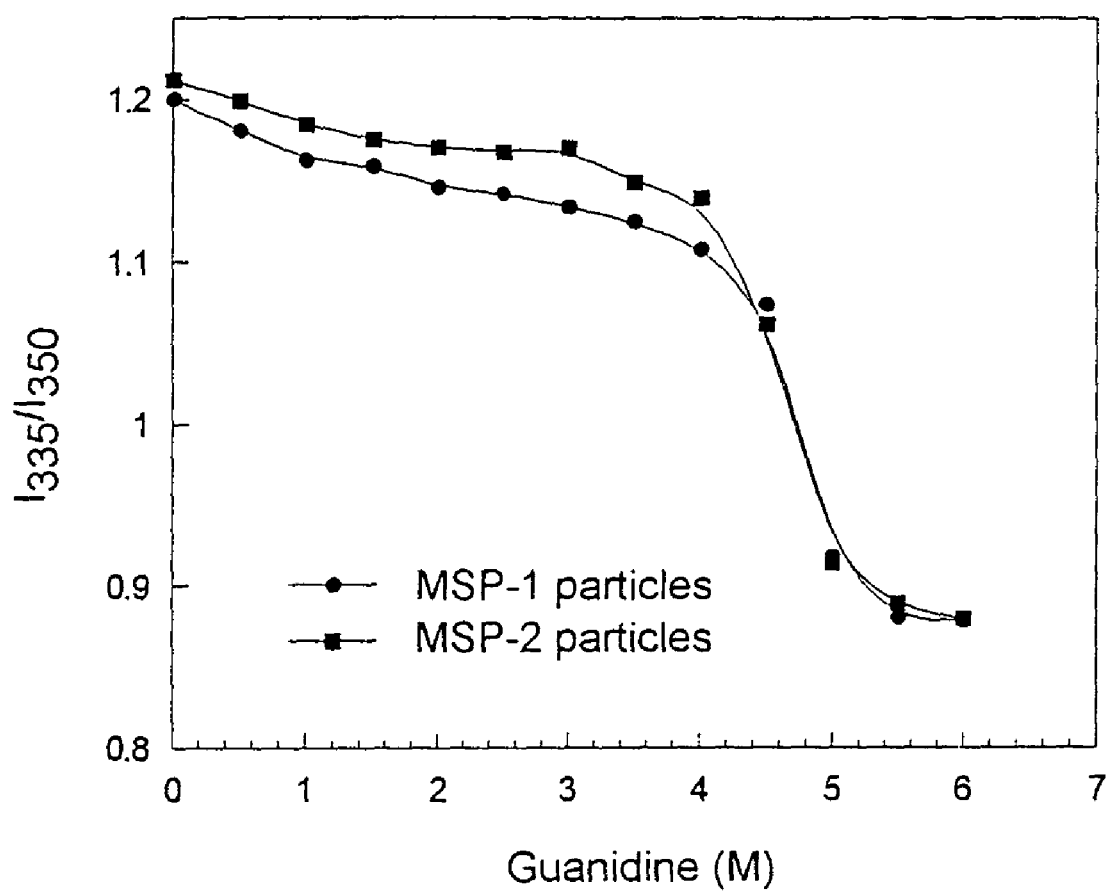
FIG. 14 shows the results of chemical denaturation of MSP1 and MSP2 particles (9 nm diameter) in complexes with dipalmitoyl phosphatidylcholine as monitored by tryptophan fluorescence. Excitation was at 280 nm, and the buffer was 10 mM Hepes pH 7.5, 0.15 M NaCl.

Importantly, the overall stability of the disks, as monitored by chemically induced unfolding and exposure of tryptophan residues to solvent, is not altered by the fusion of the monomeric membrane scaffold proteins, as shown in FIG. 14.

An important technique used in the characterization of disk structures and associated proteins is scanning probe microscopy (SPM). SPM is an umbrella term for any microscope that utilizes the scanning principles first pioneered in the scanning tunneling microscope (STM), but these microscopes can vary so greatly they are best discussed in terms of their guiding central principle. The technology has been used in the analysis of biological membranes and their associated proteins, bilayer structures and incorporated membrane proteins surfaces. SPM combines independent mobility in all three spatial directions (scanning) with a detection system capable of detecting some characteristic of the surface (probing). The various surface characteristics that can be probed (conductivity, surface forces, compressibility, capacitance, magnetic, fluorescence emission) demonstrate the wealth of information that can be obtained. The excellent z-axis sensitivity of atomic force microscopy makes the presence of proteins binding to an rHDL monolayer easily detectable, as we have shown for well characterized integral and anchored membrane proteins immobilized in MSP-supported nanodiscs (Bayburt et al., 1998). Other examples of the usefulness of the precise height measurements possible with AFM are our direct quantitation of rHDL particle height (Carlson et al., 1997), and membrane protein height measurements obtained by modulating the force of the AFM probe on various nanodisc assemblies (Bayburt et al., 2000). The surface association of disks formed from MSPs allows the utilization of the human apo A-I protein and its improved variants to directly investigate the biophysical properties of single membrane proteins incorporated into phospholipid bilayers on surfaces by SPM. The ability to attach disks to atomically flat conductive surfaces (such as gold) is necessary for scanning tunneling microscopy (STM). In theory, tunneling through a redox-active system can be used to probe the functional state of an enzyme (Friis et al., 1999; Mukhopadhyay et al., 2000). These two techniques provide complementary data and can be used in concert to create as complete a picture as possible of events occurring at the bilayer/solution interface. The ability to place disks on a gold surface also allows the use of surface plasmon resonance (SPR). Insertion of membrane proteins into such artificial lipid bilayers, or their interaction with surface-associated proteins can be detected and quantified by SPR.

Measurements of disk stabilities and determination of size dispersion among classes are necessary to evaluate the constructs that are being created. Gel filtration and native gel electrophoresis are used to separate and quantitate the different size classes. Spectroscopy is used to quantitate secondary structure (CD) and lipid association (fluorescence) characteristics of the engineered MSPs, including stabilities based on thermal and chemical denaturation. Compositions and stoichiometries of components in disks are quantitated by traditional methods (Jonas, 1986).

AFM is used to provide molecular resolution data on the structural organizations of the lipid and protein components of the systems produced. This technique can be used in air, vacuum, and under aqueous and non-aqueous fluids. The latter capability has made it the most important scanning probe technique in the biological sciences. The AFM is a very versatile instrument as it is capable of acquiring images and other forms of force data in several different modes (Sarid, 1994) such as contact, tapping, phase, and lateral force. All of these scanning modes are available on the Digital Instruments Multimode Scanning Probe Microscope (Digital Instruments, Plainview, N.Y.) and they have been successfully used to image rHDL and proteins associated with rHDL layers under biological buffers. This instrument can also be used in STM and electrochemical modes to study characteristics of gold-associated constructs and incorporated redox proteins.

As used herein, membrane scaffold proteins are proteins or polypeptides which self assemble phospholipids and phospholipid mixtures into nanometer size membrane bilayers. A subset of these structures are discoidal in shape and are referred to as nanodiscs or nanodisks. Hydrophobic proteins, e.g., membrane proteins, or membrane fragments can associate with these particles such that the hydrophobic proteins or membrane fragments are effectively solubilized in a stable structure which maintains the functionality of the protein with respect to enzymatic activity or ligand binding. These particles are stable in solution or they can be fixed to a surface, advantageously in a uniform orientation with respect to the surface. As used herein, a nanoparticle comprising MSPs (with or without another hydrophobic or a partially hydrophobic protein) can be from about 5 to about 500 nm, desirably about 5 to about 100 nm, or about 5 to about 50 nm in diameter. Nanoparticles (disks) of about 5 to about 15 nm in diameter are especially useful.

Figure 11:
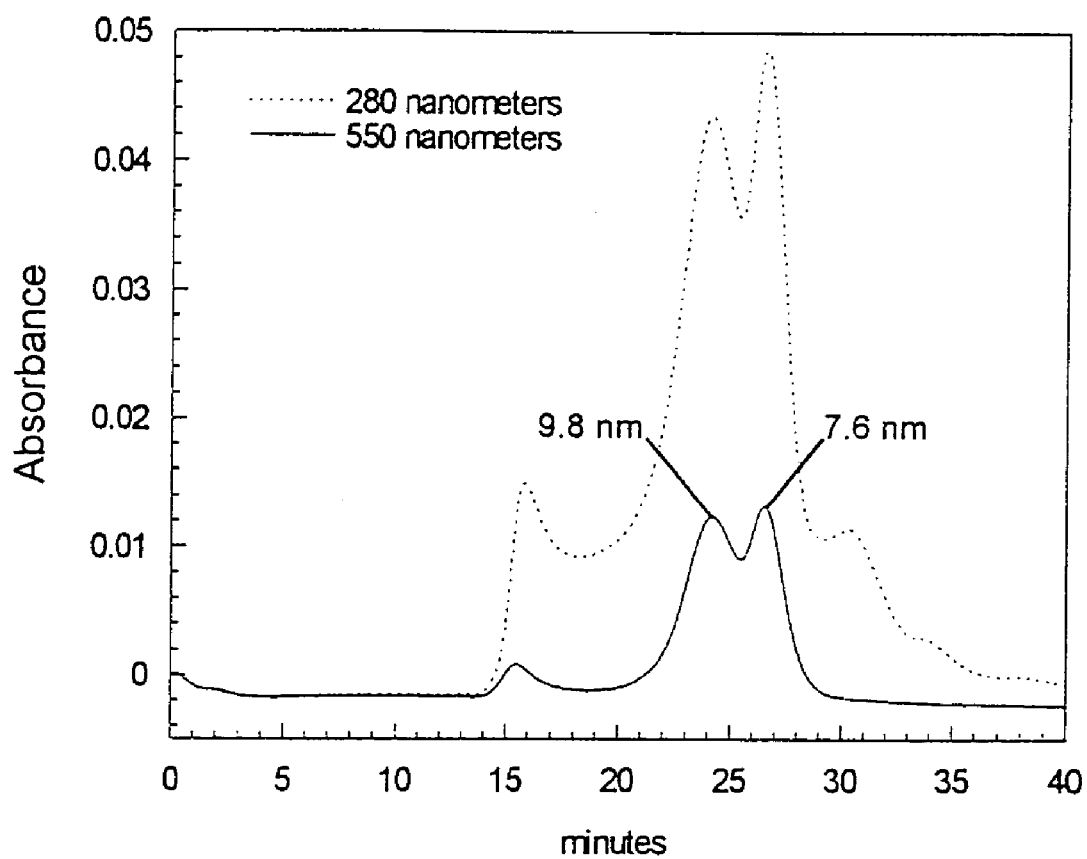
FIG. 11 show a gel filtration chromatogram of bacteriorhodopsin solubilized by MSP1 in the absence of added phospholipid. Bacteriorhodopsin is detected by absorbance at 550 nm, while MSP1 and bacteriorhodopsin protein is detected by absorbance at 280 nm.
Figure 12:
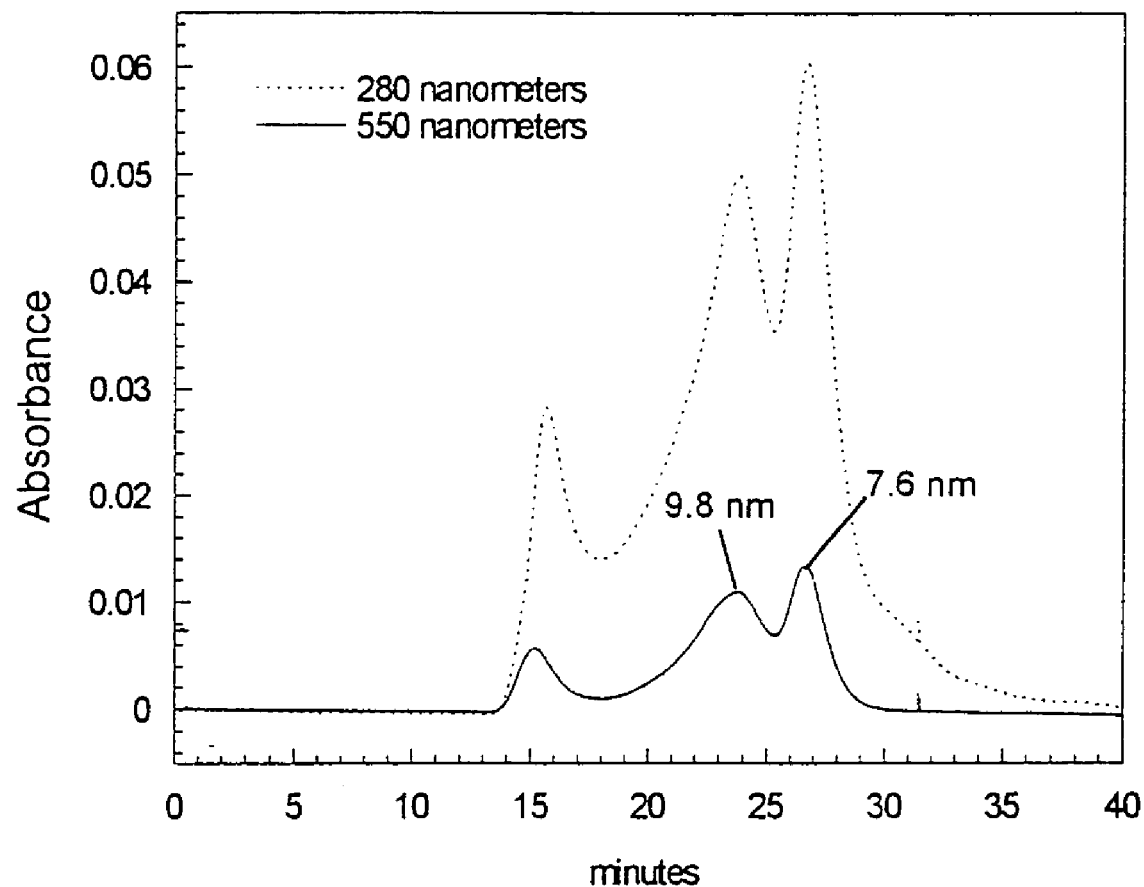
FIG. 12 is a gel filtration chromatogram of bacteriorhodopsin solubilized by MSP2 in the absence of added phospholipid. Bacteriorhodopsin is detected by absorbance at 550 nm, while MSP2 and bacteriorhodopsin protein is detected by absorbance at 280 nm.

We have shown that both MSP1 and MSP2 assemble with bacteriorhodopsin. From the initial reconstitution mixture, two bacteriorhodopsin-containing species are observed when particles are formed with MSP1 (FIG. 11) or MSP2 (FIG. 12) in the absence of added phospholipid. We found that the MSP is absolutely required for the solubilization of bacteriorhodopsin to form these species because omission of an MSP from the formation mixture results in large non-specific bacteriorhodopsin aggregates that elute in the void volume of the gel filtration column. The small peak at 15 minutes in FIG. 11 represents BR aggregates. In these experiments, it appears that the majority of bacteriorhodopsin appears solubilized in the presence of MSPs. The two sizes of particles observed are completely consistent with the putative "hinge domain" adopting alternate conformations in the structures. From previous work, this flexible hinge region is believed to consist of helices corresponding to helices 5 and 6 of human Apo-AI and thus by inference to MSP1. Thus, in the 9.8 nanometer diameter bacteriorhodopsin-containing particles, these flexible parts of the protein structure appear to be associated with the hydrophobic core of the structure while in 7.6 nanometer diameter particles, this helical region is dissociated from the hydrophobic core, thus forming a smaller diameter particle.

Further modifications of the parent Apo-AI protein can generate more effective and stable membrane scaffold proteins. For instance, to increase the homogeneity of the BR/MSP structures and to address the issue of the flexible "hinge" region of the protein structure discussed above, we have deleted the hinge domain region to produce two new membrane scaffold proteins. In the first case, putative helical regions 4 and 5 were deleted from the MSP1 histidine-tagged construct to produce a construct called MSP1D5–6. In a second experiment, the putative helices 5 and 6 were deleted to produce a material termed MSP1D4–5. We have overexpressed these proteins in *E. coli*, which are expressed at high levels upon induction of expression with isopropyl-thio-b-D-galactopyranoside in lac-regulated constructs.

An alternative way of avoiding the formation of multiple particle size classes is to engineer MSP constructs so that the hinge domain helices are replaced by helices having higher affinities for the hydrophobic core of the particles. In this case, the higher affinity interaction disfavors the formation of the smaller species wherein the hinge domain is dissociated. In this experimental line, we have chosen to replace the hinge region (helices 5 and 6) with the protein sequence corresponding to the native sequence corresponding to helices 1 and 2. In another manifestation, we have chosen a DNA construct encoding a membrane scaffold protein wherein the protein sequence corresponding to the putative helical regions 3 and 4 are used to replace the hinge region with a goal of yielding a single size particle upon assembly with bacteriorhodopsin and lipid.

The so-called "half-repeat" units present in the parent human Apo-AI protein also may give rise to conformational heterogeneity in MSP assemblies. For instance, in the picket fence model these helices adopt a conformation parallel to the bilayer plane and do not play a major role in interactions with the hydrophobic core of the particle as the other regions of the protein sequence are envisioned to contribute. In the "belt model" these short helical repeats could give rise to segmented mobility allowing the MSP to adopt different conformations. In other words, a MSP in which the number of types of structural elements is minimized is most likely desirable embodiment of the membrane scaffold protein concept. Thus, in order to further optimize the structure of the membrane scaffold protein with respect to their ability to solubilize integral membrane protein targets, we can engineer derivative sequences that will delete both half-repeat units to produce a simplified MSP structure.

Monoclonal or polyclonal antibodies, preferably monoclonal, specifically reacting with an MSP of the present invention can be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1993) *Current Protocols in Molecular Biology*, Wiley Interscience, New York, N.Y.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1–4, Plenum Press, New York; and Ausubel et al. (1992) *Current Protocols in Molecular Biology*, Greene/Wiley, New York, N.Y. Abbreviations and nomenclature, where employed, are deemed standard in the field and commonly used in professional journals such as those cited herein.

All references cited in the present application are incorporated by reference herein to the extent that there is no inconsistency with the present disclosure.

The description provided herein is not intended to limit the scope of the invention as claimed herein. Any variations in the exemplified articles and methods which occur to the skilled artisan are intended to fall within the scope of the present invention.

EXAMPLES

Example 1

Construction of Recombinant DNA Molecules for Expression of MSPs

The human proapoAI coding sequence as given below was inserted between Nco I and Hind III sites (underlined) in pET-28 (Novagen, Madison, Wis.). Start and stop codons are in bold type. The restriction endonuclease recognition sites used in cloning are underlined.

TABLE 1

ProApoAI coding sequence (SEQ ID NO: 1)

Restriction sites used in cloning are underlined, and the translation start and stop signals are shown in bold.

CC<u>ATGG</u>CCCATTTCTGGCAGCAAGATGAACCCCCCCAGAGCCCCTGGGAT

CGAGTGAAGGACCTGGCCACTGTGTACGTGGATGTGCTCAAAGACAGCGG

CAGAGACTATGTGTCCCAGTTTGAAGGCTCCGCCTTGGGAAAACAGCTAA

ACCTAAAGCTCCTTGACAACTGGGACAGCGTGACCTCCACCTTCAGCAAG

CTGCGCGAACAGCTCGGCCCTGTGACCCAGGAGTTCTGGGATAACCTGGA

AAAGGAGACAGAGGGCCTGAGGCAAGAGATGAGCAAGGATCTGGAGGAGG

TGAAGGCCAAGGTGCAGCCCTACCTGGACGACTTCCAGAAGAAGTGGCAG

GAGGAGATGGAGCTCTACCGCCAGAAGGTGGAGCCGCTGCGCGCAGAGCT

CCAAGAGGGCGCGCGCCAGAAGCTGCACGAGCTGCAAGAGAAGCTGAGCC

CACTGGGCGAGGAGATGCGCGACCGCGCGCGCGCCCATGTGGACGCGCTG

CGCACGCATCTGGCCCCCTACAGCGACGAGCTGCGCCAGCGCTTGGCCGC

GCGCCTTGAGGCTCTCAAGGAGAACGGCGGCGCCAGACTGGCCGAGTACC

ACGCCAAGGCCACCGAGCATCTGAGCACGCTCAGCGAGAAGGCCAAGCCC

GCGCTCGAGGACCTCCGCCAAGGCCTGCTGCCCGTGCTGGAGAGCTTCAA

GGTCAGCTTCCTGAGCGCTCTCGAGGAGTACACTAAGAAGCTCAACACCC

AGTAA<u>AAGCTT</u>-3'

TABLE 2

ProapoaI amino acid sequence (SEQ ID NO: 2)

MAHFWQQDEPPQSPWDRVKDLATVYVDVLKDSGRDYVSQFEGSALGKQLN

LKLLDNWDSVTSTFSKLREQLGPVTQEFWDNLEKETEGLRQEMSKDLEEV

KAKVQPYLDDFQKKWQEEMELYRQKVEPLRAELQEGARQKLHELQEKLSP

LGEEMRDRARAHVDALRTHLAPYSDELRQRLAARLEALKENGGARLAEYH

AKATEHLSTLSEKAKPALEDLRQGLLPVLESFKVSFLSALEEYTKKLNTQ

The construction of the MSP1 coding sequence was accomplished as follows. Primers were designed to produce DNA encoding MSP1, the truncated protein lacking the N-terminal domain of proApoAI, by polymerase chain reaction (PCR) mutagenesis (Higuchi et al., 1988). Primer 1 (SEQ ID NO:3) (5'-TATACCATGGGCCATCATCATCAT-CATCATATAGAAGGAAGACTAAAGCTCCT TGA-CAACT-3') introduces an N-terminal 6-histidine tag for purification and manipulation of MSP1, and a factor Xa cleavage site for removal of the histidine tag. Factor Xa cleaves after R in the protein sequence IEGR. Primer 2 (SEQ ID NO:4) (5'-GCAAGCTTATTACTGGGTGTTGAGCT-TCTT-3') was used as a reverse primer.

TABLE 3

Histidine-tagged MSP1 coding sequence (SEQ ID NO: 5).

Restriction sites used in cloning are underlined, and the translation start and stop signals are shown in bold.

TATA<u>CCATGG</u>GCCATCATCATCATCATCATATAGAAGGAAGACTAAAGCT

CCTTGACAACTGGGACAGCGTGACCTCCACCTTCAGCAAGCTGCGCGAAC

AGCTCGGCCCTGTGACCCAGGAGTTCTGGGATAACCTGGAAAAGGAGACA

GAGGGCCTGAGGCAGGAGATGAGCAAGGATCTGGAGGAGGTGAAGGCCAA

TABLE 3-continued

Histidine-tagged MSP1 coding sequence (SEQ ID NO: 5).

Restriction sites used in cloning are underlined, and the translation start and stop signals are shown in bold.

GGTGCAGCCCTACCTGGACGACTTCCAGAAGAAGTGGCAGGAGGAGATGG

AGCTCTACCGCCAGAAGGTGGAGCCGCTGCGCGCAGAGCTCCAAGAGGGC

GCGCGCCAGAAGCTGCACGAGCTGCAAGAGAAGTTGAGCCCACTGGGCGA

GGAGATGCGCGACCGCGCGCGCGCCCATGTGGACGCGCTGCGCACGCATC

TGGCCCCCTACAGCGACGAGCTGCGCCAGCGCTTGGCCGCGCGCCTTGAG

GCTCTCAAGGAGAACGGCGGCGCCAGACTGGCCGAGTACCACGCCAAGGC

CACCGAGCATCTGAGCACGCTCAGCGAGAAGGCCAAACCCGCGCTCGAGG

ACCTCCGCCAAGGCCTGCTGCCCGTGCTGGAGAGCTTCAAGGTCAGCTTC

CTGAGCGCTCTCGAGGAGTACACTAAGAAGCTCAACACCCAGTAAT<u>AAGC</u>
<u>TT</u>GC

TABLE 4

Histidine-tagged MSP1 amino acid sequence (SEQ ID NO: 6)

MGHHHHHHIEGRLKLLDNWDSVTSTFSKLREQLGPVTQEFWDNLEKETEG

LRQEMSKDLEEVKAKVQPYLDDFQKKWQEEMELYRQKVEPLRAELQEGAR

QKLHELQEKLSPLGEEMRDRARAHVDALRTHLAPYSDELRQRLAARLEAL

KENGGARLAEYHAKATEHLSTLSEKAKPALEDLRQGLLPVLESFKVSFLS

ALEEYTKKLNTQ

For production of MSP1 without a N-terminal histidine tag, primer 1 was replaced with primer 1a: 5'-TACCATG-GCAAAGCTCCTTGACAACTG-3' (SEQ ID NO:7) to produce the sequence provided in SEQ ID NO:8.

TABLE 5

Non-Histidine-tagged MSP1 DNA sequence (SEQ ID NO: 8).

Restriction sites used in cloning are underlined, and the translation start and stop signals are shown in bold.

TA<u>CCATGG</u>CAAAGCTCCTTGACAACTGGGACAGCGTGACCTCCACCTTCAGCAAGC

TGCGCGAACAGCTCGGCCCTGTGACCCAGGAGTTCTGGGATAACCTGGAAAAGGA

GACAGAGGGCCTGAGGCAGGAGATGAGCAAGGATCTGGAGGAGGTGAAGGCCA

AGGTGCAGCCCTACCTGGACGACTTCCAGAAGAAGTGGCAGGAGGAGATGGAGC

TCTACCGCCAGAAGGTGGAGCCGCTGCGCGCAGAGCTCCAAGAGGGCGCGCGCC

AGAAGCTGCACGAGCTGCAAGAGAAGTTGAGCCCACTGGGCGAGGAGATGCGCG

ACCGCGCGCGCGCCCATGTGGACGCGCTGCGCACGCATCTGGCCCCCTACAGCG

ACGAGCTGCGCCAGCGCTTGGCCGCGCGCCTTGAGGCTCTCAAGGAGAACGGCG

GCGCCAGACTGGCCGAGTACCACGCCAAGGCCACCGAGCATCTGAGCACGCTCA

GCGAGAAGGCCAAACCCGCGCTCGAGGACCTCCGCCAAGGC

TABLE 5-continued

Non-Histidine-tagged MSP1 DNA sequence (SEQ ID NO: 8).
Restriction sites used in cloning are underlined, and the translation start and stop signals are shown in bold.

CTGCTGCCCGTGCTGGAGAGCTTCAAGGTCAGCTTCCTGAGCGCTCTCGAGGAGT

ACACTAAGAAGCTCAACACCCAGTAATAAGCTTGC

TABLE 6.

Non-Histidine-tagged MSP1 amino acid sequence (SEQ ID NO: 9).

MAKLLDNWDSVTSTFSKLREQLGPVTQEFWDNLEKETEGLRQEMSKDLEE

VKAKVQPYLDDFQKKWQEEMELYRQKVEPLRAELQEGARQKLHELQEKLS

PLGEEMRDRARAHVDALRTHLAPYSDELRQRLAARLEALKENGGARLAEY

HAKATEHLSTLSEKAKPALEDLRQGLLPVLESFKVSFLSALEEYTKKLNT

Q

Figure 6A:
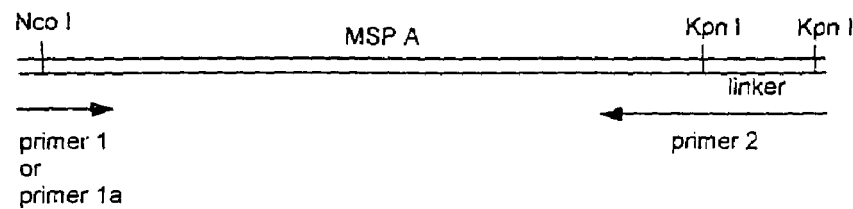
FIGS. 6A–6B diagrammatically illustrate the PCR strategy used to amplify artificial MSPs.
Figure 6B:
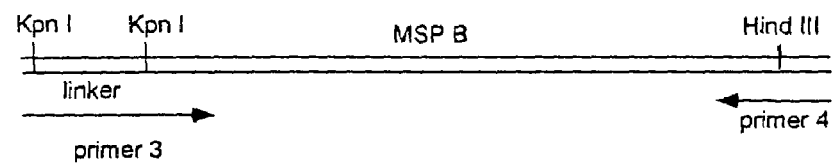
Figure 7A:
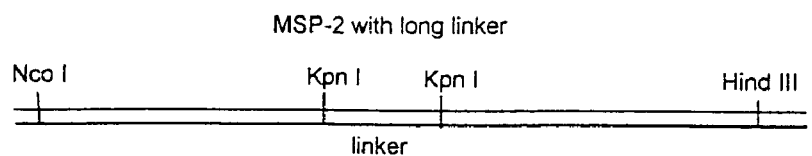
FIGS. 7A–7B shows diagrams of MSP2 with (FIG. 7A) and without a long linker sequence (FIG. 7B).
Figure 7B:
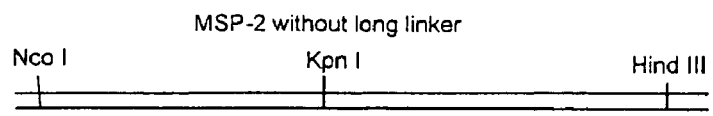
Figure 8A:
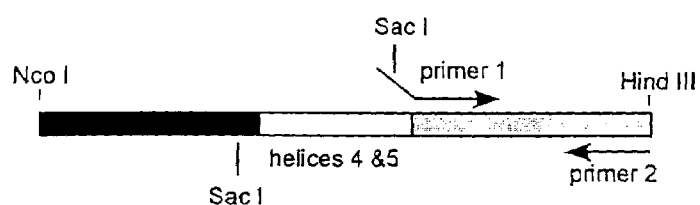
FIGS. 8A–8B illustrate the strategy for constructing and expressing an artificial sequence encoding an MSP1 derivative lacking helices 4 and 5.
Figure 8B:
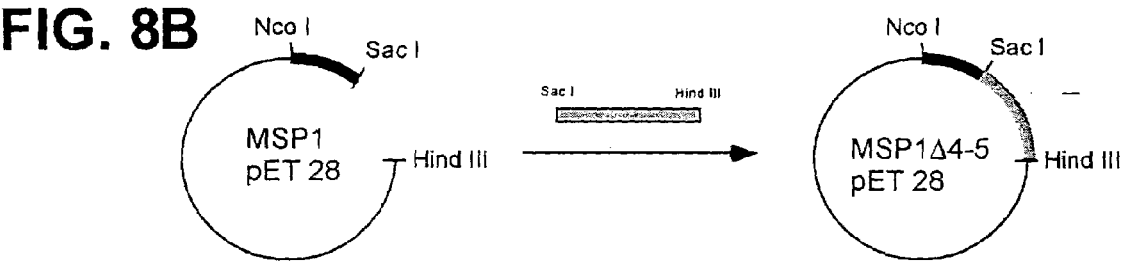

The production of an MSP with tandem repeats (MSP2) was carried at as described below. The following primers were used to generate MSP2 (see FIGS. 6A–6B):

In a first PCR, primer 2 (or primer 2a for N-terminal histidine tag) and primer 4 were used to add a linker (encoding the amino acid sequence GTGGGSGGGT; SEQ ID NO: 15) to the 3' end of the MSP gene to produce MSP-A. In a second PCR, the linker was added to the 5' end of the MSP gene to produce MSP-B. Treatment of MSP-A and MSP-B with KpnI and subsequent ligation produced the following constructs, one with and one without the linker. The Kpn I site provides an easy way to inserting any desired linker sequence by restriction with Kpn I and religation with double-stranded synthetic DNA encoding desired linker. See FIGS. 7A–7B.

Primer 3 (SEQ ID NO: 10):   5'-TACCATGGCAAAGCTCCTTGACAACTG-3' primer 3a (SEQ ID NO: 11):  5'-TATACCATGGGCCATCATCATCATCATCATATAGAAGGAAGACTAAAGCTCCT
                               TGACAACT-3'

Primer 4 (SEQ ID NO: 12):   5'-TAAGAAGCTCAACACCCAGGGTACCGGTGGAGGTAGTGGAGGTGGTACCCTA-3'

Primer 5 (SEQ ID NO: 13):   5'-CAGGGTACCGGTGGAGGTAGTGGAGGTGGTACCCTAAAGCTCCTTGACAA-3'

Primer 6 (SEQ ID NO: 14):   5'-GCAAGCTTATTACTGGGTGTTGAGCTTCTT-3'

TABLE 7

MSP2 (with histidine tag, without long linker) DNA sequence (SEQ ID NO: 16).
The translation start and stop codons are in bold type, and the restriction endonuclease recognition sites used in cloning are underlined.

TATA<u>CCATGG</u>GCCATCATCATCATCATCATATAGAAGGAAGACTAAAGCTCCTTGACA

ACTGGGACAGCGTGACCTCCACCTTCAGCAAGCTGCGCGAACAGCTCGGCCCTGTGA

CCCAGGAGTTCTGGGATAACCTGGAAAAGGAGACAGAGGGCCTGAGGCAGGAGATG

AGCAAGGATCTGGAGGAGGTGAAGGCCAAGGTGCAGCCCTACCTGGACGACTTCCA

GAAGAAGTGGCAGGAGGAGATGGAGCTCTACCGCCAGAAGGTGGAGCCGCTGCGCG

CAGAGCTCCAAGAGGGCGCGCGCCAGAAGCTGCACGAGCTGCAAGAGAAGCTGAG

CCCACTGGGCGAGGAGATGCGCGACCGCGCGCGCGCCCATGTGGACGCGCTGCGCA

CGCATCTGGCCCCCTACAGCGACGAGCTGCGCCAGCGCTTGGCCGCGCGCCTTGAGG

CTCTCAAGGAGAACGGCGGCGCCAGACTGGCCGAGTACCACGCCAAGGCCACCGAG

TABLE 7-continued

MSP2 (with histidine tag, without long linker) DNA sequence (SEQ ID NO: 16).
The translation start and stop codons are in bold type, and the restriction
endonuclease recognition sites used in cloning are underlined.

CATCTGAGCACGCTCAGCGAGAAGGCCAAGCCCGCGCTCGAGGACCTCCGCCAAGG

CCTGCTGCCCGTGCTGGAGAGCTTCAAGGTCAGCTTCCTGAGCGCTCTCGAGGAGTA

CACTAAGAAGCTCAACACCCAGGGTACCCTAAAGCTCCTTGACAACTGGGACAGCGTGACCTCCACCTTCAGCAA

GCTGCGCGAACAGCTCGGCCCTGTGACCCAGGAGTTCTGGGATAACCTGGAAAAGGAGACAGAGGGCCTGAGGCA

GGAGATGAGCAAGGATCTGGAGGAGGTGAAGGCCAAGGTGCAGCCCTACCTGGACGACTTCCAGAAGAAGTGGCA

GGAGGAGATGGAGCTCTACCGCCAGAAGGTGGAGCCGCTGCGCGCAGAGCTCCAAGAGGGCGCGCGCCAGAAGCT

GCACGAGCTGCAAGAGAAGCTGAGCCCACTGGGCGAGGAGATGCGCGACCGCGCGCGCGCCCATGTGGACGCGCT

GCGCACGCATCTGGCCCCCTACAGCGACGAGCTGCGCCAGCGCTTGGCCGCGCGCCTTGAGGCTCTC

AAGGAGAACGGCGGCGCCAGACTGGCCGAGTACCACGCCAAGGCCACCGAGCATCTGAGCACGCTCAGCGAGAAG

GCCAAGCCCGCGCTCGAGGACCTCCGCCAAGGCCTGCTGCCCGTGCTGGAGAGCTTCAAGGTCAGCTTCCTGAGC

GCTCTCGAGGAGTACACTAAGAAGCTCAACACCCAGTAATAAGCTTGC

TABLE 8

MSP2 (with histidine tag, without long linker)
amino acid sequence (SEQ ID NO: 17)

MGHHHHHHIEGRLKLLDNWDSVTSTFSKLREQLGPVTQEFWDNLEKETEG

LRQEMS/KDLEEVKAKVQPYLDDFQKKWQEEMELYRQKVEPLRAELQEGA

RQKLHELQEKLSPLGEEMRDRARAHVDALRTHLAPYSDELRQRLAARLEA

LKENGGARLAEYHAKATEHLSTLSEKAKPALEDLRQGLLPVLESFKVSFL

SALEEYTKKLNTQGTLKLLDNWDSVTSTFSKLREQLGPVTQEFWDNLEKE

TABLE 8-continued

MSP2 (with histidine tag, without long linker)
amino acid sequence (SEQ ID NO: 17)

TEGLRQEMSKDLEEVKAKVQPYLDDFQKKWQEEMELYRQKVEPLRAELQE

GARQKLHELQEKLSPLGEEMRDRARAHVDALRTHLAPYSDELRQRLAARL

EALKENGGARLAEYHAKATEHLSTLSEKAKPALEDLRQGLLPVLESFKVS

FLSALEEYTKKLNTQ

TABLE 9

MSP2 (with histidine tag, with long linker) DNA sequence
(SEQ ID NO: 18). Translation start and stop codons are in bold type;
restriction endonuclease sites used in cloning are underlined.

TA<u>CCATGG</u>GCCATCATCATCATCATCATATAGAAGGAAGACTAAAGCTCCTTGACAA

CTGGGACAGCGTGACCTCCACCTTCAGCAAGCTGCGCGAACAGCTCGGCCCTGTGAC

CCAGGAGTTCTGGGATAACCTGGAAAAGGAGACAGAGGGCCTGAGGCAGGAGATGA

GCAAGGATCTGGAGGAGGTGAAGGCCAAGGTGCAGCCCTACCTGGACGACTTCCAG

AAGAAGTGGCAGGAGGAGATGGAGCTCTACCGCCAGAAGGTGGAGCCGCTGCGCGC

AGAGCTCCAAGAGGGCGCGCGCCAGAAGCTGCACGAGCTGCAAGAGAAGCTGAGCC

CACTGGGCGAGGAGATGCGCGACCGCGCGCGCGCCCATGTGGACGCGCTGCGCACG

CATCTGGCCCCCTACAGCGACGAGCTGCGCCAGCGCTTGGCCGCGCGCCTTGAGGCT

CTCAAGGAGAACGGCGGCGCCAGACTGGCCGAGTACCACGCCAAGGCCACCGAGCA

TCTGAGCACGCTCAGCGAGAAGGCCAAGCCCGCGCTCGAGGACCTCCGCCAAGGCC

TGCTGCCCGTGCTGGAGAGCTTCAAGGTCAGCTTCCTGAGCGCTCTCGAGGAGTACA

CTAAGAAGCTCAACACCCAGGGTACCGGTGGAGGTAGTGGAGGTGGTACCCTAAAG

CTCCTTGACAACTGGGACAGCGTGACCTCCACCTTCAGCAAGCTGCGCGAACAGCTC

TABLE 9-continued

MSP2 (with histidine tag, with long linker) DNA sequence (SEQ ID NO: 18). Translation start and stop codons are in bold type; restriction endonuclease sites used in cloning are underlined.

GGCCCTGTGACCCAGGAGTTCTGGGATAACCTGGAAAAGGAGACAGAGGGCCTGAG

GCAGGAGATGAGCAAGGATCTGGAGGAGGTGAAGGCCAAGGTGCAGCCCTACCTGG

ACGACTTCCAGAAGAAGTGGCAGGAGGAGATGGAGCTCTACCGCCAGAAGGTGGAGCCGCTGCGCGCAGAGCTCC

AAGAGGGCGCGCGCCAGAAGCTGCACGAGCTGCAAGAGAAGCTGAGCCCACTGGGCGAGGAGATGCGCGACCGCG

CGCGCGCCCATGTGGACGCGCTGCGCACGCATCTGGCCCCCTACAGCGACGAGCTGCGCCAGCGCTTGGCCGCGC

GCCTTGAGGCTCTCAAGGAGAACGGCGGCGCCAGACTGGCCGAGTACCACGCCAAGGCCACCGAGCATCTGAGCA

CGCTCAGCGAGAAGGCCAAGCCCGCGCTCGAGGACCTCCGCCAAGGCCTGCTGCCCGTGCTGGAGAGCTTCAAGG

TCAGCTTCCTGAGCGCTCTCGAGGAGTACACTAAGAAGCTCAACACCCAGTAATAAGCTTGC

TABLE 10

MSP2 (with histidine tag, with long linker, in bold type) amino acid sequence (SEQ ID NO: 19).

MGHHHHHHIEGRLKLLDNWDSVTSTFSKLREQLGPVTQEFWDNLEKETEGLRQEMS

KDLEEVKAKVQPYLDDFQKKWQEEMELYRQKVEPLRAELQEGARQKLHELQEKLSP

LGEEMRDRARAHVDALRTHLAPYSDELRQRLAARLEALKENGGARLAEYHAKATE

HLSTLSEKAKPALEDLRQGLLPVLESFKVSFLSALEEYTKKLNTQGTGGGSGGGTLK

LLDNWDSVTSTFSKLREQLGPVTQEFWDNLEKETEGLRQEMSKDLEEVKAKVQPYL

DDFQKKWQEEMELYRQKVEPLRAELQEGARQKLHELQEKLSPLGEEMRDRARAHV

DALRTHLAPYSDELRQRLAARLEALKENGGARLAEYHAKATEHLSTLSEKAKPALED

LRQGLLPVLESFKVSFLSALEEYTKKLNTQ

To delete hinge regions, deletion of helices 4 and 5 was carried out by constructing the C-terminal portion of MSP1 using the following PCR primers and the Sac I and Hind III fragment of the MSP1 coding sequence as template.

Primer A (SEQ ID NO: 20):  5'-TGGAGCTCTACCGCCAGAAGGTGGAGCCCTACAGCGACGAGCT-3'/

Primer B (SEQ ID NO: 21):  5'-GCAAGCTTATTACTGGGTGTTGAGCTTCTT-3'.

This amplification product was digested with SacI and HindIII and ligated into pLitmus 28 for sequencing. The Sac I+HindIII treated histidine-MSP1 construct in pET 28 vector was then ligated with the above fragment to produce MSP1D4–5.

TABLE 11

MSP1D4-5 (helices 4 and 5 deleted) DNA sequence (SEQ ID NO: 22). Translations start and stop codons are in bold type; restriction endonuclease recognition sites are underlined.

TATA<u>CCATGG</u>GCCATCATCATCATCATCATATAGAAGGAAGACTAAAGCTCCTTG

ACAACTGGGACAGCGTGACCTCCACCTTCAGCAAGCTGCGCGAACAGCTCGGCC

TABLE 11-continued

MSP1D4-5 (helices 4 and 5 deleted) DNA sequence (SEQ ID NO: 22). Translations start and stop codons are in bold type; restriction endonuclease recognition sites are underlined.

CTGTGACCCAGGAGTTCTGGGATAACCTGGAAAAGGAGACAGAGGGCCTGAGGC

AGGAGATGAGCAAGGATCTGGAGGAGGTGAAGGCCAAGGTGCAGCCCTACCTGG

ACGACTTCCAGAAGAAGTGGCAGGAGGAGATGGAGCTctaccgccagaaggtggagcCCTA

CAGCGACGAGCTGCGCCAGCGCTTGGCCGCGCGCCTTGAGGCTCTCAAGGAGAA

CGGCGGCGCCAGACTGGCCGAGTACCACGCCAAGGCCACCGAGCATCTGAGCAC

GCTCAGCGAGAAGGCCAAACCCGCGCTCGAGGACCTCCGCCAAGGCCTGCTGCC

CGTGCTGGAGAGCTTCAAGGTCAGCTTCCTGAGCGCTCTCGAGGAGTACACTAAG

AAGCTCAACACCCAGTAATAAGCTTGC

TABLE 12

MSP1D4-5 (helices 4 and 5 deleted) amino acid sequence (SEQ ID NO: 23).

MGHHHHHHIEGRLKLLDNWDSVTSTFSKLREQLGPVTQEFWDNLEKETEGLRQEMS

KDLEEVKAKVQPYLDDFQKKWQEEMELYRQKVEPYSDELRQRLAARLEALKENGG

ARLAEYHAKATEHLSTLSEKAKPALEDLRQGLLPVLESFKVSFLSALEEYTKKLNTQ

Deletion of helices 5 and 6 was performed in a similar manner, but two separate PCR steps using the following primers were employed in a first reaction (Reaction 1, Primer C: 5'-CAGAATTCGCTAGCCGAGTACCACGC-CAA-3', SEQ ID NO:24; and Primer D: 5'-GCAAGCTTAT-TACTGGGTGTTGAGCTTCTT-3', SEQ ID NO:25) and a second reaction (Reaction 2, Primer E: 5'-ATAC-CATGGGCCATCATCATCATCATCATA-3', SEQ ID NO:26; and Primer F: 5'-CAGAATTCGCTAGCCTG-GCGCTCAACTTCTCTT-3', SEQ ID NO:27.

Figure 9A:
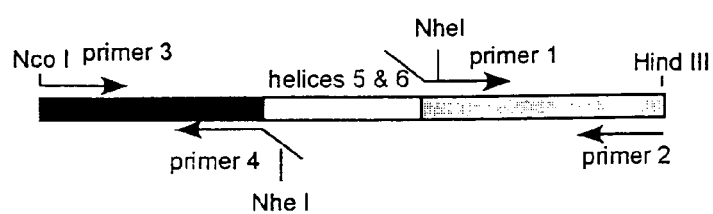
FIGS. 9A–9B illustrate the strategy for constructing and expressing an artificial sequence encoding an MSP1 derivative lacking helices 5 and 6.
Figure 9B:
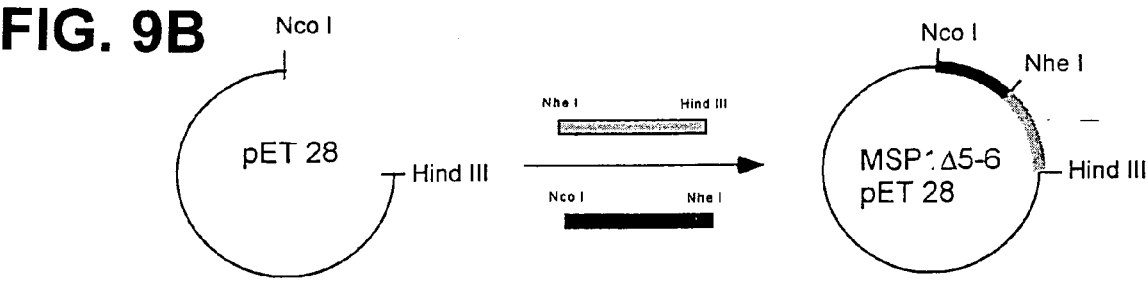

The PCR products encode the N- and C-terminal portions of MSP both lacking helices 5 and 6 and each contain a NheI restriction site. After digestion of the PCR products with Nhe I, NcoI and HindIII, the fragments was ligated into NcoI+HindIII treated pET 28 to produce the DNA sequence of MSP1D5–6 lacking helices 5 and 6. See FIGS. 9A–9B.

TABLE 13

MSP1D5-6 (helices 5 and 6 deleted) DNA sequence (SEQ ID NO: 28). Translation start and stop codons are shown in bold type, and restriction endonuclease recognition sites used in cloning are underlined.

TATAC<u>CATGG</u>GCCATCATCATCATCATCATATAGAAGGAAGACTAAAGCTCCTTGA

CAACTGGGACAGCGTGACCTCCACCTTCAGCAAGCTGCGCGAACAGCTCGGCCCTG

TGACCCAGGAGTTCTGGGATAACCTGGAAAAGGAGACAGAGGGCCTGAGGCAGG

AGATGAGCAAGGATCTGGAGGAGGTGAAGGCCAAGGTGCAGCCCTACCTGGACG

ACTTCCAGAAGAAGTGGCAGGAGGAGATGGAGCTCTACCGCCAGAAGGTGGAGC

CGCTGCGCGCAGAGCTCCAAGAGGGCGCGCGCCAGAAGCTGCACGAGCTGCAAG

AGAAGTTGAGCGCCAGGCTAGCCGAGTACCACGCCAAGGCCACCGAGCATCTGA

GCACGCTCAGCGAGAAGGCCAAACCCGCGCTCGAGGACCTCCGCCAAGGCCTGC

TGCCCGTGCTGGAGAGCTTCAAGGTCAGCTTCCTGAGCGCTCTCGAGGAGTACAC

TAAGAAGCTCAACACCCAGTAAT<u>AAGCTT</u>GC

TABLE 14

MSP1D5-6 (helices 5 and 6 deleted) amino acid sequence (SEQ ID NO: 29).

MGHHHHHHIEGRLKLLDNWDSVTSTFSKLREQLGPVTQEFWDNLEKETEGLRQEMS

KDLEEVKAKVQPYLDDFQKKWQEEMELYRQKVEPLRAELQEGARQKLHELQEKLS

ARLAEYHAKATEHLSTLSEKAKPALEDLRQGLLPVLESFKVSFLSALEEYTKKLNTQ

Example 2

Construction of Synthetic MSP Gene

A synthetic gene for MSP1 is made using the following overlapping synthetic oligonucleotides which are filled in using PCR. The codon usage has been optimized for expression in *E. coli*, and restriction sites have been introduced for further genetic manipulations of the gene.

Synthetic nucleotide taps1a (SEQ ID NO: 30)

TACCATGGGTCATCATCATCATCATCACATTGAGGGACGTCTGAAGCTGTT

GGACAATTGGGACTCTGTTACGTCTA

Synthetic nucleotide taps2a (SEQ ID NO: 31)

AGGAATTCTGGGACAACCTGGAAAAAGAAACCGAGGGACTGCGTCAGGA

AATGTCCAAAGAT

Synthetic nucleotide taps3a (SEQ ID NO: 32)

TATCTAGATGACTTTCAGAAAAAATGGCAGGAAGAGATGGAATTATATCG

TCAA

Synthetic nucleotide taps4a (SEQ ID NO: 33)

ATGAGCTCCAAGAGAAGCTCAGCCCATTAGGCGAAGAAATGCGCGATCGC

GCCCGTGCACATGTTGATGCACT

Synthetic nucleotide taps5a (SEQ ID NO: 34)

GTCTCGAGGCGCTGAAAGAAACGGGGGTGCCCGCTTGGCTGAGTACCAC

GCGAAAGCGACAGAA

Synthetic nucleotide taps6a (SEQ ID NO: 35)

GAAGATCTACGCCAGGGCTTATTGCCTGTTCTTGAGAGCTTTAAAGTCAGT

TTTCT

-continued

Synthetic nucleotide taps 1b (SEQ ID NO: 36)

CAGAATTCCTGCGTCACGGGGCCCAGTTGTTCGCGAAGTTTACTGAAGGT

AGACGTAACAG

Synthetic nucleotide taps2b (SEQ ID NO: 37)

TCATCTAGATATGGCTGAACCTTGGCCTTCACCTCTTCTAAATCTTTGGAC

ATTT

Synthetic nucleotide taps3b (SEQ ID NO: 38)

TGGAGCTCATGGAGTTTTTGGCGTGCCCCCTCTTGCAGTTCCGCACGCAGC

GGTTCCACCTTTTGACGATATAATTCCAT

Synthetic nucleotide taps4b (SEQ ID NO: 39)

GCCTCGAGACGTGCGGCCAAACGCTGGCGAAGTTCATCCGAATACGGCGC

CAAATGAGTCCGGAGTGCATCAACAT

Synthetic nucleotide taps5b (SEQ ID NO: 40)

GTAGATCTTCCAGCGCCGGTTTCGCTTTTTCGCTCAAGGTGCTCAGGTGTT

CTGTCGCTTT

Synthetic nucleotide taps6b (SEQ ID NO: 41)

CCAAGCTTATTACTGGGTATTCAGCTTTTTAGTATATTCTTCCAGAGCTGA

CAGAAAACTGACTTT

TABLE 15

Full synthetic gene sequence for MSP1 (SEQ ID NO: 42). Restriction sites used in cloning are underlined, and the translation start and stop signals are shown in bold.

ACATGGGTCATCATCATCATCATCACATTGAGGGACGTCTGAAGCTGTTGGACAA

TTGGGACTCTGTTACGTCTACCTTCAGTAAACTTCGCGAACAACTGGGCCCCGTGAC

GCAGGAATTCTGGGACAACCTGGAAAAAGAAACCGAGGGACTGCGTCAGGAAATG

TCCAAAGATTTAGAAGAGGTGAAGGCCAAGGTTCAGCCATATCTAGATGACTTTCA

TABLE 15-continued

Full synthetic gene sequence for MSP1 (SEQ ID NO: 42).
Restriction sites used in cloning are underlined, and the
translation start and stop signals are shown in bold.

GAAAAAATGGCAGGAAGAGATGGAATTATATCGTCAAAAGGTGGAACCGCTGCG

TGCGGAACTGCAAGAGGGGGCACGCCAAAAACTCCATGAGCTCCAAGAGAAGCT

CAGCCCATTAGGCGAAGAAATGCGCGATCGCGCCCGTGCACATGTTGATGCACT

CCGGACTCATTTGGCGCCGTATTCGGATGAACTTCGCCAGCGTTTGGCCGCACGT

CTCGAGGCGCTGAAAGAAAACGGGGGTGCCCGCTTGGCTGAGTACCACGCGAAA

GCGACAGAACACCTGAGCACCTTGAGCGAAAAAGCGAAACCGGCGCTGGAAGAT

CTACGCCAGGGCTTATTGCCTGTTCTTGAGAGCTTTAAAGTCAGTTTTCTGTCAGC

TCTGGAAGAATATACTAAAAAGCTGAATACCCAGTAATAAGCTTGG

The following is the amino acid sequence of a MSPp polypeptide in which half repeats are deleted:

TABLE 16

MSP with first half-repeat deleted (MSP1delta1) (SEQ ID NO: 43)

MGHHHHHHIEGRLKLLDNWDSVTSTFSKLREQLGPVTQEFWDNLEKETEGLRQEMS

PYLDDFQKKWQEEMELYRQKVEPLRAELQEGARQKLHELQEKLSPLGEEMRDRAR

AHVDALRTHLAPYSDELRQRLAARLEALKENGGARLAEYHAKATEHLSTLSEKAKP

ALEDLRQGLLPVLESFKVSFLSALEEYTKKLNTQ

TABLE 17

MSP with second half-repeat deleted (MSP1delta2) (SEQ ID NO: 44)

MGHHHHHHIEGRLKLLDNWDSVTSTFSKLREQLGPVTQEFWDNLEKETEGLRQEMS

KDLEEVKAKVQPYLDDFQKKWQEEMELYRQKVEPLRAELQEGARQKLHELQEKLS

PLGEEMRDRARAHVDALRTHLAPYSDELRQRLAARLEALKENGGARLAEYHAKAT

EHLSTLSEKAKPVLESFKVSFLSALEEYTKKLNTQ

TABLE 18

MSP tandem repeat with first half-repeats deleted
(MSP2delta1) (SEQ ID NO: 45)

MGHHHHHHIEGRLKLLDNWDSVTSTFSKLREQLGPVTQEFWDNLEKETEGLRQEMS

PYLDDFQKKWQEEMELYRQKVEPLRAELQEGARQKLHELQEKLSPLGEEMRDRAR

AHVDALRTHLAPYSDELRQRLAARLEALKENGGARLAEYHAKATEHLSTLSEKAKP

ALEDLRQGLLPVLESFKVSFLSALEEYTKKLNTQGTLKLLDNWDSVTSTFSKLREQL

GPVTQEFWDNLEKETEGLRQEMSPYLDDFQKKWQEEMELYRQKVEPLRAELQEGA

RQKLHELQEKLSPLGEEMRDRARAHVDALRTHLAPYSDELRQRLAARLEALKENGG

ARLAEYHAKATEHLSTLSEKAKPALEDLRQGLLPVLESFKVSFLSALEEYTKKLNTQ

Other constructs that can be readily produced include permutations of the above, i.e. MSP1 or MSP2 with any combination of the following: hinge deletion, hinge replacement, half-repeat deletion, histidine tag, different linkers for MSP2.

Example 3

Expression of Recombinant MSPs

To express MSP proteins, the nucleic acid constructs were inserted between the NcoI and HindIII sites in the pET28 expression vector and transformed into *E. coli* BL21(DE3). Transformants were grown on LB plates using kanamycin for selection. Colonies were used to inoculate 5 ml starter cultures grown in LB broth containing 30 μg/ml kanamycin. For overexpression, cultures were inoculated by adding 1 volume overnight culture to 100 volumes LB broth containing 30 μg/ml kanamycin and grown in shaker flasks at 37° C. When the optical density at 600 nm reached 0.6–0.8, isopropyl b-D-thiogalactopyranoside (IPTG) was added to a concentration of 1 mM to induce expression and cells were grown 3–4 hours longer before harvesting by centrifugation. Cell pellets were flash frozen and stored at −80° C.

Example 4

Purification of Recombinant MSPs

Purification of histidine-tagged MSPs was carried out as follows. A frozen cell pellet from 1 liter of expression culture was resuspended in 25 milliliters of 20 mM Tris HCl pH 7.5 containing 1 mM phenylmethylsulfonyl fluoride. Triton X-100 (t-octylphenoxypolyethoxyethanol) was added from a 10% (w/v) stock in distilled H20 to a final concentration of 1%. The resuspended cells were sonicated on ice at 50% duty cycle at a power setting of 5 for four cycles of 1 minute on, 5 minutes off with a Branson probe sonifier. The resulting lysate was centrifuged for 30 minutes at 30,000 rpm in a Beckman Ti 45 rotor in a ultracentrifuge. The resulting supernatant was filtered through a 0.22 mm nylon syringe filter. The salt concentration was adjusted to 0.5 M from a 4 M NaCl stock in water and applied to a 5 ml Hi-Trap nickel loaded column (Pharmacia, Piscataway, N.J.).

For 6H-MSP1, the column is washed with 20 ml buffer (10 mM Tris pH 8, 0.5 M NaCl) containing 1% Triton X-100, followed by 20 ml buffer+50 mM sodium cholate, and then 20 ml buffer and 20 ml 100 mM imidazole in buffer. The His-tagged polypeptide is eluted with 15 ml 0.5 M imidazole in buffer.

For 6H-MSP2, the column is washed with 20 ml buffer (10 mM Tris pH 8, 0.5 M NaCl) containing 1% Triton X-100; 20 ml buffer+50 mM cholate; 20 ml buffer; 20 ml 35 mM imidazole in buffer. The His-tagged polypeptide is then eluted with 15 ml 0.5 M imidazole in buffer, and the purified protein is dialyzed against 10 mM Tris pH 8, 0.15 M NaCl using a 10,000 MW cutoff cellulose dialysis membrane.

Example 6

Production of MSP-Containing Nano Scale Particles

To reconstitute MSP proteins of the present invention with lipid, purified MSP was concentrated in a pressurized ultra-filtration device (Amicon) using a 10,000 MW cutoff filter to ~2–6 mg protein/ml. Concentration of protein was determined by bicinchonic acid assay (Pierce Chemical, Rockford, Ill.) or measurement of A280 using theoretical absorption coefficient. Phospholipid (dipalmitoyl phosphatidylcholine in this case, however different phosphatidylcholines and mixtures of phosphatidylcholine and other lipids can be used) in chloroform stock solution was dried under a stream of nitrogen and placed in vacuo overnight. Phosphate analysis was performed to determine the concentration of chloroform stock solutions. The dried lipid film was resuspended in buffer 10 mM Tris HCl pH 8.0 or pH 7.5 containing 0.15 M NaCl and 50 mM sodium cholate to give a final lipid concentration of 25 mM. The suspension was vortexed and heated to 50° C. to obtain a clear solution. Phospholipid solution was added to solution of MSP (2–6 mg/ml protein) to give molar ratios for MSP1:lipid of 2:200 and for MSP2 of 1:200. The mixture was incubated overnight at 37° C. and then dialyzed against 1000 volumes of buffer without cholate with 4 changes of buffer over 2–3 days.

Example 7

Tethered Membrane Protein Incorporation

Tissue Factor (TF) is a representative tethered membrane protein. In order to demonstrate the value of MSP technology for a tethered membrane protein, recombinant human TF was incorporated into MSP-supported nanodiscs. The recombinant protein consists of an extracellular domain, the transmembrane anchor and a truncated cytosolic domain. The truncation increases the homogeneity of the protein by removing the C-terminal portions of the protein which are subject to proteolysis by bacterial enzymes. This modification does not affect TF activity. Additional modifications to the protein include an N-terminal trafficking peptide and an HPC4 epitope tag. The trafficking peptide directs the expressed protein to the intermembrane space of the recombinant *E. coli* host cell, in which space the peptide sequence is cleaved. The HPC4 epitope allows for affinity purification with $Ca^{2+}$ dependent antibody (Rezaie et al., 1992) and does not affect TF activity.

Figures 16A, 16B:
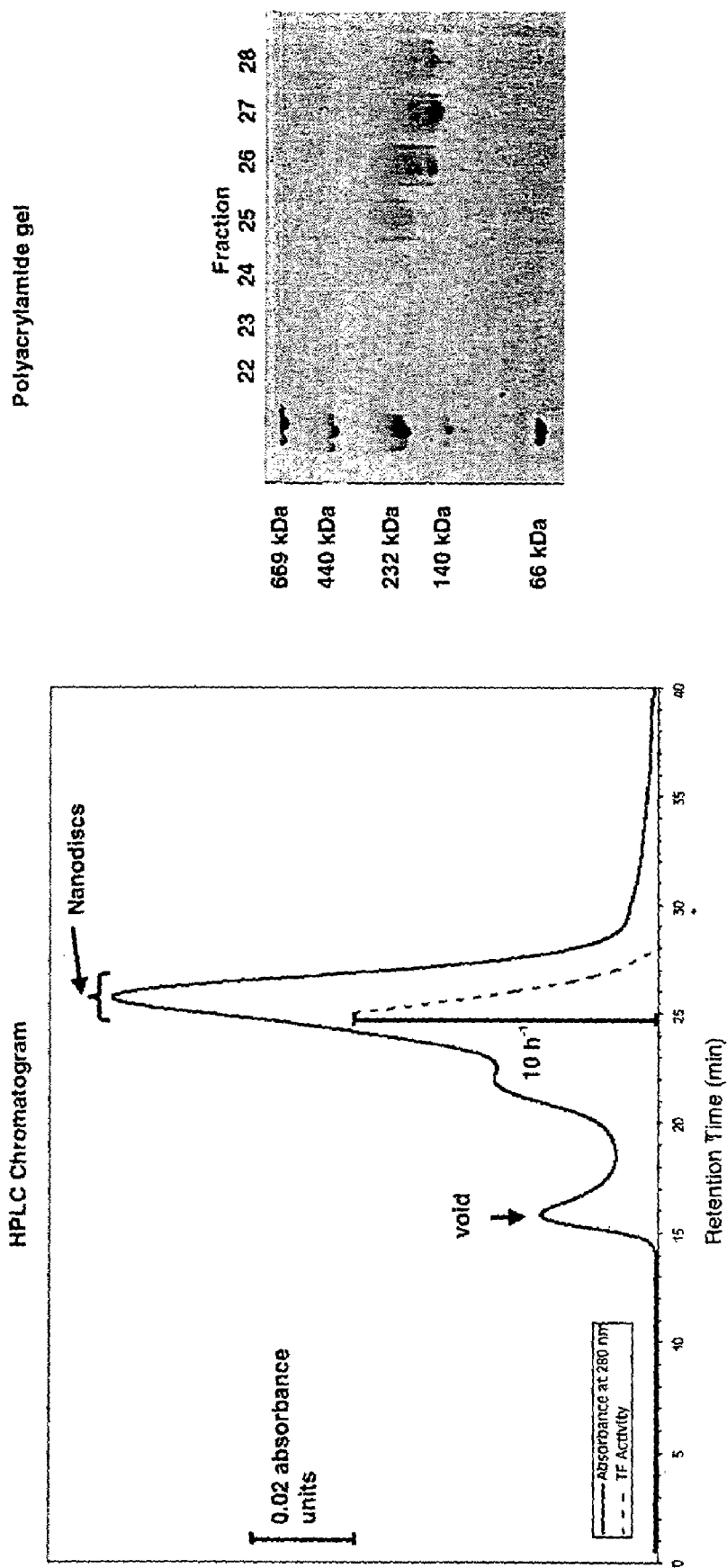
FIG. 16A shows the results of HPLC over a sizing column of nanodisc particles with retention times indicating 8 and 10 nm sizes and Tissue Factor activity at 25–28 ml.
FIG. 16B shows the results of SDS-PAGE using 8–25% gradient gels; the MSP1-supported nanodisc bilayers isolated from the HPLC and containing TF have the expected molecular weights.

A 25 mM lipid mixture containing 80% phosphatidyl choline and 20% phosphatidyl serine was solubilized with 50 mM cholate in 10 mM Tris Cl, 150 mM NaCl at pH 8.0. TF, MSP1 and lipid (in a ratio of 1:10:1000) were combined and incubated overnight at 37° C. The sample was then dialyzed at 37° C. (10,000 dalton molecular weight cutoff membrane) against buffer containing 10 mM Tris Cl, 150 mM NaCl at pH 8.0 (lacking cholate) for 2 hours. Dialysis was then continued at 4° C. for an additional 6 hours with buffer changes every 2 hours. The approximately 1 ml sample was then concentrated to <250 μl using a YM-10 centrifuge concentrator and injected into a Pharmacia 10/30 Superdex 200 HR gel filtration column. Samples were eluted with buffer identical to that described above (no cholate) at 0.5 ml per minute. Fractions from chromatography were run on an 8–25% gradient SDS polyacrylamide gel to determine apparent size and then checked for coagulation activity. The chromatogram showing elution of TF incorporated into an excess population of MSP1 nanodiscs is shown in FIGS. 16A–16B.

The activity of TF in several disk fractions was determined by coagulation assays with human serum. Activity was monitored in fractions 25–28 as the inverse of coagulation time. Activity was highest in fraction 25 at 40 $hr^{-1}$ and decreased through fraction 28 at 30 $hr^{-1}$. This is expected from the size chromatogram in that the leading edge of the nanodisc peak has a larger effective mass due to the incorporation of TF in the MSP-supported bilayer. This assay thus demonstrates that TF is incorporated into nanodiscs in an active conformation and that the membrane environment of the nanodisc closely mimics that of the native membrane system.

Cytochrome b5 is a membrane anchored heme protein having a single membrane anchor domain that penetrates the membrane bilayer. Cytochrome b5 solubilized from its native membrane exists as large aggregates in the absence of detergent and appears as a smear rather than a discrete band on native polyacrylamide gel electrophoresis. Formation of nanodiscs through a self-assembly process wherein cytochrome b5 is added to the preparation of MSP and phospholipid results in the incorporation of cytochrome b5 into nanodisc structures. This is verified by the intense heme staining of the band corresponding to nanodiscs in the right panel of See FIG. 17B, lane 4. Cytochrome b5-containing nanodiscs separated by anion exchange chromatography are shown in lanes 5 and 6 of FIG. 17B. Two peaks elute from the anion exchange column near 310 mM NaCl and near 370 NaCl. Discs alone elute near 310 mM NaCl, and cytochrome b5 alone elutes between 450 and 700 mM NaCl. These data show that cytochrome b5 can be successfully solubilized using MSP technology and that disc complexes containing cytochrome b5 can be chromatographically separated and purified away from the undesired aggregated material. The optical absorption properties of the heme chromophore of the purified material demonstrate that the heme active site in a native conformation.

Nanodiscs can also be formed by mixing 20 μl of apo A-I (10 mg/ml), 6.6 μl cytochrome b5 (0.5 mM) and 50 μl egg phosphatidylcholine/sodium cholate (11.2 egg PC, 6.2 mg/ml sodium cholate), incubating overnight at 4° C., followed by dialyzing to remove cholate. Purification was accomplished using a Pharmacia MonoQ FPLC anion exchange column equilibrated in 25 mM Tris Cl, pH 8.0. A linear gradient was run at 0.5 ml/min from 0–1 M NaCl in 20 min.

Example 8

Embedded Membrane Protein Incorporation

Cytochrome P450 2B4 from rabbit liver microsomes, cytochrome P450 3A4 found in nature in human liver microsomes and cytochrome P450 6B1 from insect microsomes are representative of embedded membrane proteins.

Cytochrome P450 2B4 was isolated from rabbit liver microsomes after induction with phenobarbital. Formation of 2B4 nanodiscs is as follows. Cytochrome P450 2B4 was reconstituted into disks by the detergent dialysis method. The buffer consisted of 10 mM Tris-HCl pH 8.0, 0.1 M NaCl, 10% (v/v) glycerol. The mixture of apo A-I, cholate and phospholipid (1:220:110 mole ratio) was incubated for 8 hours at 37° C. followed by addition of P450 (1:0.5, apo A-I:P450 mole ratio) and incubation overnight at room temperature. The mixture was dialyzed using a 10,000 MW cutoff slide-a-lyzer (Pierce Chemical Co., Rockford, Ill.) at room temperature for two hours followed by a change of buffer and continued dialysis at 4° C. It was found that 82% of the P450 content could be recovered under these conditions. After dialysis, the mixture was injected onto a Superdex 200 HR10/30 gel filtration column (Pharmacia, Uppsala, Sweden) equilibrated in reconstitution buffer at room temperature at a flow rate of 0.25 ml/minute with collection of 0.5 ml fractions. Fractions were assayed using native polyacrylamide gradient gel electrophoresis on 8–25% gradient native gels and Coomassie staining using the Phastgel system (Pharmacia, Uppsala, Sweden).

Human cytochrome P450 3A4, normally from liver microsomes, has also been cloned, expressed in *E. coli* and purified and incorporated into MSP-supported bilayer nanodiscs. 10 nanomoles of MSP2, one micromole of lipid, 5 nanomoles of cytochrome P450 3A4 protein and 2 micromoles cholic acid were incubated together at 37° C. for 2 hours. The incubated mixture was then dialyzed in a 10 K Slide-A-lyzer Dialysis Cassette (Pierce Chemical Co., Rockford, Ill.). The dialysis was carried out with 10 mM potassium phosphate (pH 7.4) 150 mM NaCl buffer. The sample was dialyzed at 37° C. for 6 hours followed by a buffer change, and dialysis continued at 4° C. with two buffer changes at 12 hour intervals. The samples were then fractionated on a Superdex 200 HR 10/30 column (Pharmacia, Uppsala, SE) equilibrated in dialysis buffer at room temperature at a flow rate of 0.5 ml/min.

The four graphs (FIGS. 18–20) show that the retention times of the cytochrome P450 3A4 (observed by absorbance at 417 nm) and the nanodiscs (monitored at 280 nm where both MSP and the 3A4 protein absorb) elute from the column at the same time, at approximately 24 min. This elution time also correlates closely to the calculated retention time of the disc protein complex. Further evidence that supports this is a native polyacrylamide gel electropherogram that directly measures the size of the eluted particles (FIG. 21).

Cytochrome P450 6B1 is another model embedded membrane protein. This cytochrome has been isolated from *Papilio polyxenes*, the black swallowtail. These butterflies feed exclusively on plants producing furanocoumarins, plant metabolites that are phototoxic to most organisms. Cytochrome 6B1 catalyzes the detoxification of furanocoumarins.

In order to show a new utility of the MSP methodology of the present invention, we demonstrated that isolated membranes containing their repertoire of membrane proteins could be sued as a source for incorporating membrane proteins into nano discs. An important illustrative embodiment is the use of the common insect cell (Sf9)-baculovirus expression system which is used widely as a heterologous expression system. Thus, we used an insect cell line co-infected such that a microsomal preparation containing overexpressed insect 6B 1 and also overexpressed insect NADPH cytochrome P450 reductase. In these experiments we not only demonstrate that MSP nanodiscs can be used to incorporate another cytochrome P450 system into soluble monodisperse particles but also that the source of this P450 could be simply whole membranes containing this protein.

Figure 22:
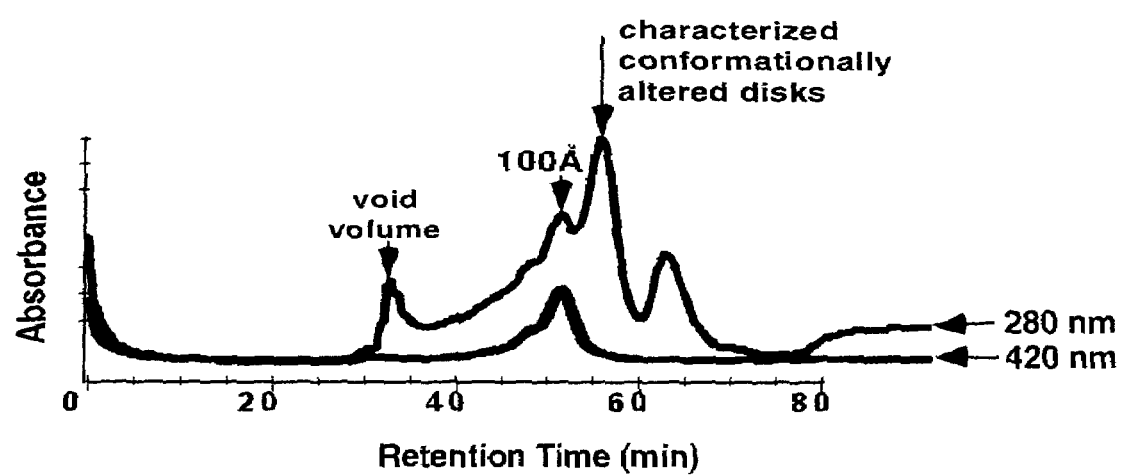
FIG. 22 illustrates the results of HPLC chromatography of MSP-solubilized cytochrome P450 6B1 over a Superdex 200 sizing column. Retention times indicate nanodisc particles containing 6B1 (420 nm trace). about 1 The flow rate was 0.25 ml/min.
Figure 23:
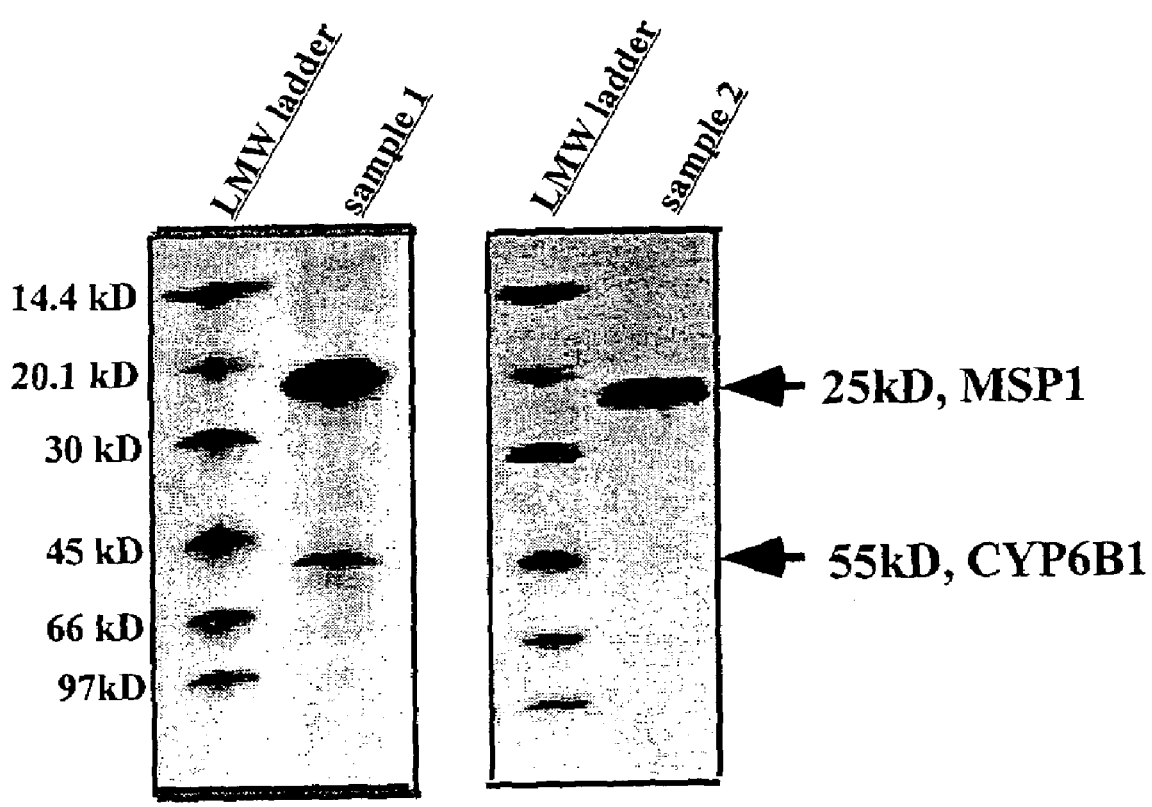
FIG. 23 illustrates the results of PAGE with sample 1 (nanodiscs prepared with microsomal membranes from cells coexpressing cytochrome P450 6B1 and NADPH P450 reductase. Sample 2 contains control microsomes.

A standard baculovirus expression system was used to obtain microsomal preparations with overexpressed insect cytochrome 6B1 and insect NADPH P450 reductase. Based on the lipid concentration contained in the microsomal preparations, MSP technology was used to assemble microsomal proteins into nanoparticle discs using a ratio of 110:1:220 lipid:MSP1:cholate. The microsomal sample was detergent solubilized with cholate and mixed with MSP1. The sample was incubated at 4° C. for 2 hours. The detergent can be removed by dialysis or hydrophobic beads. In this experiment BIOBEADS (hydrophobic beads, BioRad, Hercules, Calif.) were added in excess (0.25 g per 1 ml disc mixture) and incubated for 2 hours at 4° C. for 2 hours to remove detergent. The sample was removed from the beads and the His$_6$-tagged MSP was isolated by using a batch purification method with Ni$^{2+}$ resin. The MSP discs were then isolated by Superdex sizing column chromatography (FIG. 22). Incorporation of P450 into the His$_6$-tagged discs was followed by CO difference spectroscopy of nickel affinity column purified and sizing column-purified fractions (FIG. 24). SDS-PAGE was performed to verify incorporation of cytochrome P450 6B1 into discs (FIG. 23).

The endogenous (natural) ratio of cytochrome P450 to reductase is about 10–20. To obtain activity of the cytochrome P450 6B1 after reconstitution into discs, it is preferred that an excess of reductase be added to the reconstitution mixture, such that a P450 molecule and reductase molecule both partition into a single disc. Supplementation of the microsomal preparation with exogenously added reductase has been successfully demonstrated.

The protocol for making discs using microsomal preparations was used with one modification. Exogenous rat reductase was added after the solubilization step of the microsomal preparation with cholate and before the addition of MSP1. Otherwise identical disc assembly and purification procedures were followed. The sample was separated by a Superdex sizing column, where absorbance at 280 nm indicates the presence of MSP1, absorbance at 420 and 456 nm indicates the presence of ferric species, and absorbance at 456 nm also indicates presence of reductase. A ratio plot of 456 to 420 nm was made; it showed positions on the chromatogram where the absorbance at 456 nm was above that associated with cytochrome P450 6B 1 and, therefore, could be attributed to absorbance by reductase. Retention times reflected the presence of 10 nm particles containing cytochrome P450 6B1 and reductase (FIG. 26).

MSP-supported nanodiscs with purified proteins, membrane fragments or disrupted membranes can be used in high throughput screening ventures, for example, to identify new pharmaceuticals and other biologically active molecules.

Example 9

Integral Membrane Protein Incorporation

Bacteriorhodopsin is a model integral membrane protein. Bacteriorhodopsin was incorporated into nano scale structures using the following procedure, which is a protocol useful for other proteins as well. Bacteriorhodopsin was obtained as lyophilized purple membrane from Sigma (St. Louis, Mo.). 1 mg BR was suspended in 1 ml 25 mM potassium phosphate pH 6.9. 1 ml 90 mM n-octyl B-D-glucopyranoside in the same buffer was added and the sample placed in the dark at 24° C. overnight. This treatment produces a detergent-solubilized monomeric form (Dencher et al., 1982). BR was quantitated assuming a molar extinction coefficient at 550 nm of 63,000. BR (7.8 uM) was mixed with MSP1 (97 mM) or MSP2 (110 mM) and cholate (50 mM) to give final molar ratios of MSP1:BR of 10:1 or MSP2:BR of 5:1 and a cholate concentration of approximately 8 mM. For reconstitution with phospholipid, the lipid is solubilized as above in the presence of 50 mM cholate and mixed with MSP1 at a mole ratio of 1 MSP1:110 lipids:0.1 BR. The mixture was incubated at room temperature for ~3 hours followed by dialysis overnight against 1000 volumes of buffer using 10,000 MW cutoff dialysis devices (Slide-a-lyzer, Pierce Chemical). Dialysis was continued at 4 degrees for 2 days with several changes of buffer. 10 mM HEPES, pH 7.5, 0.15 M NaCl buffer can be used. Tris buffer pH 7.5 or pH 8 has also been used successfully.

The 5-hydroxytryptamine 1A G protein coupled receptor from human has been incorporated into MSP-containing nanoparticles. A commercially available insect cell expression system that provides a membrane fraction containing the human 5-hydroxytryptamine 1A GPCR was supported using MSP compositions. Briefly, the 5-HT receptor containing membrane preparation was mixed with phospholipids (phosphatidyl choline, phosphatidylethanolamine, phosphatidyl serine) at a ratio of 45:45:10, MSP1 and cholate.

5-HT1A receptors overexpressed in a commercially available Sf9 insect cell membrane preparation (Sigma Chemical Co., St. Louis, Mo.) were solubilized using the following protocol. POPC, POPS and POPE (Avanti Phospholipids) in chloroform were mixed in a 45:10:45 mole ratio and dried down under a stream of nitrogen, then placed under vacuum for several hours to remove residual solvent. The phospholipids were dispersed in 50 mM Tris pH 7.4, 0.2 M NaCl, 50 mM sodium cholate buffer at a concentration of 25 mM phospholipid. Five microliters of the sf9 membrane preparation (0.2 mg/ml protein), 1.62 microliters of phospholipid in buffer, 2.4 microliters of MSP1 (4.2 mg/ml) and 0.28 microliters 4 M NaCl were mixed and left for 1 hour on ice. The mixture was diluted to 100 microliters total volume with 50 mM Tris pH 7.4 and dialyzed in a mini slide-a-lyzer (Pierce Chemical) against 50 mM Tris pH 7.4 at 4° C. (two one-liter changes of buffer). To determine the amount of 5HT1A receptor associated with nanodisks, a radio labeled ligand was bound to the receptor and disk-receptor-ligand complexes were isolated using the 6-histidine tag present in the MSP1 according to the following protocol. After dialysis, the mixture was diluted to 200 microliters total volume with 50 mM Tris pH 7.4. Ninety-five microliters of the diluted mixture were placed into each of two tubes. One hundred five microliters of stock reagent were added to give final concentrations of 50 mM Tris pH 7.4, 10 mM MgSO4, 0.5 mM EDTA, 0.1% ascorbic acid in a final volume of 200 microliters. Tritium-labeled 8-hydroxy-DPAT (specific activity 135000 Ci/mole) was added to each tube to give a concentration of 1.5 nM. As a control, unlabeled metergoline (final concentration 100 micromolar) was added to one of the tubes as a competitive ligand. After 1 hour on ice, the mixture was applied to 200 microliters of Ni-chelating resin to specifically bind receptor associated with 6Histidine-tagged MSP1 disks. The resin was washed three times with 0.5 ml of cold 50 mM Tris pH 7.4 to remove non-specifically bound ligand. Specifically bound radiolabeled 8-hydroxy-DPAT bound to receptor/disk complexes was eluted with 0.5 ml 0.5 Molar imidazole in 10 mM Tris pH 7.4, 0.5 M NaCl. Scintillation cocktail was mixed with the eluate and specifically bound radioligand was determined by scintillation counting. Between five and fifteen percent of the receptor initially present in the sf9 membrane was found to be associated with MSP1 nanodisks.

The particles into which the 5-HT GPCR had incorporated were dialyzed. Functionality (in terms of ligand binding) was tested using dialysis against buffer containing tritiated 8-OH-DPAT, an agonist of this receptor. The particles were then run over a Ni-NTA column to bind via the histidine tag on the MSP1 and to separate the particles from 8-OH-DPAT which had not bound to the particles, and the material bound to the column was then eluted. Association of the tritium labeled agonist was demonstrated, showing that the incorporated GPCR retained its ability to bind agonist.

Example 10

Analysis of MSP-Supported Nano Disc Phospholipid Assemblies

The particles resulting from self assembly of membrane scaffold proteins and phospholipids, either with or without an additional target protein, were analyzed as follows.

Bacteriorhodopsin-containing particles were dialyzed, and the resulting mixture was injected onto a Superdex 200 HR10/30 gel filtration column (Pharmacia) and eluted with buffer at 0.5 ml/min at room temperature. Absorbance was monitored at 280 nm for protein and 550 nm for BR. 0.5 ml fractions were collected. The column was calibrated using a mixture of thyroglobulin (669 kDa, Stoke's diameter 170 A), ferritin (440 kDa, Stoke's diameter 122 A), catalase (232 kDa, Stoke's diameter 92 A), lactate dehydrogenase (140 kDa, Stoke's diameter 82 A), bovine serum albumin (66 kDa, Stoke's diameter 71 A), and horse heart cytochrome c (12.4 kDa, Stoke's diameter 35.6 A).

Atomic Force Microscopy (AFM) was performed with a Digital Instruments Nanoscope IIIa in contact mode with sharpened silicon nitride probes under buffer. MSP1 and MSP2 dipalmitoyl phosphatidylcholine particles were treated with 1:50 Factor Xa:MSP protein by mass in 10 mM Tris pH 8, 0.15 M NaCl, 2 mM $CaCl_2$ for 8 hours. 2–10 ml sample was placed on a freshly cleaved mica surface along with 20 ml imaging buffer (10 mM Tris pH 8, 0.15 M NaCl, 10 mM $MgCl_2$) and incubated for 30 minutes or longer before mounting sample in the fluid cell. Several milliliters of buffer were flushed through the fluid cell to remove unadsorbed material.

Phosphate analysis of the nano scale particles was carried out as follows. Phosphate assay procedures were adapted from Chen et al. (1956) Anal. Chem. 28:1756–1758 and Fiske and Subbarow (1925). Samples containing roughly 40 mmoles lipid phosphate were dried down in glass tubes. 75 ml 8.9 N $H_2SO_4$ was added to each tube and heated to 210° C. for 30 minutes. 1 drop 30% $H_2O_2$ was added to each tube and heated for 30 minutes. Tubes were cooled, 0.65 ml $H_2O$ was added followed by 83.3 ml 2.5% w/v ammonium molybdate tetrahydrate followed by vortexing and the addition of 83.3 ml 10% w/v ascorbic acid. After mixing, the tubes were placed in a boiling water bath for 7 minutes. Absorbance was read at 820 nm. Absorbance was calibrated using potassium phosphate standards from 0 to 100 nmol phosphate. Buffer blanks from column chromatography were included for MSP proteins.

Example 12

MSP-Supported Structures on Surfaces

Nanodiscs comprising MSPs and a protein of interest can be assembled onto a gold surface. The utility of this relates to the resulting epitaxial presentation of a target incorporated into a nanodisc assembly to the solution. This offers an ideal system for quantitating binding of other macromolecules or small molecules tagged with dielectric contrast agents to the target protein. A common methods of accomplishing such measurements uses surface plasmon resonance (SPR) technology. SPR is a common technique used to monitor biomolecular interactions at surfaces. The ability of SPR to rapidly detect and quantitate unlabeled protein interactions on gold surfaces is useful for creating high through put chip assays for diverse membrane proteins (embedded and solubilized) on discs.

Discs consisting of the phospholipid DPPC either with or without an additional thiolated lipid and MSP1 protein were prepared as follows. A 25 mM lipid mixture containing phosphatidylcholine was solubilized with 50 mM cholate in 10 mM Tris Cl, 150 mM NaCl at pH 8.0 were combined and incubated overnight at 37° C. For thiolated discs, 90% phosphatidylcholine and 10% thiolated lipid (ATA-TEG-DSPA, Northern Lipids) was solubilized in 3.3 mM Tris Cl, 66.7 mM borate, 150 mM NaCl at pH 9.0 in order to unmask the thiols in the thiolated lipids. MSP1 and lipid (1:100) were combined and incubated overnight at 37° C. The sample was then dialyzed at 37° C. (10,000 MW cutoff membrane) against buffer containing 10 mM Tris Cl, 150 mM NaCl at pH 8.0 without cholate for 2 hours. Dialysis was then continued at 4° C. for an additional 6 hours with buffer changes every 2 hours. The approximately 1 ml sample was concentrated to <250 µl using a YM-10 centrifuge concentrator and injected onto a Pharmacia 10/30 Superdex 200 HR gel filtration column. Samples were eluted from the column using the stated buffer without cholate at flow rates of 0.5 ml/min. Fractions from chromatography were analyzed by polyacrylamide gel electrophoresis using 8–25% gradient polyacrylamide gel to determine apparent size.

Figure 27:
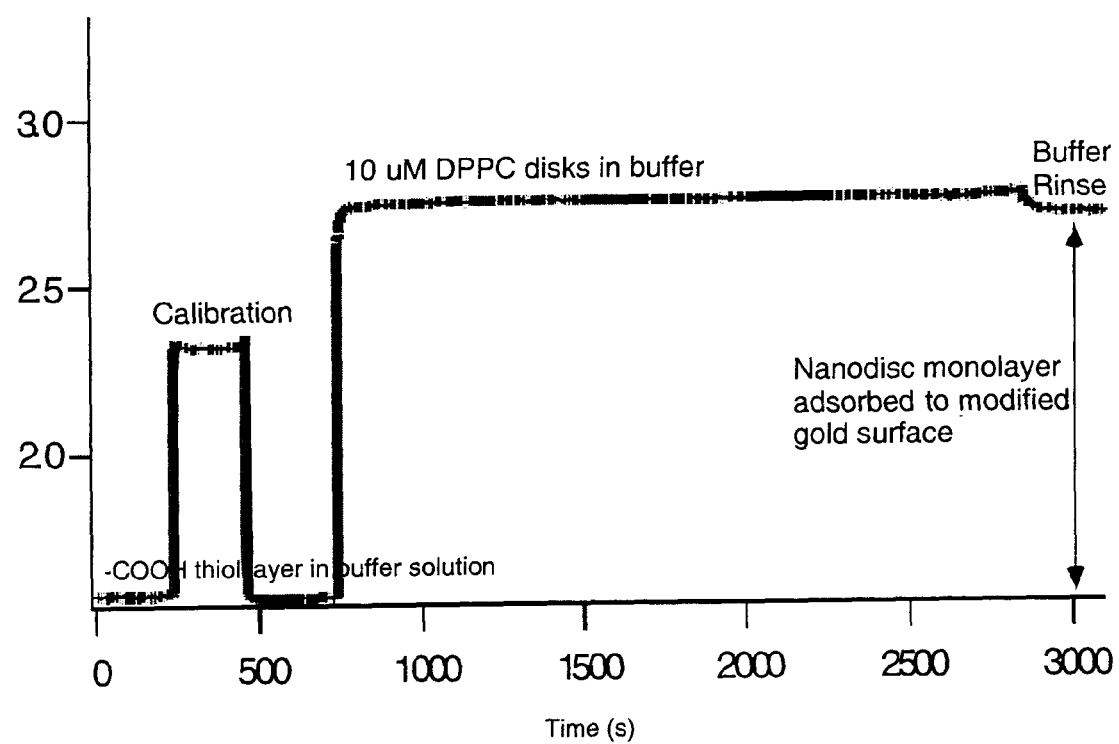
FIG. 27 illustrates the binding of DPPC nanodiscs containing carboxyl terminated thiols to a gold surface, as monitored by surface plasmon resonance.

The nanodisc samples (3–20 µM) prepared as described were injected into an SPR instrument to determine if the discs would bind to the gold surface. Both the DPPC and 10% thiolated lipid discs adsorbed to a gold surface and a modified gold surface covered with a monolayer of methyl terminated thiol (nonanethiol) or carboxyl terminated thiol (11-mercaptoundecanoic acid). Thiolated discs were injected using a buffer consisting of 3.3 mM Tris, 66.7 mM borate, 150 mM NaCl, pH 9.0. DPPC discs were injected using a buffer of 10 mM Tris, 150 mM NaCl, pH 7.5 or pH 8.0. In all cases, the discs could not be removed even under harsh conditions (0.5 M HCl). Surface coverage was shown to increase with increasing concentration of discs injected (3 µM vs. 19 µM). Discs do not form perfectly packed monolayers; accordingly, surface coverage is limited by the jamming limit (theoretical maximum coverage based on random sequential absorption to the surface modeling discs as identical non-overlapping hard spheres) of 0.547. The coverage for a full monolayer of discs was calculated based on an assumption of disc height of 5.5 nm and a refractive index between 1.45 and 1.5. The full monolayer values were multiplied by the jamming limit to determine the maximum coverage that was then used to determine percent coverage based on experimental values. When the disc concentration was at least 10 µM, the estimated coverages were between about 62 and about 103%. The resultant SPR trace demonstrating association of the nanodiscs to the gold surface is shown in FIG. 27.

LITERATURE CITED

Atkinson, D. and Small, D. M. (1986) *Ann. Rev. Biophys. Chem.* 15: 403–456.
Bayburt, T. H. et al. (1998) *J. Struct. Biol.* 123: 37–44.
Bayburt, T. H. et al. (2000) *Langmuir* 16: 5993–5997.
Boguski, M. S. et al. (1986) *J. of lipid Research* 27: 1011–1034.
Borhani, D. W. et al. (1997) *Proc. Natl. Acad. Sci USA* 94: 12291–12296.
Brouillette, C. G. et al. (1984) *Biochemistry* 23: 359–367.
Carlson, J. W. et al. (2000) *Langmuir* 16: 3927–3931.
Carlson, J. W. et al. (1997) *Biophys. J.* 73: 1184–1189.
Chen et al. (1956) *Anal. Chem.* 28:1756–1758.

Dalton, M. B. and Swaney, J. B. (1993) *J. Biol. Chem.* 268: 19274–19283.
Dencher, N. A. and Heyn, M. P. (1982) *Methods Enz.* 88: 5–10.
Drake et al. (1989) *Am. J. Pathol.* 134: 1087–1097.
Durbin, D. M. and Jonas, A. (1999) *J. Lipid Research* 40: 2293–2302.
Fidge, N. H. (1999) *J. Lipid Research* 40: 187–201.
Fielding, P. E. and Fielding, C. J. (1991) *Biochemistry of Lipids, Lipoproteins, and Membranes*. D. E. Vance and J. Vance. Amsterdam, Elsevier Press: 427–459.
Fiske and Subbarow (1925) *J. Biol. Chem.* 66:374–389
Forte, T. M. et al. (1971) *Biochim. Biophys. Acta* 248: 381–386.
Frank, P. G. et al. (1997) *Biochemistry* 36: 1798–1806.
Friis, E. P. et al. (1999) *Proc. Natl Acad. Sci. USA* 96: 1379–84.
Glomset, J. A. (1968) *J. Lipid Research* 9: 155–167.
Higuchi, R. et al. (1988) *Nucl. Acids Res.* 16: 7351.
Holvoet, P. et al. (1995) *Biochemistry* 34: 13334–13342.
Jonas, A. (1986) *Methods Enzymol.* 128: 553–582.
Jonas, A. (1991) *Biochim. Biophys. Acta* 1084: 205–220.
Jonas, A. et al. (1989) *J. Biol. Chem.* 264: 4818–4824.
Koppaka, V. et al. (1999) *J. Biol. Chem.* 274: 14541–14544.
Miller, J. P. et al. (1996) *Biochemistry* 35: 1466–1474.
Mukhopadhyay, R. et al. (2000) *J. Inorg. Biochem.* 78: 251–254.
Nemerson, Y. and Repke, D. (1985) *Thromb. Res.* 40:350–358.
Phillips, J. C. et al. (1997) *Biophysics Journal* 73: 2337–2346.
Rezaie et al. (1992) *Protein Expression and Purification* 3: 453–460.
Robinson, C. R. and Sauer, R. T. (1998) *Proc. Natl. Acad. Sci. USA* 95(11):5929–34].
Rogers, D. P. et al. (1998) *Biochemistry* 37: 945–955.
Rogers, D. P. et al. (1998) *Biochemistry* 37: 11714–11725.
Segrest, J. P. et al. (1999) *J. Biol. Chem.* 274: 31755–31758.
Tocanne, J.-F. et al. (1994) *Chemistry and Physics of Lipids* 73: 139–158.
Wald, J. H. et al. (1990) *J. Biol. Chem.* 265: 20044–20050.
Wald, J. H. et al. (1990) *J. Biol. Chem.* 265: 20037–20043.
Wang, M. et al. (1997) *Proc. Natl. Acad. Sci. USA* 94: 8411–8416.
Wlodawer, A. et al. (1979) *FEBS Lett.* 104: 231–2 Segr35.

What is claimed is:

1. A nanoscale particle comprising an artificial membrane scaffold protein and at least one G protein coupled receptor protein, and further comprising a phospholipid or a mixture of phospholipids, wherein said nanoscale particle has a diameter between 5 nm and 500 nm, wherein said artificial membrane scaffold protein, in an aqueous environment, self-assembles in the presence or absence of phospholipid or in the presence of a mixture of phospholipids, into a nanoscale particle between about 5 nm and about 500 nm in diameter, wherein said membrane scaffold protein is amphipathic and wherein said membrane scaffold protein is a derivative or a truncated form of human apolipoprotein A1, forms at least one alpha helix-, and lacks the N-terminal globular domain of a polioprprotein A1 (amino acids 8 to 50 of SEQ ID NO: 2).

2. The nanoscale particle of claim 1, wherein said G-protein coupled receptor is a 5-hydroxytryptamine receptor.

3. The nanoscale particle of claim 1, wherein said artificial membrane scaffold protein comprises an amino acid sequence selected from the group consisting of SEQ ID NO:6, SEQ ID NO:9, SEQ ID NO:17, amino acids 13 to 414 of SEQ ID NO:17, SEQ ID NO:19, amino acids 13 to 422 of SEQ ID NO:19, SEQ ID NO:23, amino acids 13 to 168 of SEQ ID NO:23, SEQ ID NO:29, amino acids 13 to 169 of SEQ ID NO:29, SEQ ID NO:43, amino acids 13 to 201 of SEQ ID NO:43, SEQ ID NO:44, amino acids 13 to 201 of SEQ ID NO:44, SEQ ID NO:45, and amino acids 13 to 392 of SEQ ID NO:45.

4. The nanoscale particle of claim 1, wherein said membrane scaffold protein is fused genetically with the G protein coupled receptor protein.

5. A tandem repeat membrane scaffold protein that, in an aqueous environment, self assembles with a phospholipid or a mixture of phospholipids, into a nanoscale particle between 5 nm and 500 nm in diameter, wherein said membrane scaffold protein is amphipathic, wherein said membrane scaffold protein forms at least one alpha helix and wherein said membrane scaffold protein has the amino acid sequence given in SEQ ID NO:17, amino acids 13 to 414 of SEQ ID NO:17, SEQ ID NO:19, amino acids 13 to 422 of SEQ ID NO:19, SEQ ID NO:45 or amino acids 13 to 392 of SEQ ID NO:45.

* * * * *